(12) United States Patent
Brunkow et al.

(10) Patent No.: US 6,475,739 B2
(45) Date of Patent: Nov. 5, 2002

(54) METHODS FOR IDENTIFYING GENOMIC DELETIONS

(75) Inventors: Mary E. Brunkow; Sean Proll; Bryan Paeper, all of Seattle; Karen Staehling-Hampton, Bothell, all of WA (US)

(73) Assignee: Celltech R&D, Inc., Bothell, WA (US)

( * ) Notice: Subject to any disclaimer, the term of this patent is extended or adjusted under 35 U.S.C. 154(b) by 0 days.

(21) Appl. No.: 09/918,686

(22) Filed: Jul. 30, 2001

(65) Prior Publication Data

US 2002/0076720 A1 Jun. 20, 2002

Related U.S. Application Data

(60) Provisional application No. 60/303,386, filed on Jul. 6, 2001, and provisional application No. 60/221,855, filed on Jul. 28, 2000.

(51) Int. Cl.[7] .............. C12Q 1/68; C12P 19/34; C07H 21/04
(52) U.S. Cl. .......... 435/6; 435/91.1; 435/91.2; 536/24.3; 536/24.31
(58) Field of Search .......... 435/6, 91.1, 91.2; 536/24.3, 24.31

(56) References Cited

PUBLICATIONS

Keinlinen, M. et al., "Use of Polymerase Chain Reaction to Detect Heterozygous Familial Hypercholesterolemia", Clin. Chemistry, vol. 36, pp. 900–903 (1990).*

Balemans et al., "Localization of the Gene for Van Buchem Disease to a Candidate Region of Less than 1 cM on Chromosome 17," *American Journal of Medicine 61 (suppl.)*:A12, 1997.

Balemans et al., "Localization of the Gene for Sclerosteosis to the Van Buchem Disease–Gene Region on Chromosome 17q12–q21," *American Journal of Medicine 64*:1661–1669, 1999.

Beighton et al., "The Syndromic Status of Sclerosteosis and Van Buchem Disease," *Clinical Genetetics 25*:175–181, 1984.

Brunkow et al., "Bone Dysplasia Sclerosteosis Results from Loss of the SOST Gene Product, a Novel Cystine Knot––Containing Protein," *Am. J. Hum. Genet. 68*:577–589, 2001.

Burge et al., "Prediction of Complete Gene Structures in Human Genomic DNA," *J. Mol. Biol. 268*:78–94, 1997.

Fryns et al., "Facial Paralysis at the Age of 2 Months as a First Clinical Sign of Van Buchem Disease (Endosteal Hyperostosis)," *European Journal of Pediatrics 147*:99–100, 1988.

Van Buchem et al., "Hyperostosis Corticalis Generalisata," *American Journal of Medicine 33*:387–397, 1962.

* cited by examiner

*Primary Examiner*—Kenneth R. Horlick
*Assistant Examiner*—Teresa Stzelecka
(74) *Attorney, Agent, or Firm*—Seed Intellectual Property Law Group, PLLC

(57) ABSTRACT

The genomic locus responsible for Van Buchem's disease is narrowed to an approximately 92 kb region of human chromosome 17 at 17q21. Individuals afflicted with or carriers of Van Buchem's disease exhibit a 52 kb deletion within this 92 kb region. Methods are provided that permit the differentiation between individuals homozygous for and therefore afflicted with Van Buchem's disease, individuals heterozygous for and therefore carriers of Van Buchem's disease, and individuals who are normal with respect to Van Buchem's disease. Also provided are general methodologies for the detection of a wide variety of large genomic deletions.

19 Claims, 3 Drawing Sheets

SEQUENCE LISTING

<160> NUMBER OF SEQ ID NOS: 105

<210> SEQ ID NO 1
<211> LENGTH: 92139
<212> TYPE: DNA
<213> ORGANISM: Homo sapiens
<220> FEATURE:
<221> NAME/KEY: misc_feature
<222> LOCATION: 7043, 8369, 8401
<223> OTHER INFORMATION: n = A,T,C or G

<400> SEQUENCE: 1

| | | | | | |
|---|---|---|---|---|---|
| caaagatttg | attctttata | cttttatgt | tcaaattttt | aaaaatgcaa | aagaaaaaaa | 60 |
| actaaatagg | agggaaaaat | gttcaacaga | aaatttaccc | caggaaccaa | aaaaaaaaaa | 120 |
| aaacccaaaa | ctaaagtctc | tccttaaagt | acacacacat | gtggccagct | actcctatgt | 180 |
| gtgtgcacac | acctatgtcg | ggcttgctcc | tgccctcca | atgcaccagc | ctacctactg | 240 |
| ggatccctg | tatgtgtatt | tgtcgccaat | gacactaaac | attttcactg | tcccaaccca | 300 |
| gacgcaccag | ctgacgagga | gttcgtcctg | gagcccagag | caaatgcctg | cagagggctg | 360 |
| gaccagggct | gctgggacac | acttttaaat | cctgcggtgg | ggagagagtg | acaaatttct | 420 |
| gaagtgaaat | gtgagagagg | agagggaggg | gttaacccac | acacacaaga | tcccctccaa | 480 |
| ccaaaaccct | agcaggcaac | tattaatcat | cagaaacctt | atatgcacat | ctaatgggat | 540 |
| ttgcagatgg | agacttttaa | agaaacattg | tctgtatttt | tttttaagg | aaagagagca | 600 |
| gcacacacac | acatacacac | acaccgtctt | taatgtgcct | cctgtaacac | tatgaagtta | 660 |
| tttttattgc | actgttaaca | aaattcccca | agtcttggat | ttagaaaaag | ccttaagtca | 720 |
| gatccagaat | ccatcaaatg | ccaaattcca | gggagtgaag | tgaggaataa | gagcaagaga | 780 |
| caagcttggt | gattgcattt | gatttaaagg | cccttctact | gctgcctgcg | aaaaaggaag | 840 |
| gtggattaaa | agaaatcttt | tttgcaagtc | tcagcggccc | actgtggtct | gcagtacaaa | 900 |
| gaaaggcaca | ctctagaaaa | aaagaatttc | tctctgccca | gagtgacatt | ctcactttct | 960 |
| cagtaactta | aaaaaacaat | cagattcttc | cttccgctct | ttaacctcca | acatacatgc | 1020 |
| caattagcca | cactcttctc | tagagaggtt | tcaagtcatt | tttcttcaca | gcaatggcaa | 1080 |
| ggctcttaaa | taaggtcctt | gaagtttctt | cgggtctcct | cccacctgct | ccctgccccc | 1140 |
| ttcacctcca | cccacctgct | tccctttctc | atcccccaga | ggcggaggct | tccgaggaat | 1200 |
| tgggggtagg | gaaataggaa | tcaggggctc | ctcattcccc | aaaggagcct | ctttggcaag | 1260 |
| caggcacgtg | ggtctccggg | ctggtgcaca | tcacagggca | gccagcccaa | gtgccatctt | 1320 |
| gatgcccaat | cagtcttcct | catggctgcg | ccctgctggt | ctctcagagg | gttaatgcaa | 1380 |
| tttcttggag | gacgacattc | ctaacaccca | ggggccagaa | ctccttcccc | actgttatt | 1440 |
| cccatggccc | agagcagcag | gatggggggca | gaaacaggca | tggaccttaa | cagcagcgtc | 1500 |
| tctgctggct | gcttccaaag | acggcgaggg | ttccctgagg | aggggcccct | aggtcttagc | 1560 |
| tctgcagcct | ggaggtgggg | ccctgggggg | tgggtgcagg | agatgctcct | aggaggagcc | 1620 |
| gaagggcacc | cagggatgtg | gaatgaagcc | acgactggcc | tttaatccag | aaactccagt | 1680 |
| cagatacaca | tcctgggagc | aggagcagct | gtaaaagatg | gggaggggtg | tacatatgaa | 1740 |
| aagatgtgcc | ctcttctgga | acaagcggtc | agagtgttgt | agaccagtag | agtggatggg | 1800 |
| gtcatagctg | tcaaccagac | tcatctttct | gctttgccca | gggcttagct | gtggcacaca | 1860 |
| caattctctg | agcctcacaa | ctttcctagg | atgggtaagt | aagaattatg | tctccatttt | 1920 |

```
gcagatgaca aaaccgaggc tcagatggat gactgggctg cccagactca cacagctaag    1980
aaatggtgga atcagcactt ggcctcaggt gtcctgctgt tcagtttgga gcaggccaga    2040
tgcagaggag gaggcatggg gtttgaggtt agacgggtct gagttcaagc cccaggtctg    2100
ccacttcctg gctgtgtgcc ctggaacaag tcaccttatc tctctgaact tcttttttt    2160 ttttttcttt tgagatgga gtctcgttct gtcgcccagg ctggagtgca gtggcatgat     2220
ctcagctcac tgcaagctcc gcctcccggg ctcacgccat tctcttgcct cagcctcccg    2280
agtagctggg actacaagca cccgccacca cgcccggcta ttttttgta ttttttagta     2340 gagacgggt ttcaccgtgt tagccaggat ggtctcaatc tcctgacctc gtgatccgcc      2400
cgcctcggcc tcccaaagtg ctgggattac aggcatgagc caccatgcct ggccatctct    2460
ctgaacttct gtttcctcat ctgagatgac agtcagagtg ggatctgtgt aaggcacttt    2520
gcaccttaca cattttacc cccacggatt cccacaaaag ccttctgagg caacagtcat     2580
tctcatcagc tccgttctc tctctctctt ttctttttat cagctccgtt tttcagcaga     2640
agactctgat gcacagatag actgtgtaac ctgcacaagg ccacacagca gggaagcagc    2700
ggacccagga ttcaaattga ggcagcccag cccacagaca tttgcaaatc ttcaatgaaa    2760
tcctttatgt aggccaggca cggtggctca gacctataat cccagcactt tggaaggctg    2820
aggcaggcag atcatttgag gccaggagtt caagaccagc ccggccaaca tggtaaaacc    2880
ccgtctctaa tagaaataca aaattaggc cgggcgcggt ggctcatgcc tgtaatccca     2940
ccactttggg aggccgaggc gggtggatca tgcggtcagg agatcgagac catcctggct    3000
aacacagtga aaccccgtct ctactagaaa tacaaaaaaa aaaaaaaaa ggcgggcgtg     3060 gtggcgggcg cctgtagtcc cagctacttg ggaggctgaa gcaggagaat ggtgtgaacc    3120
cgggaagcag agcttgcagt gcaccgagat cacgtcactg cactccagcc tgggtgacag    3180
agcgagactc catctcaaaa aaaaaaaaa aaagaaatac aaaaattagc tgggtgtggt     3240
ggcacatgcc tgtaatccca gctactcggg aggctgaggg caggagaatc gcttgagcct    3300
gggaagcaga gaggttgcgg taagccaaga ttgtacaact gcactccggc ctgggcgaca    3360
gagtgagaca ctgtctcaaa aaaaaaaaa aagaaaaaga aaagaaata agaaagaaa       3420 tcctttatgc aaaaggcaga gtaagtaatg gacaaatgtg gctcccttcc tagcacatct    3480
atttctggtt aacctcgatg atcccaaagg gtgaacctgg gaatggggag ttctgaggaa    3540
attctacaga aacagccttg tgaggtcctt tgtgggggc acgctgtgct gtgggggttc     3600
tggaaggaat ccgtgggagg ctgggaggaa gatctggctt gtcagcttcc ctaggaaaac    3660
cttcccctgg gctggccgca ggctgtaacc ggattcctgc tccacctctg catctggccc    3720
agggacctca tggcagggag gcccagcgcc tggccctttg ccctggacg ggtgggccc      3780 tgggtcatgg tggggtgggt ggggaggtca ggagggccat ggggagggg cgcggtgggg     3840 tgctttgccc tgagaacaca ggcctctggc accccggagc cccggcagc tgctggcgtc     3900 tgtcagccac cttgcgggc gcggccgggg gcctgctggc ccctacatct tcctgacagg    3960
cccctcttct gaggccagga aaaacaaca acagttcctc ccctcacggc aacccatttg     4020
ttagatgaag gccgggcacc agcaccttta acctcctcaa agtcagcgtt tccctgtcaa    4080
ggccccacag ggccagagac agagatggat ggaaggagct gtgtgtcgaa aaagccctgt    4140
ggcctcatga ggagagctct gttttcagga agggagggga ccccggtttc tgattgttgg    4200
ggagaataag gggaggaaga ggaaaagtgt gagtcacgag gaggtccccc aggggcgtgg    4260
```

-continued

```
gggggcccag gaggctttca gcctggccac acctgagcca tcacgtggaa cttgcggaat    4320
gtctcccatt gtgcgtggca ggcaggcgtg tacttggcag acagggctg cttctgtttg     4380 tggccacccc acccccttgt gcttggagag cagggtgtc agggcaaggc cctggacctg     4440
gaggcagaag acacgggttc aaggtgtgac cttgcctgtt accggctgtg tggtctcagg    4500
caaatcacac ccttctctga gcttcatttt tctcactggc aaaatggagt tgacagttcc    4560
ggcctcacct ggcggttagg aggataaatg aactgcatct gagaacagag ctggctgact    4620
ataaagggtg atgcatgtga ggaatagctt gtccttaact atgctgaacc actgggcagg    4680
acacagcaca atgtaggtga agacggctca tcccagcccc cagatacctt ctatggcaac    4740
ataacacaag ggtccaaatc atggccttgg gaattggggg cctgtgggtt caaacctcag    4800
ctctgttttt ttgtttttttg ttttgagacg gagtcttagc tctgttgccc aggctggagt    4860
gcagtggtgg gatctcggct caccgcaacc tctgcctccc aggttcaagc gattctcctg    4920
cctcagcctc ccgagtagct gggattacag gtgtctggca ccatacctag ctaattttg    4980 tattttagt agagatgggg tcttgccatg ttggccagac tggtttccaa ctccccacct    5040
caggtgatct gcccgccctg gcctcccaaa gtgctgggat tacgggcatg agccactgtg    5100
cctgacctca gctctgttat taataagcta aatggctttg agcgacttgc cttatcactt    5160
gagcctcagt ttcctcatct gtaaaatggg gataaacttc ttccgtccgc atgaggatgc    5220
tgagagacgt gagtgaggtg gtctatgaaa gctcttgtca tagcctggca tgcaggggta    5280
acatctggat gatgaagatg atgatacctg agatttttgc cttacagaca actccagaga    5340
gccctgtgaa atatttatat gccactgaac agggcacaag atgaagccat tagcctgcgc    5400
ttacatagta gaatgtgtga atcagatgag atgcttggtc tctagtaaga ccttaaggga    5460
tggacagaag acaggcagat tttggatatg gtatacgtgg ctgtgggcta gcgtgtttac    5520
tactgggcct gggatgtatt tggaatgtac acatgtgtcc tttgcttctc agaacacttt    5580
gaggcagcag agttactact gcctgccagc ctgcctcaca gggttttttg ttttgttttg    5640 ttttctttt ttttgagatg agtttcactc ttgttcccca ggctggagtg caatggtgtg    5700
atcttggctc actgcaacct ccacctactg ggttcaagcg attctcctgc ctcagccacc    5760
tgagtagctg ggattacagg tgcatgctac catgcccggc taatattttt tatttttatt    5820
tttatttatt tatttatttt tgagatggag tctcgctctg tcaccaggct ggagtgcagt    5880
ggtgcaatct cggctcactg caacctctgc ctcccaagtt taagtgattc tcttgcctca    5940
gcctcccaag tagctgggac tataggcacg cgccaccaca cccagccaat tttttgtact    6000
tttaatagag acgaggtttc actatattgg ctagggtggt cttgaactcc tgacctcagg    6060
tgatctgccc gcctcagcct ccaaaagtgc tggaattaca ggcatgagcc accgcgcctg    6120
gccctgacag ggctttgtaa tgctcaaata atatgatcca agggtcagag ttgagtaaac    6180
tatagaacat agtccttgca ttccacccca ggggcccaat aacgaggtct ttctctaaat    6240
ctcagaaaac actaagctaa gggaggtaag ttctgcagat gggttttctc tgtgtgtgtg    6300
tgtgtgtgtg tgtatacata tatataca cacacacata tatatata cacacatata        6360 tatacattta aacctttggt gctctacttg tctgctacca aaattgtagg cagatgactg     6420
aaaaatgtaa cacacagaat ggcctgcata gaaacctggc tcttggaagt catatgagtc    6480
agtttcctca actgtaaagt ggtggctcac tgtacagaca ctcagtaagc acccagcaaa    6540
tgaacacctt ccagggggttc tgtattggag tcagctgtat agaatgaaaa caaatgacaa    6600
aaggggaaac acacagagtt tattattctc ccccataaaa aaggccggag gtgacagtcc    6660
```

```
aagctgagat ggcctctccc ccaggcactg tctctctact ttgccccct gcggcacctt    6720 gttcagctgg catgtcagca ttccacacag cacgaaggag gaaggacaaa tggactctcc    6780
ccatctctct gcccactgcc cccctcccca aacccgtttt aaaaaataga tatgggggc     6840 cgggtgcgt  ggctcgtgcc tgtaacccca gcactttggg aggccgaggc gggtggatca    6900
cgaggtcagg agatcgagac catcctggct aacacggtga aaccccgtct ccactaaaaa    6960
tacaaaaaat tctccaggca tggtggtggc aggcgcctgt agtctcagct actctggagg    7020
ctgaggcagg agaatagcgt ganccgggag gcgtagcttg cagcaaggcg agattgcgcc    7080
actgcactcc aagcctaggc gacagagcga gactccatct caaaaaaaaa aaaaaaaaa     7140 aaatagacat gggggcctgg cgcggtggct cacgcccgta atcctagcac tttgggagtc    7200
cgaggtgggc ggatcacgag gtcaggggtt cgagaccagc ctggtcagcg tggtgaaaat    7260
ccatctctac taaaaatata aaaatcagct gggcgtggtg gcgcatggct gtagtcccaa    7320
ccactcagga ggctgaggca ggagaatctc ttgaacccgg gaggcggagc ttgcagcgag    7380
ccgagatcgt gccaccacac tccagcctgg gcgacagagg cgagactccg tctcaaaaaa    7440
aaaaaaaaaa tagacatagg gtcttgctat gttgcccagg ctggtcttaa actccttcct    7500
tgagtgattc tccaccttg  gcttcccaaa gtgctgggat tacaggagt gagacacagt     7560 gcccagcctc tctacatttt tttttttttt ttttaagaca gactctcact cagtccctca    7620
ggctggagtg cagtggtgtg atctcagctc actgcaatct ccacctccca ggttcaattg    7680
attctcctgc ctcagcctcc caagtagctg ggactacacg cctggctaat ttttgtattt    7740
ttagtagaga cagggttttg tcatgttggc caggctgatc tcaaactcct gacctcaaat    7800
catccacccg ccttggcctc ccaaagtcct gggattacag gcatgagcca ttgtgcccaa    7860
ccctccctgc cctgttttaa ggagggtcct gttcaacaat tactctacag accaattgcc    7920
cgcaactata tacttggcag tgaggaactg ctggggaggc tgggagattc agcctatagg    7980 cacccttggtg gccctaataa ctcttttatc ttcttcttct tccccatcag aacctgttct    8040
caaggaaaag agctaaggta ggctgccaga taaaatgctg aggtaagtct gttccagaaa    8100
atattgggac atagactaaa aaattgttgt ttgtttatct gaaactcaaa tttaactgag    8160
tgtcttcttt tcccctaaa  tctggcaatc ctaatccaag gctaaactca ttttcaggac    8220
gcaaaaggct ctggccttac cttttgagtc aggacgttgc actttgacag aaggctctgg    8280
aaggaaactt taagggagc  cttccagagg gaaatgcggt gttggggtag gtctgccttt    8340
ggctatgggc tttctggctg ccggagggnc cagggtccc  ccaggaaagc cttctgtgga    8400
nggtcttttg agagagacaa agcagagggg tggaggaagg gcggctcagg tggaaggagt    8460
gaggacaaag gtgagtgccc ctgggcagga agtgctgaaa gagagaagga gggaggccac    8520
caggcctggg cctggagcca gcctgggaga ctcccagccg cccacttctc ggggcctccc    8580
ttttccagcc ccttgctttc gaggcagcag tgccattatt tggggaaacc agctaaccag    8640
ataggacagc aaaccgggga tttatgtggt gtgggaacag ctcaggtttc cctccctgtt    8700
tacccagcag tatttttaa  aacagaaatc agcgtgtggg taaccgcagc tgtgagttac    8760
tagctctggc tgtgagggct ggggtggggg gagtctcttc agagccctct gtccactggc    8820 ctggagcta  ctgaaggaat gtgcctctcc ccatcccagg ccaggtggag aaggtggccc    8880
tgcggaagtt cccagatcac tgcccactc  acccttcccc tcccgacgaa ggccagcaca    8940
cctgggggag gtgtgatgat ggttcaaggt ctaaagcttt agagatcagt cagtttaggg    9000
```

-continued

```
gtcagaaccc atggagccag gcaagtaaac acaggttccc caagccagct gggagggaga    9060
cacctgggtg cctttgatgg gagaaagagg gggccaacag ctacttggca ctggccaatt    9120
ttcccttgca tgaacatggg cccagtgtaa ccaaccatat ctttccattt gtcaaaaaaa    9180
agccatattt ccagattttt tataggcaac ctgtcaactt ttaaatgttg gcaatgaatt    9240
caaaacactg ccattcaatt aaaagcagcc cagaacatgg cacgactggt tcttggaata    9300
ccaatctgca atctctgatc ttgtccaact ctctctgctc cccattttac agatcaggaa    9360
gctgaggccc agagaggcct agggacttag ccatggctgc agcagttgtt attgggaatg    9420
ccatgaggcc aggatgcctg ttatgtgttc tttgcccagc ctagcagttt ggctggcttg    9480
gctatgccag aggtctcacc atgcagttct caagtgcttc ctgagcatct ctcatttgca    9540
tagacatgac atttacaaac acatccatca tctacttgat tctggcaatg acaccgaggg    9600
agcagaactg gcattaatcc attttttta atggtgagaa cactgaggtt tggagaggct    9660
ggtgacctgc caaagtcaca gtcctagaaa gggctgcagc cagggcctcc aattacagat    9720
caagggtttt tccacccca aactcagtca tctcgtaaaa acgtcaggct ccttggggaa    9780
tacagcttga gatggataat caactcctcc taaaagggaa ccataaatgg atgagatact    9840
tgggtaaact gaatattctt tgtaacttaa agttaattga aaatccatag gttatcaatt    9900
ttccaagcag gagaataaaa tagaaggtat ttcaaagagc aattatagta ggcatggctt    9960
aatctttctt tgatgattct gaaggcattt caggggaatg taatgcctta gggcatcatt    10020
atgaacacca ataattactg tgtagggctg tgacgcaaat tctcatcaat ccctcctgg     10080
ctgtcggggt gttttcagag aggatcatgc agggagtgtg aacgtgtgcc tgtctgtttc    10140
ttgctgctct ctccgccttt gtcaatttca gggtgctgtt gtggaaaatg cagtgtccct    10200
ggaagggga ggtcacttaa ccttaatgag cttctgtttc tttattaaaa tggggtaatg      10260
cagactccta tactcactgt caaggttttg tggggctcag atgtcagtgt cagagcagga    10320
agaaacttta gatcatgata tgcaccagct tcattctgcc atggaaaaat ctgaggccca    10380
gagaggttag gagcctcgtc caaggtcacc cagccaggga gaggtgcta aacctgggt       10440
tttctgcttc ctaacctctt tcctgaatat aacactatgg aagaaaaaga tctggaggaa    10500
cggaaagatg aacacatgat tacacatgca acaatactg gggtctctct gatcagaaa       10560
ggtgtgatct tccagcctca ggagagggc catccaagtc ctggaggagg tgaacccctt     10620
agttcagggc tgggagtagc ctgggggcag cagagacact gctgtgaggt ttatagtttc    10680
atgactgtca gagcttttta aaatgtggta attttaagtg tgcagcctcc cagggtcttt    10740
cttcttttaa ttgaagaaat aaaccatctc cctaaggca tgcttggcga aggagaaagg     10800
caggtgcaag gctcacagag gagagcagca gcctagaagg gctctgtgtc atggggaagt    10860
aaaacatccc agaaacagag agcagaaggc cttgactgag ccccaggaga ggcaggacac    10920
caggggtgca cacccataaa cacacacata cacatgtatg tctcctccct ggagcctgag    10980
agtccctata tacagcaggt gcatgtgggc cacacatcac acaaaattga atacaggcag    11040
gctcagagca ccagcacaca cgtatgtcct tgacacccctt agagatacta ctaagcacgt   11100
gtgtgtacct gctcacccat atggcagagc ccctggatct gggcagaaat gccaaagcag    11160
gggcaggcgc gtgtgcgcgc acacacacac acacacacac acacacacac tagcacagcc    11220
acaaaagctc aatccacatc cagcattcct aacaacacac acacagctag acacgctagg    11280
agacacatca ggacaatgtt tccactcccg ctgccataca catatgcagg tccacattca    11340
ccagtggggt agggtagagt ctcatcagtc cagactcgca gacagctgga cacagaggtg    11400
```

```
atctctgaaa cccaatgtct acacactgtg gtctttgtta cacacacaca cacacacatt   11460
gaaatgatgt cctcagcctt tggttatttt tggtttcttc tgagctggag tttcactctt   11520
gttgcctagg ctagagtgca gtggcgtgat ctcagctcac tgcaacctcc acctcccggg   11580
ttcaagtgat tctcctgcct cagcctccca agtggttggg actacaggcg cccgccacca   11640
caccctacta attttgtat ttttagtgga aacagggttt caccatgttg gccaggctgg   11700
ccttgaactc ctgacctcag atgatccttc cgccttggcc tcccaaagtg ctgggattac   11760
aagcttgagc caccgcaccc ggccgagcct tcgggtattt tgaaagctga atgtgtggtt   11820
acattttctt ttcttttct tcttttttt ttgagacgga gtctctctct gtcaccaggc   11880
tggagtgcag tggcgcgatc ctggctcact gcaacctctg actcccggt tcaagtgatt   11940 ctcctgtctc agcctcctga gtagctagga ttacaggcat gcaccaccac gtccagctaa   12000
tttttgtatt tttagtagag ccagggtttc accatgttgg ccaggatggt ctccatctcc   12060
tcaaatcgtc atccgcccgc cttggcctcc cgaagtgctg ggattacagg cgtgagccac   12120
agtgcccggc ctacgttttc aaacagcaat agcattcgcc tcctctgtca gtttaacccc   12180
catcacaact cccactttg gcacctaaac agttaatttc ccagttcatg ggccttcaaa   12240
gtcctgctct agtctctgga ggaactttca cctacagagg aaggtgtaag ggaaactagt   12300
tcatggattt aagtagaaac attttaggtg tagctttcac atacagagga gtgagaaaaa   12360
actgattcat ggatttagat ggaaacattg tagtatgaac ccagcggagg gtctgggagc   12420
gccttctggt ggtgagaatt agaaccgcag cactttctgc aatgtgccca ggccagaaag   12480
ctctaccttc tgataggacc cacttctgac cctagaatgg gggaactgat ggaggtgtca   12540
agccactgtg gtcccacagc tgcatgcagg cacagggat aggaagagag ctacctacag   12600
gttactaaac cattccctt taaaacagca ccaggcttat gtctactctg cgcttccatt   12660
ttctaggttt taagtggaag atatgtgaac acccagtggg ctggatggct gtccctgcta   12720
caagtctgtg atgtctccgt ccagtggcag agctggaagg caggtgctgt cggggctgca   12780
tctgccttgt tcaccagcat aggcctaaaa ccatggaggg ggtgctttgg cttagatccc   12840
cacttggcct gtgtgtgtaa gaggctctca ggcaccttaa tgctacatca ccaaccaaac   12900
ctcctgatga ttctttagg ttctccgttt ccaggcagat tcacttctgt agatttattt   12960
atttattttt gagacagggt ctggctctgt cccgcaggct ggagtacagt gatgcaatct   13020
cggctcactg tagccttgac ctcaacttca agtgatcctc caacctcagc ctcccagtat   13080
gagggaccac agtgtgcac catcacacct ggctaattt tgtactttt gtagagacgg   13140 ggtctcacca tgttgcccag ctggtctcaa actcctaggc tcaagcgatc caccaacctt   13200
ggcctctgaa atgctgggat tccaggtgtg aagcaccgcg cccagtccct gacttctgta   13260
gacgtttgta ttgtttacat ctactgtgtg caatgtacga gatgcagtca ggtgtctgga   13320
tggaccaggg gatctggcat cttatagact tgggtttgaa ccccaactga gccatttact   13380
ggctgggtga ctttgggtga gttcttaaac ctctctgacc cttaaggtgg taacagtatc   13440
accagtgaag ttggtgcaca cagcagggcc caaactgaca tctcacagca cccagcaggt   13500
cactgtgggc atgataggat gatgggtcac tgtgccagcc ctgaaggagt tcaagtccag   13560 atagggaag gtggtggacc agacccagac agagattctg agtcgctgct gagactgggt   13620
gagggtagtg ggtacatggg aggacatata gcccggcagc ccagggctgg agtccacact   13680
caggttgggg cagcctggtc tgcctctcct gcaggagact tttccaggca ggcttgtccc   13740
```

-continued

```
tccagaatgc acgaatcaaa tcctctcagg atcagtctca ttttcctcgt gctgggggag    13800
caggctactc acagaagatg ttgttgcaaa tgtaagaatc acatgtcgat ccacaaactg    13860
gcattgagca gctacctagg agatcaaaga aactcttact ttgggagctc ctgccagggc    13920
tctttgggag gtctggctag ctctggagga agagaatgaa cttggggagg gcgtggaaca    13980
gatgaggacg caggcactgc cattcaaaga ggagaggtct cccggacagg gctggcctgg    14040
gcaggcccag ggagggtggg gctggagcag ggacttgaaa aagggagagg gctcaggaga    14100
ctcagaggag gaggaaagtg tgtgagcagt aggcagggtg tgtgtgtgtg tgtgtgtgtg    14160
tgtgtgtgtg tgtgcacgcg cgcgcatgca ggcctgtgta gggctgggaa agaacaaagc    14220
aaaagggtgc acaaggcatc cagaagccag ggcaatgcag aacaggaaca aagcagtttg    14280
gctcaagggg aaagttctga tggaaagcaa ggaaagagaa tgttagaagg gctgagagcc    14340
agaatgccca gtatgggta cagagggcaa cagaggggct gatgttggtg gcgaggtggg    14400
gaggagcatt tcacagggaa ctgggcagct ccaaggatgg gctggaggag ggacggtcct    14460 aaaggggtg gtgggagaca ggcagttagt gatgggggga gagaaatgct ctgagggggg    14520
ctgctgtagg cagggagggg caggtagcag gaggcagagg gttgagcctg cagaagcccg    14580
gagcagtctg tagcttttcta atgcttccta gggaattctg ctgctgagta gccatgggtt    14640
caacaggtct ctaggatttg ccttgaatta ctgccctgag gccccctaag tctgggtct    14700 cataaattca gcggggaggg cacacctgtg tctgagtctg agcagcccag agcccccagt    14760
gttgtcagtg aacagctcac tgaacttgca gagcaattaa atcccagggc agaagaaaga    14820
gcaggagggc agggtggccc ccagctccct cccatcccgg gtttggggag agacacctct    14880
ggcctgagac tcctcgtggc ctctaacaag tcttgctctc tctctctttt ttttttttt    14940 ttaaattatt gtctcccgcc ctccttcctt cttcttggga atcagaaaag aaacctcaat    15000
gcctggcttt gccctccct ggctgtggtc aagccatgtg acatttagac atttcagagc    15060
ctcctgactc ctgaggctgg agacagcatg aagccaaatg ggcttggcaa acagaagaga    15120
ggggcagtta acattctctg caatgctctc ttacttcccg tttaaacacc cctcctactc    15180
ggacacagac ccccaacccc tgtgccattg tgctcactcc caccttggag gggtcaggct    15240
gtggtgaaag gtcaaggtga aaagtcatga tgatcctatt gctgccacct ccctgggtg     15300 agcaagattc tgtggtggct ccagctctcc catggcagtc cacacagagg ctgttccagg    15360
ttctggagag gtcacttggt gtgacctggg aatctgcatc ttttctctgc caaagcagag    15420
ggcattgcag caaccacacc tgggtcccag tcctcaacaa agtccctcca gctcccgctg    15480
ctgtctgcaa ggtttggtca tctgtccctg cattggagaa gagtttgcac tgtgaatctt    15540
gcctccacca gggaaggctg gtaaaagtcc ctgccccggg ggccctcatt gctccagggt    15600
gcatctgggg gccagacctg tggaccctca cccttgagcc tcattttgtt cctcttagaa    15660
caaagccatt tctggtaaat aggtttgatg ggtttggcag cagggaaggc acagaacctt    15720
tcacgattag caggctcatg acaatttctc tttaggcaag agagaaggtt gaggaggaaa    15780
gactggcagg gcttggagag ctggaaagga agaaaggccc tacaggcctg gggatcccat    15840
ctctgaccac cgaccccagc ccccaactct catagactct gatttgatat tcttattac    15900 caaagaagct gcatgtattt gcatatcaat tctctttccc atatcgacac gcaggaggc     15960 ttcttcgttt tggatcaacc agagatcacc aatgtctgca gggtgctcag ccctggtac     16020 cttggtcact ctaggcagcc tcctagatgt gcctcttaag ataggttttc tgaaatggga    16080
gaggaccacg ccccgccccc caccatggac tctggagtct gcggcgcaca aatcctgcga    16140
```

```
ttttacagat ggggaaacag aggcacggag aaagtctcag ctttcccacg gcccactggg    16200
accagaaccc aggtcgcagg acggggacag ccacctcctt tttctctcct tgcaaccagc    16260
ctgagctcgc tcagcgggtg ggggctgccg ctatccagag caccctgttt ctggatgcaa    16320
aataaaggcc caggcagtgt ttggccctcc tctgcccaca gactttggct ccagggcagt    16380
ctccgagaga gaagccttgg gtcccactgg tccgagctct gcgtgctgag tctagaggct    16440
gcagtctcta agccgaaact agcccaggcc tcacagccgc cttccgccg gtctcccact     16500 gccttggcgg ggcgctggcg ccctctgctg gccaagtctc gctctgcgcg caaacgcccc    16560
agaaatcagc cggaagttcc ctggggcccc acaggagtga ggacccacct ggattcactt    16620
tgtcattttt tttagctgc atgaccttaa gaaagctaat gaacctcaga gcactacctg      16680
tgaagtggaa ataatagcgc ctacacttca gggtcggtgt aaggattgca tagaataccg    16740
tatagaaagc acccagcaca ttgtaggtat gtttaatggt agcgattatt aataatgccc    16800
aactcacatg gtgagatgag atctgagaag cctccttata aaggtaaatg ataaccaagt    16860
cttgttgcaa ggcagctggt gtgttactaa tacatcatga ggtggtgggc cctctgggga    16920
ctgtcaggag acagcctctg ttttattagg aaataaaaca gaatctggtc tgctccagtt    16980
ttcttccttt tatttactgc attagaaaac tttcatttta tttattgcct attctggggg    17040
ttgagggtga ggggaaggca tgactccagc caggtaggat acaaaagtat ctcacccccc    17100 aggagggtt tgaggaccgg ccctccggct tttagaaag ggcagctggc ttctgttgct       17160
aacgatttgg atttggcttt taacagaata tcaaggtgaa agtgaaagga gcttttcact    17220
ccttggagag tcaagagggt gtggggtggg acctccaggg gaatgaagag tgagcgaggg    17280
tgctgggggg atcccagacc taggaatcag atctgggaa ggggtctgca agacccctcc      17340
atgagtcaag aaaagccggt gggtggatgg tgagaaggac cagtgaagac actgtttgct    17400
ggagttgtcc cagccagtgg ctatgactga gactgtccca tggcgtgtgc ccagggtcct    17460
gccattggat gatgggacat tctttttttt ttttttttt ttgagacgga gtctcgctct       17520
gtcatccaga gctggagtgc agtggcgcaa tatcaaagtc gctgcagcct ccacctcccg     17580
ggttcaagca attctcctgc ctcagcctcc caagtagctg ggattacagg cgtgggccac    17640
cacatctggc taattttgt attttagta gagatggagt ttctactcca tcaggctggt         17700
ctccaacttc tggcctcaag tgatctgctg cctcggcctc ccaaagtgct gggattacag    17760
acgtgagtca ctgtgcctgg cctggatgga acattctgct ctttctccat ctgctgccta    17820
cccatgatgt cttgggactc ctagaaccct aaaggaagcc cctggacacg caggaaggtg    17880
tggagaggag ttctcatact tgcacttggg aggagggctc aggagaaaca gaggctggca    17940 acacccctc acacactggt cctctggagg gccagtgtct acagacactg tggactgagt      18000
ccacagagag gaaagggtcc tgccttcatc agaactgctc agcaagcagt tccatcccag    18060
ggggtcctgc gaggtaaggg aggggcagct agctaggtga ggggctgaga gagtggggag    18120
gggaaagagg gaagaagaga gtgagaggga gaggagggga ctgagccgat tctcagctcc    18180
ttgaccgttt gctgagctct gtctgagtgg acagatggtc ccaagtcagg ccacaccaga    18240
gtggcctttc tgctccccta caccctgcat tcctcaacat tgctggcccc ggagagactt    18300
tccttcagag aagcaaatgg ctggggaatg gtgaaagaca ctgcagagaa agaaagcac    18360 agcctgctgc cctgggaatt aacatgattt aggagacctg caggtcaccc cctcatgact    18420
aaaagccatc ctggaatgaa ggtctgtggc tatttctagg caaaactgtc tgataagata    18480
```

-continued

| | | | | |
|---|---|---|---|---|
| aaatagctca | actcctgacc | attaagtcgt | gaaggccatg | gccatcgtaa atctcatctt | 18540 |
| tccggccctc | tggcctgcat | gcagtgcagc | ccagccagtc | ggtggcagcc accttggtag | 18600 |
| gaagggccct | catcctcctg | gctgtgcccc | aaggactggg | caggcttcgg tgccaagggt | 18660 |
| agtgcgagca | cttgaaagcc | gccctgtatg | tttattgttt | tccccaggtg atccagaatt | 18720 |
| actcccgaac | tctaccagct | gaaatcctcc | tcaactcaca | tcagacaaga cggccctgcc | 18780 |
| acttacctgt | cagatcactt | tgggcaggta | agctcatttt | cctgaatctt tacttccaca | 18840 |
| ccttaaaatg | tgagcaatac | tatctccctg | gcaaggttgt | ttgtgagggt aaaatgaaac | 18900 |
| aataatcacg | ggtgcatcct | ggagctcttt | cttacaaggc | gtgcccccaa atctgtcccc | 18960 |
| tctttctgag | gatgcccttc | ccctattgtc | tccctggcca | tttcctaccc attctcaagg | 19020 |
| gccatgatct | cagggagttc | tcctgactca | cccaggcata | ttggatctcc tacgtactgc | 19080 |
| tacgactgca | cacaggtgca | ggaaatggct | gtttgctttg | cgtttgagga acttggaaag | 19140 |
| ggagacgtgg | tagggaaagt | agtggttagg | ggcactttca | gactgaagga tgtgggttgg | 19200 |
| ggaatacggg | attcttggag | ttgaggacgc | cgcttctctc | gtctctagct aatgtgagaa | 19260 |
| agacccttct | ggacactaag | cctgcaattc | cactggtggc | taccaggtgt ccgtggtgtc | 19320 |
| ctggggcggg | tgtaatgaga | gcgggagcct | gtgaaaccaa | agcattgtt tttataaatt | 19380 |
| cagcactctt | caatccctat | taataaggtt | agcggtgcag | ttcttgcgtc tcctgccctg | 19440 |
| cctcaccttg | caatcatatt | cattggcatt | cctttcttcc | aagaacccac ctaggaggcc | 19500 |
| ttgcaggaga | tatctctggt | gctggctgtt | cctgcagtct | gaaaagccag ttaagataca | 19560 |
| aatatgtgag | aggacactgc | ttgaatctga | tttcattttt | taaaaagttt aattattcac | 19620 |
| agactttgct | tctttctgac | tagtaatgtg | acacctgtga | ctcagttcaa gatggtgtgt | 19680 |
| ggtgaccttg | cagttgagaa | gcactgagcg | ctatagccat | gccaagaagg ttgccctcct | 19740 |
| gggaccagca | aaaattccat | ccaggggggcc | atctctgtca | ggcttgtcct gactatcttt | 19800 |
| ttggagaggc | ggcagagtgg | agtggttaaa | agcatgattc | tggagcccag ctacctggga | 19860 |
| gcaaagctcg | tctctaccgc | ttaccagctc | tgagagctta | ggcaagtgac ctattctctc | 19920 |
| tgtgcctctg | agttttcatc | tgtgaaatgg | gagtaacaat | agtcctgtct cacagggttg | 19980 |
| ctgggaggct | tgaatgagtt | aatgtccatg | gggtgctgaa | tcagtgcctg gcatacggtg | 20040 |
| aaggccatgt | gagcagtaaa | tattattatt | attagaaagg | ttggctgggc gtggtggctc | 20100 |
| acacctgtaa | tcccagcact | ttgggaggct | gaggtgggca | gattacgagg tcaagagtta | 20160 |
| gagaccagcc | tggccaacat | ggtgaaaccc | catctctact | aaaaatacaa aagacattag | 20220 |
| ccggtatagt | ggtgcgtgct | tgtagtccca | gctactcagg | aggctaaggc agaaggatcg | 20280 |
| cttgaacccg | ggaggcagag | gtttcagtga | gctgagatca | cgccactgca ctccagcctg | 20340 |
| ggcaacagag | tgagactcca | tctcaaaaaa | aaaaaaaaa | agaaagaaag aaagaaaaaa | 20400 |
| agaaaaggtc | ccaacctact | cacttattgt | tcacttgcat | caaatgctag gttcagtgta | 20460 |
| ttgttcttgt | aagattagaa | atggagagat | gggtcagaag | gggttggtca aaatagacct | 20520 |
| ctcaacccaa | gcagacaggg | ctggcttcat | ggccgggcaa | ccatgcagga cccagggctc | 20580 |
| taagataaga | aaggcacgta | gtttaatgct | ttgctgtccc | atcttgatac tgttttttt | 20640 |
| ttctttttt | tttggaaatg | gagtttcact | attgtcaccc | aagataaagt acaatggcgt | 20700 |
| gatctcagct | cactgcaatc | tctgcctcct | gggttcaagc | aattctcctg cttcagctcc | 20760 |
| ttgagtagct | gggattacag | gcatgtacca | ccacactcag | ctaattttg tatttttagt | 20820 |
| agagacgggg | tttcaccatg | ttggccaggc | tggctggtct | cgaactcctg atcgcaggtg | 20880 |

-continued

```
atccacccac ctcggcccca caaagtgctg ggattacagg catgaaccac cgtgcctagc      20940
tgatattctt aatttatgaa ggaagggccc caaattttca ttttgcactg ggcccacaaa      21000
taacgtagca ggtcccacaa acaaattcgt ctagattcag agggcccctt gccttcctcc      21060
tctgctcaca ttcgttcctt tctcccatca caggcgggta ccctaccttg ggggatttgc      21120
cccagaataa gccttttttt tcccttctaa cattttaatg aaaaatttca agtgtatagc      21180
aatgttgaaa agattttata gtgagcaccc atacacctgc cacccaaagt ctaccattaa      21240
tgtcttctgg acttactttt gccgtcttat tcatactctg cctggactgt cctcagctac      21300
aggactcaca tctcttgccg acagctctaa ggcttccagt cctgctgtct ggaccaagaa      21360
aggcttcctg ggctctgagt gtcaaatggc ggccttcaag gaaggggaat ggtggaaaag      21420
gccgtggggg gttttggaga aattgctagg gaaagactgg caccagagtt ccaccagccc      21480
aggcaatggg gggtacagaa cccataagat gagttctaga aaagcaagga aggtttcgtt      21540
ctggagtttg tggactgagg tttccatttg tgactaggat tctcattggt tccttatgta      21600
gtttcttacg ccctgcatag tcttctaagc atttctcaca gacgtggtct gggggcgaac      21660
accagcagcc ctgagaggtg gctaaagagg agattcttct ctccacttca catcgtagga      21720
aactgagtct cagaggttcc ttccctggcc tgcccacaac cccagggcta aaagaggcag      21780
accaagccca gggccttgaa ccccaacaat gggcctcttt cttttgatcc catgataggg      21840
gtgcaaaagc attgcattcc cctgggtaat ttgaagaaaa aacccaaaaa actccaactt      21900
tgtctccagg aaaaagaggg tgtctgggct atgatttacc tctgagggtg tggttgcact      21960
gagcgtgatc acacttcaaa gggttagatc tcatttctct gcctttctag cttgggccca      22020
gggctcagaa atgtgtggac tccctcacag cccctcccag catccctgcc ccctcccaac      22080
tgccttgggc aggtgacacc tgtattattg ctaagggtta aaaagccccc aaatcaataa      22140
aacccattaa tgagtgttgg tacctcgaag gctacagata aatcccttct actcagtgag      22200
ttcaatccca taaacagct ctccccttc aatcctagca ttcatttgat agaaaatgtg      22260
gagaaatttt aaaaaggtga cttactaatt gcctgtaaaa taaaaggcag atggaagctt      22320
tattacagtt gaaggaagtc gggaatatta aggtaaaatg tcaaataaca attgattttc      22380
cttagacata aaggggcgat ttatggcttc ctagttacta caaacgagaa attatttgaa      22440
gttctgaaaa gtatgaggag aaataaagat taaatagaag atgaaatcat agggatttct      22500
ctgggaggtg acttcagtgc ccctggggac tagaattcat gtggccagtg gcctagccag      22560
ctggggcttg gcagtttcaa gatttagagg caaggtgtct ctgaggagcg gggaagtggc      22620
tgtttgcttt gtgtctgagg aactaggaaa gaaagatgaa gatagggaaa gttgtggtta      22680
gggccaattt cagactgagg gatgtgggat tagggggattc ttgtggatgg gcctatagct      22740
ctgcttcctg actagcagat actggggatc tggggaaggg aagggtgagc tgcctttcct      22800
gggacttcga tggcatcctt acagtcaggg gacactgtcc ttgctgggtc ccggacatca      22860
gtgtctatgt atccctgcaa gccacagcac tatccaggcc ctctggtggc tttgcttggt      22920
ctgggccaac ctggtctcca cactgacagt caaagacgag gagaggaaaa agaactcacg      22980
gctaggcgtg gtggctcctg cctgtaattc cagcactttg agaggccgag gcgggtggat      23040
cccttgagcc caggagtttg agaccagcct gggcaacatg gcgaaatccc gtctctaca      23100 aaaaatagag aacaattacc caggaatggt ggtactctgg aggttgaggt gggagatgg      23160 cttgagctcg ggaggttgag gctacagtga gctgtgattg tgccaccgca ctccagcatg      23220
```

-continued

| | |
|---|---|
| ggcgacagag caagacactg tctcaaaaaa aaggctcatt tccaggctgc caggcttatg | 23280 |
| ttagcctggg gtcccgcagg agctgacctg agacaagtac ttgagggcaa gttgtttgtt | 23340 |
| tgagggatgc tcacaggaag ctccagtagg agggtaggga ggtgacccag ggaaggaagg | 23400 |
| cagcttacag gggcgtgttg tcaggaaggg caccccggcg ggtgacggaa gcttaatttt | 23460 |
| gctgggaaac tcaggagcca gcatggaacc tgcacctcag agttatccca ctggaaggat | 23520 |
| gagggagcgg gtacttatac accaactcca tccccgtcct ttgttaaggc tgctggatgg | 23580 |
| agtgggtggg acactcattc ttcagcactc ccaggggccc tcaggctgtc agaagttagg | 23640 |
| tccgttgggc tccaggatga ggggaccccc agaagatgcg ggagggcgtc cgcagcatct | 23700 |
| gcctctgtgc tttccctgtt tatctgaatc ctcataattc ccgccacatg cagatcagag | 23760 |
| cccccagctt tatggaagag aacacaggtt tggagaagat aaagagcatt cccacaacta | 23820 |
| ggaggtgggg aaagctagga gttcagccca gagctccctg acttcaaagt ccattctctt | 23880 |
| tctacttcct gattttttt tttttttttt tttttgaga cggagtttca ctctgttgtc | 23940 |
| taggctgggt tgcagtggca caaacttggc tcactgcagt ctctgcctcc tgggttcaag | 24000 |
| caattctcct gcctcagcct ctcgagtagc tgggactaca ggcgcccgct accatgcctg | 24060 |
| gctaattttt tgtgttttta atagagacag ggtttcaccg tgttggccag ctggtctcg | 24120 |
| aactcctgac ctcaggtgat ccgcttgcct tggcctccca aagtgctggg attacaagca | 24180 |
| cgagccactg tgctcggcct acttcctgat ttttgtataa gacacatccc agcagcatgg | 24240 |
| tagactgaag actcctgggc ccactctcag agattctgct ctggcaagga tgtgtttatt | 24300 |
| ggtgagaggg gtgtccagga atacgtgcct tttttttttt ttctagagac agggtctcgt | 24360 |
| tgtccaggct ggagtgcagt ggtgcaatca tagcttactg caatctcaaa cttctgggtt | 24420 |
| cgagcgatcc tcctatctca gcctcctaag tagctgggac tacaggtgca cgccaccatg | 24480 |
| tctggctaat tttaaattt tttctggagt tggggtcttg tgatgttgcc caggctgatc | 24540 |
| tttaacttca ggtctcaaga gatcctccca ccttggcctc ccaaattttt gggattacag | 24600 |
| ccatgagcca ctatgcccaa ctagaatatg cactttttt tttttgagac cgagttttgc | 24660 |
| tcttgttgcc caggctggag tataatggtg cgatctcggc tcaccgcaac ctcccctcc | 24720 |
| caggtccaag cgattcttct gcctcagcct cctgaggagc tgggattaca ggcatgtgcc | 24780 |
| accataccag gctaattttg tatttttagt agagatgggg tttcttcgtg ttggtcaggc | 24840 |
| tggtcttgaa ctcctgacct caggtgatca gcccgcctg ctttggcctc ccaaagtgct | 24900 |
| aggattacag gcatgagcca ccaagcctga ccttttttt tttttttgag acagagtctt | 24960 |
| gctttgtcac ccaggctgga gtgcagtggc acgatctcgg ctcactgcaa gctctgcctc | 25020 |
| ccaggttcat gccattctcc tgcctcaggc tcccaagtag ctgggactac aggcacttgc | 25080 |
| caccacgccc ggctaatttt ttgtattttt agtagagatg gggtttcacc gtgttagcca | 25140 |
| ggatggtctt gatttcctga cctcgtgatc cacctgcctt ggcctcccaa agtgctggga | 25200 |
| ttataggcgt gagccaccgt gcccggcctt tttttttt tttttttttt ttgagacagg | 25260 |
| atcttgcttg gttgcccagg ctggagtgca gtggcctgat tacagctcac tgcagcctca | 25320 |
| atctcctgga ctcaagcaat cctctcacct cagcctcttg agtagctggg accacaggtg | 25380 |
| tgtgctacca cacccagata atttttgtgc ttttgtaga cagggtttt cgacatgttg | 25440 |
| cccaggccgg actaaaattc ctgggctcaa gtgatcctcc tgcctcagct tcccaaagtg | 25500 |
| ctgggattac aggtatgtgc catcgtcacc agccagaata tgcattttct ttttttcaga | 25560 |
| cggggtctca ctctgttgcc caggctggag tgcagtggtg tgatctcagc tcactgcaac | 25620 |

```
ctctgccttc tgagttcaag cgattctcct gcctcagcct cccaagcagc taggattaca      25680
ggtgtctgcc acaacacccg ctaattttt  gcattttag  taaagatggg gtttcaccat      25740
gttggtcagg ctgatcacaa actcccgact gcaagtgatc cgcttacctc ggcctcccaa      25800
agtgttagga ttacaggcat gagccattgt gcctggccga atatgcactt ttaataagca      25860
tcagccaggc taggcaggcc gggggccaca ctcgagaaca tttgcaccac agccactggc      25920
tacctgcccc ttttccata  aggttccact gccctctctc ccctctatct gggtctgttc      25980
ttcaggttct tccctgggag ctctctgagt gacataactg tccccaagtg ctgggagatg      26040
gagagaggaa tcaccagact ggagcaggcc cccagagcgg agatgggaag gggaggctgg      26100
tgttctgagg ctcccgaggc agtgagaggt gaccggaggc agtgagaggt gaccgaagac      26160
agtggctgag aaccagggag gggctgcggg aaaaagccct gggtgcaagt cgctctttcc      26220
ttagcgtctt tgagaggagg gatggggaaa ggtgaggtac tagggaaaac catctggaag      26280
gaggtcaggc tgcagaaaag ctgcaggagt ctggggact  aagaaaacag tgggagaccc      26340
cgctgcagcc cagcacgtga gggtgagaac gtcatgaatg agggaagagc aggcagggg      26400 tggtggcctt gtggcctctg gagaggagga gccacatgac tctgggtga  tctggggtga      26460 ccctcagggt aagggtacct ccctagcact gagtacagag ggaagcctac actgccaggt      26520
gcagtttccc tggcaatgct tctccttcta acactatgtg agtttcctag tgctgctgta      26580
acaaactgcc ataaaccaag tggcttcaga gaacacagac ggactatgac agttgtggag      26640
ggaagaagtt tgaaaagcgg ggtgcccgca ggctgcagtg cttctgcagg ctccagggag      26700
aatctggtcc ttgcctcttc cagcctctag agcctgccgc actccttggc tcatggcccc      26760
gtgtcattgt agcctctgct tctgccatca catctcctcc tctgcctctc ctgcctccct      26820 ctgtcccttta taagaacgct tttgagtata ttggacccat ctggatagtc caggataaat      26880
ccctccatcc tcatatcctt aatttaatca cacctggaag gttccctttg ccacataagg      26940
taacatattc acattgggac agttagggga ttgggatgtg acatcttttt gaggtgggaa      27000
gaaggagctg gggttctttt taacatttt  ttgagacagg gtctctgtca cctaggctgg      27060
agtgcagtgg tgtgattgag actcactgca gcagcctcaa cctcctgggc tcaagtgatc      27120
ctcccacctc agcttcctga gtagctggga ctacaggtgt gcaccaccat gcccagatga      27180 ttttgtatt  attttaatat tttgtacaca tggaggtctt ttaatgctgc ccaggctgga      27240
ctcaaactcc tgggctcaag caatcctccc gtcttagcct cccaaagtgc tgggattaca      27300
ggtgtgtgcc accagaccca gcccggacct ggggttcctg tctcatgtca gccttagcaa      27360
tctgggtgac cctgggcaag gcctatcccc tctctgggcc tttgtttctc cacctgtgca      27420
atgaggctgt tccctctggc tccttcactc tgagtttttc agttgggaga atatcttggc      27480
agggagcaga ggtcggcggg ggtggttgtc attccatttc agggcctctc agagtcctgc      27540
cgtggtgtgc actgtgtgtg tgtttaattt tctacatttg gatgtgatcc taatccaata      27600
aatgcttagg agacttctat agaatagatt aatttttact agaaaaaaat ataattggct      27660
gatgttaagg ctactgccct gacaaatctg ccttggccat atatctgaga aggtaaaaga      27720
cccgctacgc ttgcacataa atatgccatc ttccccacag gccctggaga agcacccgg       27780 ggaggtttcc cttggtgatt tattcttcat taataagctc tatgctatat taggatcaga      27840
tttatgactc tgccttttcta atatttctga catttcatct gaaagaatt  acaaatgaaa      27900 tcttgaaact ttgccacttc tccctgctag tgctctggca ctctgtgtcc aagggagat       27960
```

-continued

```
ggtgggctgg ggagacccca agaagcaggg acagaggcat gtttctcagg gaaaggagcg    28020
atcagcttga ctttgggaga gctttattca gtttgcaagc agcttgggag gtgagcggtt    28080
caggcgagaa ggctgcagac cagaccacaa gcccagcagc agcagtgatg cctgtaacat    28140
gtatgagatg gtggcaggca cattcattca ttcaacagct atttgttaag cactttactg    28200
tgtgccaaac actgtgctgc ttggtgcttg ggatacagga agaataaaaa gtgaagcagt    28260
gatgaagatc ttggccttca tgcatatggt gttctagcag aggtagggga gtgtcaagca    28320
ctgatgaatg aaaatcctga ataggtaaaa tatatcatat gttcacacgt ggtaagggct    28380
atggcaaaac agaaacaaac cctccacaca gggaaaaggg aaccaagagt gccgggtggt    28440
caagttgcaa tgttaattaa gaaagcactt caactcatca actcaaggaa ccgtattatc    28500
cccattttac agatgaggac ggaggctcag cgtggattag gagctacaca aagacacaaa    28560
gggaactttg cacaacttga aagtttgcaa agtgccgtct gagccattag tctcccttct    28620
ccccactgac tgccctacca caatcacatg gggaccataa aaatactgtt gcctgggtcc    28680
cgctcccctg aggctttgat tcaattggtt tggatgcagc ctgggacttg gcatgtgact    28740
cttgtggtgc caggactaag aatcttgtgt gaactcccag cacagcctct caggcctcta    28800
ttttctcacc tgcaagatgt gggtaaaaat attcaccctg tactgcaaga ggatgtcagg    28860
agtgaaggca gaaacacagc accagccctc caggacccce aaccectccc ccaccccaat    28920 ccttcaccce tgttgtacct tctgacctca agtggctctc gattatttca ctcccacagg    28980
ccactggctc agaggtatag agctcacctg tggcagatgg agatgcggat ctgaggcttc    29040
tgatgctgcc acaccagcg gcgccccca aattccgggc ccctggatga catctggtct    29100
gttcctgcag catcagagca caatagagcc agccaccagt cccagccctg cctgcatccc    29160
atccattcct gggtgcctaa ccccgaggat cccctggcag tatgatgcgg acctgtcttg    29220
gatcccaggg atatgctggc cacggggagg agccggaaac caaccttgt gtcactgtgt    29280 agtgacaagt gcctttggag gtcacaatag ccagtggtga tttctaccac tgcccccagc    29340
agccaaggtg gcagaggagc cctgtcagtc acccccattc tgttcatggt ctcacggtgg    29400
gctccacatg ggggtggca gccctctccc ccaccccacc cgacccctt cgacagatag    29460 ggtaatacaa atacaaataa caccaaaaga ttgagttgct gggcagaaag ggaccaaagg    29520
ccagtgtgtg tgtgaggggt ggggggcaggg caggagagga gcagcaaaag gctgtgaccg    29580
cctggctgag cactggatac tcactgaagg gcagggaggc ttcctggaga aggagacctg    29640 gcagggctg agggagtgat gccaggcatg ggggtttgga gggaccccag gcatggcatg    29700
cctccattcc tccctgtgct atccactcta tataaggggt gctgtgcagg gagacagctt    29760
gcatccaagc agggaggcag ggaggatgag aggcagagag gagcccagct gggttgatgg    29820
aaagtctggg aaatgcagga aatccaggag ggggagaatg attccaagct gtggcctgtg    29880
atgggccttg aaaccaggtg taggcacttg gatctgatcg ctggggagcc agagctgctt    29940
cctgagcagc agaagggcag gatgcgaatc agactagggg cagtgggagg aactgagagg    30000
cctcaggtca ccggagaaaa tgcacagggc cgggaggcag agatgctcct gttttcttgc    30060 tctgggctc aggacagtca gtcacccctga gcttcagact cagctcactc attttgcaga    30120
gatcctgacg gcgatgcttc aggatgatct gggaagagtc aatgaggtaa aatatgtgaa    30180
atatgccttg aaaactacaa accacagcac atgttctgtt tttgcttctg cttgatggac    30240
tcagtgagat ggtgggggaca agaattagag aagcccatga ggaggccaag ggcaccaaa    30300 tagacccacc aaggaccagt ggggacttag agaaaggatg agtcagagag aaatgacagg    30360
```

```
agcagaaggc aggccttgta tggaggatga aggtgaagat catacaccat taaacttgag   30420
aaagaggcgg gaggagctgc catttcttga gtctactgga tgccagcagt agtgctgggc   30480
aagggcttaa caggtgggga aatcgaggca cagagaggtt aagtagcttg cctaagatca   30540
cccagttagt aagtagcaga gcctggcagc ttaactccaa agtctttgta ctaaagccag   30600
attttccaaa tttgcccaac tgtaagaatc acctgggcct gtaatcctag cattttggga   30660
ggctgaggtg ggtggatcac ctgaggtcag gagtttgaga ccagcctggc caacatggtg   30720
aaaccctgtc tctactaaaa atacaaacaa ttagccgggc gtggtggcag gtgcctgtaa   30780
tcctgtaatc ccagctactt gggaggctga ggcaggagaa ttgcttgaac cccaaaggtg   30840
gaggttgcag tgagctgaga ttgcgccatc gcactccagc ctgggcaaca agagagaaac   30900
gccatctcaa aaaataaaa gcccgggagt ttattacaga tgcatattcc caggcacctc   30960
ctacggaggt tttgagttag tgagtccaag gccttctgcc tcttcccaat gtattcatta   31020
tgcaccatca ttactcttgt tcagatacaa tgtgagtgat agcttgtctc tggcagcaca   31080
gcagccacac ccaaccaatc cagacctcag tcatgagggt gccaatcaca gctaacattt   31140
ttttttttga cacggagtct tgctctgtcg cccaggctgg agtgcagtgg cacgatcttg   31200
gttcactgca gcctctgcct cctgggttca agcgattctc ctgcctcagc ctcctaagta   31260
gctgggatta caggcacctg ccaccatgcc cggctaattg tattttagt agagatgggg   31320 gtttcactat gttggccagg ctggccttga actcctgacc ttgtgagcca cctgcctcag   31380
cttcccaaag tgctgggatt acaggtgtga gccaccgcac ctggcccaca tagctaacat   31440
ttaatcagca catacagggc catgctcatc attttttgcg cacaatgcca tttaaccttc   31500
acaacagcct gtgagaaggt gtgttagcct cattttacag aggaagaaac taaggcccag   31560
agaagttatg caacttgccc aaggacacac agcttgaagg agctgaggtt taacccgttt   31620
ctacggggtc tgaatcctcc ttaccacccc tatctcccct gactcccagg ttgtgtttgg   31680
tgtacttggg tagtgtccag ctgacaaatg agatgtttta gcttcagaca gtctatgcca   31740
tgtagaaatg cacccaggac tgtgcatatt agggaggttt gcaaatgtgt ccacattaga   31800
taatttttct caaaatgccc ctcactgaac ttctgtcatg cagtatgtac tgagcacctg   31860
cctcttgcta ggtcccggga gagaggatga agagggcaga gcccccaccc tcaggggacc   31920
tgaaaaatgg gagtcctttg tgctcatgga agcagggcct tggggcctca gcactatgga   31980
catttggggc cgggtaattc tttgttgtgg ggggctgtcc tgtagattgc aggatgctcc   32040
gccgcatccc ttgcccctgc cctctagaag ccagtagcac cctccagttg tgaaagccgt   32100
aaaatgtctc cagacattgc tcccagttga gagccacttc attaaagaaa aaaaaataaa   32160
aaagatttct gtatcctcta tacatggact gaatttcact gacatttctc taaaataact   32220
gaatctattt ctatactcat tttttttac cagctgccat tttatttatt tttcttttct   32280 ttctttttt aagaaacagg gtctcactct gtcacccagg ctggagtgca gtggcgcaat   32340
tatggctcac tgcagcctcg acctcctggg ctcaagcaat cctcccacct tagcgtcccc   32400
agtagctggc acgccactgt gcccggctat ttatttatt ttatttatt ttttttgtgg   32460 agacagggtc tccaatgtt gttcaggctg gtctcaaact cctgggttta agcaattctt   32520
ctgccttcat ttcccagagt gttaggattg caggcgtgag ccactgcacc cggccatttt   32580
atttcttaac aaagcacaaa tcaaatgtac aatgcagcta gattttcctt tataaataat   32640
gtctaatgga tttgtttctg tcagctgcct agaacattct ggtatcccag acagaagtgc   32700
```

-continued

```
aacaccaggt ggaggtgttg cagctgagaa gttctgacca gcataccagc accccttaa    32760 aagctgtcta tacttgcggt tctcagctag gctgccacag aatcgcccaa gtcttaaaaa   32820
aacaggtctc tgtcctactg cttgagatgc tggttctcta ggtctgaggt tctggcacct   32880
gtgtgttttt aaaactttac aaataattta aaagcgcctt caagtccaca caacagaat    32940 atttccctcc actcctcatt gtcctggagt tctctaacag tgcagttcta caactggaca   33000
cacgatgtcg cttttcagcc acagttctca ctaagcggcc ccacagggcg gcaggtgcct   33060
tctgcagaga gagagagagg gccttggctg acaggcaag accgggcatc ctggctcctc    33120
ctctgtacag acttttcaca gatgtgaact ctccctactc cctgtcttct gcccccaaat   33180
gaagcctctc agctggcaag agctgagaac taccaagcga gccattgcta atttctattg   33240
tgtttggaac cacaaaaggc agaattatta aggctgtaaa ggacctcaga gcatctggtg   33300
cagtgagttt ccaacttgtg aaaatctgat gtgatctcgg acaagtcact taccccctg    33360 cctcaatttc ttcatctgta aataggata ggaatatatc ttgcccgtct gattgttatg    33420
aagacaaaga gaacaaatgc acataaagcc cgtgaccatg tgctttgtga atggaagctt   33480
taatttattc attcatttat tttattattt attttattt atttatttat ttttgagaca    33540
tagtctcgct ctgttgccca ggctggagtg caatggtgcg acctcggctc actgcaacct   33600
ccatctcccg gattcaaaca attctcctgc ctcagccttc tgagtagctg ggattacagg   33660
tgcctgtcac catggccagc tagttttgt attttagta gagactgggt ttcaccatgt     33720
tggccagggt ggtctcaaac tcctgacctc gtgatctgcc cgctttggcc tcccaaagga   33780
agcttttatt tttattatag ttttacataa ggataaattc agccttagtg aagggaagtg   33840
acttgcccaa gatcatacag tgagactgct ggatctgggg ctctacttca gaattttttt   33900
ttgagatgga gtttcactct gttgcccagg ctggagtgca gtggcacaat ctcggctcac   33960
tgcaacctcc acctcccggg ttcaagcgat tctcctgcct cagcatccct gatagctggg   34020
actacaggct cccaccacca cgcccagcta attttatat tttgagtaga acaggggttt    34080
caccatgttg gccaggctgg tctcaacctg cctggcctcc cagagtgctg agattacagg   34140
tgtgagccac cacgccagtc tactgccatt gtccatgatt tttcctacag ggaaaatcac   34200
aatcccagaa gataagacaa agaacagtaa aaggtggctt tgaggcagt gagttctacc    34260 tgaaggtggg aacagcccag agtgtctggg gacagagtgg taaattctaa tcaagccttc   34320
ccatggcttt gtggatgagg atgagtttct accctgaagc tcggcctgtt cagccataaa   34380
atcaggataa tggtggctgt gcctccttag agtagaatga gaatcagagc agaacaaggg   34440
aaagctgcag tgacttgtca ggtgtcaacc ttcagcatga tgggagagcc atgggacct    34500 tcccctttcc ctaagagagc cagccctcac agcaggcctg ggatccaatg cccagcaccc   34560
agctgggagc ccagggacct tggccaaaat ctggttctgc ttcaacttgg tgcccggcct   34620
ttgtcaagtc acttcctcat ttgcaaactg ggagagtttg gatgaaacta ttgaatgaaa   34680
ttattttggg ggtttctttc tggctctcac agtcctcgca tgctcaccat gttcccttca   34740
atttcattag cacagcccaa caaagggtta agcagtggca gttcctctcg ttctttggtt   34800
aggacaggaa ggtcaggggt gaggccaata caagaggtag ccgccacagc tgatgctgga   34860
aatgacaata gttctttcct agactcatat ttgtcccctc tccctgaagc tttgcctgca   34920
gtgcccttgt aaagaagttg gcaagaagca ggagtgaggc tcagccctc tctgaaatgg    34980 atacgccggt tgctccccct catggctggt ctcatttgcc ttcttcattt ttagacacat   35040
tccaaacttt tcagcaaatt atagtgtttg ccaactggcc gtctggggcc caggagagat   35100
```

-continued

```
gctatttata gcgatgctgg gatgctgcca tcccagagca gcctggtaag aaacggagcc   35160
agagtgcctg ggagtggcgt cctgcaccct ggggagaggc cagggccctg gagcagggtg   35220
gcaaagctgg tggcccgtgg caaggaccac tggcacatcc cctgcctgcc tgggccctgg   35280
ggtctgtgcc catacccac acggggggct gcttccgtgc tccttggaga acgatggtg    35340
ctgtggggcc actgagcaca gtaaaggcta agacccacca taggtcagcc cttgctcatg   35400
ctgactgttg ccccatttcc cttcattctc tcactcgttc attcctcaga atctgcatcc   35460
tggttttgtc actacctgga gttgtaaaga taccaccaag ctcaccttgt ggtgtgagcc   35520
ttgattttcc ccatctgtgt aaagggtgga tctgagctcc aaagttcctt ctagtcatat   35580
gcagagtgca taataaatgt gtttgtattc ccactgtgct cagtgggcac tggggcatgc   35640
agaagagaaa ttggaataaa tgtgacccct gtcctccaga ggctcagtac cagactggaa   35700
ccaggaccca gatgaggggc ctacccagag agggcagcgt gctctcctat ttgtgttagg   35760
cgttaccatt tacaaagggc tttacggctt tgaaggtccc cacaacgccc tgaggaggtg   35820
aagtgtggca atgcccgttc acttgggaaa atactgcatc tcagagagac caagggactc   35880
gcttaaggtc acacagatac agtaagtaag tagggaaaga gctgggggcct ctgggctcct   35940
tttccggggc tctggcctcg gttttaaccc gttctcctag acctctcagt ctctgggcct   36000
cccctctgtg ttccccaccc ccactttcca tcaagagctc agttctctta agttctatat   36060
tctctcttcc ccacccctag aaatctctgc ccgcttccag aaaagctttt gattccgtca   36120
tttttggcat ttcccaccca ggaatcaagg ctgcctcctc tgtgaggaag gcgtgtggaa   36180
ggcgagcagc tgaggacacc tctttttaag agaagcttct ccatgttctt agccaggtta   36240
tataacttct tttgcttctt tcttttccac attctacata ttttttcacaa tgaggatgtg   36300
tcacttctat agttaaaaat ggaaatcttc atttaaaaga acaatcagac acaaggcaag   36360
gtatgcttac cttcccaatg accaaggagc agggagacat tggtcgtgga ggccataggt   36420
gaccagcctt gagggaaggg aaggaagggg aggtgcaggg aggcgcagca gaggcacccg   36480
agtgtgctct acgaatgtaa gtctgccagc tgctcctctg tgcctagcac cctggaaagc   36540
gcccgcacac agtgggccct cagcaaactc ccactgagca aagggccctg tgagtaagga   36600
cctagaagca gggtgtgctt gaggcatggg gtgggagggc atccagcttg gctggcggtg   36660
ggagccgatg caaaggtgag ctgagaccag acggtagaag accttcagtg ctgggccgag   36720
gagggttcct tcatcccata gagaagagct gccatccaag acagaaggct ggggagtgac   36780
atgttgaaat cagtatctta ggaaaataaa gccactggct gggccactgg ctccccttg    36840
tagagggtc tacgaagctc ccgaggtttc agatagtccc tgagagccct tcccctcgcg    36900
atgggctccg tttgaggcat gtccagtgtg aaaggaccac aggccacctg agggacagga   36960
ccaagcagag agctagtgac agaatgccca gggctcaagg acagggctgg agaggtggga   37020
gtggtcccca ccttgagagc caaagggggct gagggctgag ggttgaaggc cgagagccag   37080
gaaggtccag gggagcaaaa gggggagcag agggggagct ggaggtgttg gggtggtggg   37140
tagagagcca agatagggag gggacaagag aggggagaat ctcaaggaaa agcaggagca   37200
tgagactgag agaaggcccc tggaacactg gcttgaatgt ggctgacatt ggcactgcca   37260
gtactcatcc caaaccaggg agctcagcca gcgcccttc tgcatgtccg ctctttcatc    37320
agacagctag gaacaagtta tacgagatga tgtccaagtc caataaatgt ctaagtcctt   37380
tccactggat ctggccccag cctcctctct gaaccatctc ctatcactcc accctatccc   37440
```

```
tgctggctcc ttctgctcca gccatacagg cttgctcctg ggctcagctt gtgcctgcct   37500
ggggagcctc gcgcttgctg tttcctcctt gagaaattcc tgccctggat aactccttcc   37560
cccacttcct tcagatctct gctcccttat caggggcttc ccctggctg ccctatctat    37620 aacagccctg accactcttt tcctcttctc ctgctttctt tgtcttcctg ttcttatcac   37680
taagacatca cacatgtctt agttggcttg tttatattct gtctccaccc atcttagtca   37740
gctactgctg aaatgatgct gtgtaacaaa ccaccccgat actcagaggc tccaaacaag   37800
tgctgatctt tctcatttgt gagtctgtgt gtcagcccga gcagggcagc tccaggctat   37860
ggcttgggtt tgggtggact ccatgtctct ctccattctc cttggaccag cagctccctg   37920
gggcacatgc ttgtcttgga gaatggcagg aacttaaaag ccaagccaaa cctcacagca   37980
cggttaaggg tgatcatgac acaccgctaa cattctagtg gccaaagaag tctcatggcc   38040
aagtgtaata gcagtggatt gggcaagttt actctcttac acctgttgtg aagggagtg    38100 ggagggatg ggggggtgac cgttttcaca acaacagtgc aaactatccc atctcccaat    38160
agaacataaa caccttaagg ttggaactgg gtctgtatcc ccagcactta aaatagtttt   38220
tggcatacag taagggtgca atagacattt gttaaataaa tatacagact aaccaattag   38280
cataatacag atgacaaagg tgtctctctt ctgccagctt ctgtgcctga aatgttgatg   38340
atctcctccc tatcttccta acatctctcc tgtcccacc tgtccatgcc cagggtttgg    38400
ctgctgtgac agaagtgtga gagcctcctg tctcccttgg gatcccagta agagcttcca   38460
tgcctctctc cctgctcacc tgggctccca tccctgggga ccttctggaa acagcttcca   38520
gggctcccag agcttactta gccagattct acatctggct ccagctgtta tcctaagctt   38580
ggccttgttt tctgatctga ccacagcttc atcactccta cctgactgtg ggattctagc   38640
ccccagtggg gtgggggacc aagggtgaca attacctggg accttgacta ttgaaaggct   38700
aatcaggttt gattgggaaa aaagagttgc taaaaggat tgtattggat aattggtgag    38760
atttgaacat ggatttata ttagtattgt gttattacat tttctgatat tagtcattct    38820
tttttttttt tttttttgac ggagtttgct ctgtcaccag gctggagtgc aatagtgtga   38880
tctcggctca ctgcaacctc tgccacccgg gttcaagcga ttcccctgct tcggcctcct   38940
gagtagctgg gactacaggc gggtgccacc acacccagct tgttttttgta cttttagtag   39000 agacagggtt tcaacatgtt ggccaggatg gtctcgatct cttgacctcg tgatctgccc   39060
gcctcagcct cccaaagtgc tgggattaca ggcatgagtc accgctcccg gccgttagtc   39120
attcttatag gtatgtaaga aaatgtcctt gaggtattta gcagggaagt tcatgatctc   39180
tgcagcttac tcaaaatgg ttaaacagaa tgagactaag aacagactag taagaaaaga    39240
ctgaagaata taattattag gccaggtgca gtgactcaca cctgtaaatc ccaacatttt   39300
gggaagctga gataggagga tcacttgagg ccaggagttt gagaccagcc tgggcaacat   39360
agtgagaccc catctctaca aaaaaaaaa aaagtaaaaa ttacgtgggc acggtggtat    39420
acgcctgtac ttccagcttc tgggaggct gaagtgggat gatcagagga cctcaggagt    39480
ttgaggctgc agtgagctat gattgcagca ctgcactcca gccagggaga cagactgagg   39540
cccggtctct aaaaaaaaag gaatctatgt gagtctatat attcgtgcaa cttttctata   39600
ggattgaaac tctttaaaat aagcttaata ataaaaacaa aagctggtgg gtgagacctt   39660
tcatgtactc tccaggagag ttaagccccc caacattcct gtcccttgt ttactctcaa    39720 gcaccccctc ccccacccaa ggaccaggtc tttgtttact gagcatctca gcgatgagct   39780
ctcaccccct gatttcatca attataaatg tgctcgctac tcaccacacg gcaatttgtg   39840
```

-continued

```
acggactgtg gtttgtggtg agagtagcac catccaagtt caccgcagcc gcgagtagag    39900
atgagggttg gggccagaca cagggctgtg ggggcggcaa gggcacgcag gcagccctgc    39960
caccttcctg tttgtcagcc aagtgaggct tccgagggca gcgggcgagc gggtcactac    40020
tcagggccag ctactgcggc caggccaggc tagtcaggtc tgtgcagcca gaactagagg    40080
ctccgccagg atgtgaggtc tcccagctcc tgggaactga agcaaacact ctgactaccc    40140
cttcttgaag tgccttacgg tgtatacatt tgtttaatct gcacaacaaa cctaggagca    40200
gttattgtta ctgtcctcat tttgcagatg aggaaactga ggcaaagaga aattaagtaa    40260
ctccttcaaa gtctggtaag tgacagaacc agattttacc ctcttactca ttgtccatat    40320
tgccgagtaa cttacattaa tagatactat gcatgtttat tttatttttt atttttttt     40380 agagatgggg tctcattctt tttttttttt tttttgaga cggagtctcg ctctgtcgcc     40440
caggctggag tccagtgggg cgtgatcttg gctcactgca agctccgcct ccctggttca    40500
ctccattctc ctgcctcagc ctcccgagta gctgggacta caggcacctg ccaccacgcc    40560
cggctaattt tttgtatatt tagtagagtc ggggtttcac cgcgttacca gtatggtctc    40620
gatctcccga actcgtgatc cgcccacctc ggcctcccaa agtgctggga ttacaggcgt    40680
gagccaccgc gcccggtcct cattctttca ctcagactgg agtgccgtcg tgcaatctca    40740
gctcactgca gcctcaactc ggggctcaag caatcctgcc acctcagcct cccgagtagc    40800
tgggaccaca ggcagtgcca ccacacccaa ctaattttg catttttgt agagaccggc      40860 ttttgccatg ttgcccaggc tggtctcgaa ctcctgagct cagacaatcc acttgcctcg    40920
gcctccaaaa gtgctgggat tatagcacca cgcccagccg atactatgca tgtttaactg    40980
acacctaatg attaggtagc aacaatttct tggctgcctt attccacttc atgaccccca    41040
acattgaaaa tgtcttttcc catgtgaaag catttgtggg ctcctactgc caatctataa    41100
agtagaaatc cttctgtggt acaaagccct cttcttatc taatttccca tttcccgttc     41160
ccccttcccc cttctgctaa gagctcttcc ctacccacat tgtaagtagg gccggggagc    41220
taactccacc ttgcgtactc caaatcaacc acatgaccca ggcctgacca atcagggctc    41280
caaatcctct agctatagtg attggtttag ggagggacat gtgacccgcc tgagccaatg    41340
aggatctgtt ctgggactcc tgtttgaact cttgggaaaa taaactcctt atgttgggtg    41400
gctgagggga tgaatgtgag ctgggagctg caagcaggca tcatgctatt cccttcagct    41460
ttcaagtagt gttttcactg ctgttaacaa ttccaaatct taagtgttcc ttgcatcttc    41520
ctctcgccaa aaatattaca gtactggagg gcttacatgg tgtctcaaat gtctggagtt    41580
taaatctgcc ttgcagcttc catggccaca gtgagtgtct gagtcctggc cgctttctgc    41640
tgatcccggg gagagtttag cctgcctgcc cttcctcct ggttcgttct catgtactca     41700
gatccctgcc tcactcttct ctcacacaga caacaaaga gagtcagatt gtggtcttaa     41760
gtgcacagga ctctgaagtt aggaccagaa gaccttggtt agagtctaaa ccttgtcagt    41820
taccaaatat cattaggcac attagttaat ctctctgagg cttatttccc catcagtaaa    41880
gtgggtactg ctgaagatgt agtctttaga agtgttctct agattgtaag ccccgtgctt    41940
cctggttatt gactaaacag ggataaaaat gagtttctcc tcacctgggt gtcattgagt    42000
ttctggtcat tgtgagatgg gtgatgaagc caagggcatc aaacatccca acgaggctgt    42060
tttctgcatc tccagggcta tcccagcgtt aatcacatat ggaccttaa tcagagtttg     42120 cagaataagt gagaattgtg ttagagtatg aatgtagata ttatcttgtt ttagtcattg    42180
```

```
ttactctagg ggaccattct tactacagga atattgcaca aaacccagaa atttattgac  42240
tttctcctaa ccaaggccta aagagctggt gttagacata ggccaaggcc agccagaggc  42300
ccaaagcctg tttcccaggg taggactgcc ctggcctccc cctctttctc cccaggctcc  42360
accccagaga gctgaagacc aggctgggta cggcactgct gagaaactga ggaaaaggcc  42420
actggcctcc tctctcactg caggctgccc acccggga gg gggaagctt gtcactaaat  42480
caggttcagt tttggtcact gtcttggact ggatattcta gcatcagaac tgagatgttt  42540
cttgtgactt aaagtaactt caggactcta ttctacctag gattgggcag aaaagttatg  42600
ggcctgcggg agttccaatt cagaaacagg ggagattact tgcactaaag aaagtctaaa  42660
ggaaggtagg agacaaaaat aaagttgtgt attgatgatc ctaggagtta tgcttgtttg  42720
acataccagt tatacctgct gtcacggtag ttatgcatta ggggacccag gtgtctgaag  42780
ttatatccag aagacttctg agggtgcacc gggggtccc ttggctaaaa gtgtgattta  42840
aaccctaaga gcctgcccag actatcagtc ccagtttcta cgtccactgt ccctgaatct  42900
cgctgcttct tccttaggct gctgggagtc tgaaccctcc cccgccaaca cccctccccc  42960
atgcctcagt cgtgggaagg gggggccctt gagcagtagg gccaagccct gttcagcctg  43020
ggaccaagtt cccatcaaca aggtggtctg ggcagtggcc agccagaaag cagtaattac  43080
tgtcgaggtg cagggacccc aggtagggcc cccacctccc acctctgtgt gggcagtgaa  43140
tgggcctgcc cctgggtaag gctgtgtcag caggcgcctg cccacccctt gctgggttcc  43200
caggcccta gagccctctc gtaataggag ccatttgcgc tgtaaccagt gggtgaccag  43260
attttttaatc ttggagaccc cttggatccc aggcgggaag tgggatttgt caaatgggga  43320
gaggcggggc tgtctgggaa tgccagacgg ggttgtgctg gggaaatatg tctcctttcc  43380
atacagcccc cttcccatac ctccagcctc cctctacccc gcaagtcagc tctgtagctc  43440
ctaggaggta tctccaacat gcttagctgt tgaaagtaaa tgaatgccgg aagttgaaat  43500
ctgaatggct tgttttgcac taactcaggt gcatgccaaa taggggtgtc tctttgcttg  43560
atcctaatcc ttcctcctct gaaatccttt ctgacctgct gcctatcagc aattgccctg  43620
caaagaccct ctagctggcc gcgggagaag ctgtgttctt ggctatcagg agtgagaaca  43680
ctggacccaa gcttgcctat tctctgccac aactcactgt gtgatcttgg acaagtcact  43740
tcctttcttt cagcctcagt ttcaggagac ttggcacttg ctgagtgcca atgtgtgcca  43800
tgttcttgac aagtatggtc ccacacaacc ttgccaatga ccctgtgacc tgtgtcttct  43860
tgttcccagt ttacaggaga aagatgcag cctgggagag atgcagcagg tgtctgaggc  43920
cacacagcaa gtcacccagg gccaggatct gaagctgggt ctctccagct ccactgcctg  43980
ggcactttct cctccacagc gaccttcagg tcatcatgag gagcctttcg gactaaagct  44040
agagagctgg gattccaaca gttcagcaac ccatgacttc tccatggcag ctgctgcctg  44100
accacctagt gcctttccac taagattgtt ccttccctct cctgaagatt atcctcctgc  44160
ccctctctcc caaacatctg cggtgtgcac ctgctgccca agttgaact tttttttgtt  44220
agagacaggg cctcactgtg tcatccaggc tggagtgcag tggcgtgatc atagctcact  44280
gcagcctcca actcctgggc tcaagtgacc ctctcacctc agcttcctga gtagctggga  44340
ctacaggcat gcaccaccac gcctggctaa tttttaaatt ttttgcagag acagggtcta  44400
gctatgttgc ccaccctggt cttgaactcc tgggctcaag caatctgtct gccttggtct  44460
cccagctcgc tgggattaca ggcatgaatc accatgcccg gtcctccaaa gttgaacttt  44520
tgagactcag tttccttctt ggtaaattca ggctcctagg tgctacctcc tcagagacat  44580
```

```
cctccttgac cacatcacat gacctctcgc agaggccaga ttctttaatg tattcatttg    44640
tctattatca tgtttcccca gtagaagttg cacaaacggc aggggcttca tctgttttgt    44700
ttgccgttat gtccttagca cctaaaattg tgcctggcac atatagtact cagtatgtat    44760
ttgctgggtc aatgagtgag tgaatttata ctaataacag cagctaccat ttctagagtg    44820
tttaccatat attgggcact gtgtcagtct tcccaacaac ccacagacga agatcaatta    44880
ttacacccat tgtacagatc aggaaactga gtcaggttaa gaaacttgcc ctaaatccta    44940
cagtctcact tagaacttct gactgcagtg ctcatcagaa tgcattgtca acccaaaggt    45000
catttccagc tcaggtggct tctatcaaaa gagctcatcc tggcctttcc aagagccaga    45060
cctccgacat cggtggagcc ctgtgcatag ctggcctctc ctgggcgtct tgtcccaagt    45120
acagagacct ggatcctttc ccactcatgt gcaacagccc aaaattaaaa acaaaagcca    45180
tattaaaaaa caaaaccaac tttctgcctt aaaatattgt gagccagggg gcaattagca    45240
attatgctgt attttattat gagaagatag aattctaatt ggactgattt gaattccaca    45300
cacctccaca gattgttttg ggaattaagg tatcagttgt atcggtaatt atggtttacc    45360
attcaattac ccccccacag aaaactgtta aattgtctgt gacgggcttt aaatttagct    45420
cagacctatg tcctatgaag actgcgcgag tcaatacaag ccatccggaa accaccgggt    45480
gccctgtgcc aggcggtaat taggggttga ggtttccaaa gttttacctg agacagcagg    45540
gacaagtgcc tgggctgggc gtgctcacgt ggggggggctt ggatgctccc ccagcacagt    45600
gctcttggct cctgccctgc gttgctggtg caatagctga tcatctggaa gacaatgtgg    45660
tttcagccgc aagtgacatt ttggcgaggt gcaccagcat agaagccctg agacagcgag    45720
ggaccatgta aaactcacgg acattgtaat tggacacatc tgggattgaa ttcccactct    45780
tccacttagg gagtgaactt gagagggcca cttaatatct ttgagcctct gtttccccac    45840
ctgtcaaatg ggtacacctc ctgcctcaca cacgggttat tgtgaagatg gatggagaat    45900
aataatggtg cctggcccaa attgcatttt tttctctttt tttagtactc actacatgcc    45960
agatacttta caaacatctc taaacctcct aagcccctata gggcaggcac tgtggttatt    46020
ctctgtttta tggatgggaa aactgagtcc cagagaggtt aaataacatg ccgaaagtcc    46080
catgactatg aaatggggca gctgggatcc aaacccaggt gacctagggc caaaccctaa    46140
gcatgaagct gccctgctgg gtgccttctg tacctgtccc tctaagtgga agtgcctaga    46200
aatgacccag ccaaaagcag cagactgtat tttatcattt caacaattct ctctgtccat    46260
aaaaagttct atgcagcttg gccagttcct ttttcctgaa tacaaaactg agaatggtaa    46320
cagggaactg acttttttaat gtcatggtgc aaaggagcta gctctgccat gacctccttg    46380
aagtgacctg gtagagtgag ggtaagacaa gccacactcc ctaggctatg gaggccactc    46440
tccatggaga taggggaata gggaatcctg caaaatacag tctctgggga tgggaaggat    46500
cagggaaggg gccaggtgca gtagctcatg cctgtaatct cagcatttcg ggaggctgag    46560
gtgggaggat cgcttgagcc caggagtttg agaccagcag tttgagacca gcctgagcaa    46620
catatcaaga ccctgtcttt acaaaaaatt aacaaaaagg ccaggcgtga tggctcacac    46680
ctgtaacccc agtactttga gaggccgagg tgggcggatc acctgaggtc gggagtttga    46740
gaccagcctg gccaacgtgg tgaaactccg tctctactaa aaatacaaaa attagccagg    46800
tgtggtggct gtaataccag ctactcggga ggctgaggca ggagaatcac ttgaatccag    46860
gaggcagagg ttgcagtgag cccagatcat gccactgcac tccagcctgg gagacagagt    46920
```

```
gagactccgt ctcaaaaaaa aaaaaaaaca attaacaaat tagatgggtg tggtggtgca   46980
cagctgtagt cccagctact caggaggctg aggtgaaggg atcacttgat ccaggtgttc   47040
gaggctatag taagctgtga tcaccccact gcactccagc ctgggtgaca gagtgagatc   47100
ttgtctcaaa aaaaaaaaat tttttttttt aaaggatcag ggtaggtaca tggactcctc   47160
ctattccttc tggcaccatc agtggttgaa cacacaaact ttggttcaaa tcctgcctct   47220
tccaatttgc tagctgtgtg accttgaaaa agttacttaa cccctcttat ccttagtttc   47280
ctcatcttca gaataaaaat agtgcttgcc tgatggggga gatgatggat gtaaagggcc   47340
tcatagaggg cttggcattt accaagtgtt tgagaaatat tggctgtttt tattcaaggc   47400
ctgctcattg ctagcatgag ctacctgcaa cagccacctc taggcctctt ttgctcccta   47460
tagtccagcc acaccaagaa accatgatgg cctgaatcct ctctgacttt gtcaggcctc   47520
cgtgccttta tacatgctgt tccttctgcc tagaaggcct ttctcttttt tcaacctcct   47580
tgagtccatt ttagtccctg ccagatggtc acttctctgt gatgctgccc taactccttg   47640
gcagccatgc tgctcccttg accattcact agccccttta attcagcccc agccacagtg   47700
aggattaaat gggatgatgt ctgagaaagc ccatgggcaa gaacctggca tggagtggtg   47760
ccccataaat gatgaatgga gctgggggttg ctttctcagc cagctgcctg gcaggggcct   47820
ggcttcctca tcttcacacg tcagtgccta gagtaacacc tggcacacag tgaacacaat   47880
ctcagtaact gttagacatt tgtcttttgg ggagctgctc agcctccac attgggtgt    47940 gggttttttg ttttgttttg ttttgttttt tgagacggag tttcattctt gttgcccagg   48000
ctggagtgca atggtgcgat cttggctcac tgcagcctcc gctgcctggg ttcaagtgat   48060
tctcctacct cagcctcccg agtagtagct gggattacag gcacgtgcca ccatgcctgg   48120
ctaatgtttt gtatttttag tagagacagg atttcaccat gttggtcagg ctggtcttga   48180
actcctgacc tcaggtgatc cacccgcctt ggcctcccaa agtgctgaga ttataggcgt   48240
gagccaccac gcccggccta ggggtgtggg gtcttttacc gactaggcct ggtgggggaa   48300
gtcagggacc ccaccacaaa agttggagag gccacatcct cccacctcca tctgggggtta  48360 gacatgtgac ccaggcttgg ccaatcggat gttcctccat cttgcccaga attcacactc   48420
agcagtggtc ttcacgaggg gtggtagtgg tggccagtag gagcagggct gggcagcctc   48480
cctaacccac gttcatgaga cttgaagctg gctggtttcc tgtcccctgg cctcccttgc   48540
ccattcccat cctggtgctc cctccctatg gactcctttt gctcataaat atccctccaa   48600
ttaattgctt tgctgcttct tagctagtgt tgtttctgtc acttgcaacc aagagcctat   48660
tcaggtgcag gaagggttga atgaacaatg gaaatggatc aacacatgtt tctgagcatg   48720
tgctgacagg caggccctgg gcggagtacc acggtgttca aatgatgtgt aagatgtggg   48780
cagtgccccg gggggtctat ggggagacag accatgcatg acatcataaa caagaccaca   48840
gggtttagtt ggaccttgca gacacccaga gaagacgact ttgagccctc attggatggt   48900
gccatcgcaa agtacaaaac gaattgggtt gtaggaactg gaggcactgg gacaatattc   48960
cagattaggg attgagctga aggggttgga aatggctgag tagggtggtg gaaagggatg   49020
cctgctagta ggcaattgtc ttagtctgtt ttgtgctgct gtaatggatt accacagact   49080
gggtaattta taacaaacag aaatttattt ggctcatggt tctgaaggat gggaaatcca   49140
aaatcaagga gccggcatct ggtgagggcc ttcttgttgc atcataacat gccagagggt   49200
gtcacatggt ggaagggcaa agagagggag aaagggaaag agagggagca ggaaagggca   49260
aacccactcc catgataata agctcactca tatcatgagt cattcatcca tcgtgagggc   49320
```

```
agggtccacc tcccaatacc atcacaatgg caactaaacc tcaacatgat ttttggagag    49380
gacaaacatt caaaccatgg cagcagcgtt tgtgggaaac acgcgccaaa gcaagaaaag    49440
accaacctaa gagtgagtga cttggctcct cattctacat tcattttcat ccaatggggc    49500
ccaagggcat gtaccsatta cccatctggg cagttccctt gaatgtgggc ttctgtttgc    49560
ccgtggaggt gaggaacttc aaggaagaaa ccatgaaaga cctcttgagg ctgagggctg    49620
gcaccagcac caagatctcc aggcagctgg aacagtgatg ctcctccgt cctcgcaggc    49680
ggggcaccca acagggtgtg accgtcacct gaggggagac agccagaggc acaggcctga    49740
tcctgggact gaggttggcg gtttgggtgg agaggtgatt ctgagtgtga caccctccag    49800
tgataaagtg gggggcttcc cagcagcccc tggggaaaca ggctgcatct ctggagacag    49860
gagatatgtg gaggcctgag gggcagtgga aagccctgtg tgtctgggtc aggtctctcc    49920
ttggcaggta atggtttgtc ccagtagttt tcagactccc catcctgccc tgtccttctc    49980
ctgtctgatg ctcagacctg tcactcccag ctcagccccc accttactgt ctaccctca    50040
gagtccctcc caccaagggc accttctgtc ccacatctcc atggtgcagt catgggagga    50100
gaacttggga gcataagaaa ctccaccaag ttggggccag gcatggtggc tcacgcctgt    50160
aatcccagca ctttgggagg ccgaggctgg tgaatcacaa ggtcaggagt ttgagaccag    50220
cctgaccaac ataatgaaat cccgtctcta ttaaaaatgc aaaaaattag ccgggcatgg    50280
tggcaggtgc ctgtaatccc agctactcac gaggctgagg caggagaatc acttgaaccg    50340
ggaggcagag gatgcagtga gccaagatcg cgccattgca ctccagcctg ggtggcagtg    50400
aaagacttgg tctcaaaaaa aaaaaaaaag aagaaagaa aaaaaagaa actccaccaa    50460
gggcttttgg gtcctaggga cagcaatgat gtggctggtc cagccagaac ctcattttgt    50520
cagtaaagtt gggacccata ttccctaaga gatttgtccc aagaacacat gggttgctac    50580
agcggaggag aaatcaagtc tgttttccct ctggtgaatt gtccctgaa cgtgctttct    50640
tcctacagtt ttgccaggaa agtaaaaaaa aaaaaaaaa aaaaaaaaaa gtccacgatg    50700
tcagctgggg tgataccaaa acaattgtgg gaggaacaac atccgcaaat tgaatagtgt    50760
gaggagtgtg gacagaagat gtttttgtctt tggcctcatc tcccagactt gatctttgta    50820
aatacagaag tttccaccag agccgaacct ggcaatgact tgaggagcag ctgcaaggaa    50880
gacagcctct cccagggtat cacctggggg cacaccccag cttcccctcc tgagcctcat    50940
cgaggggtta gtgctacctc tcgggaaaac ataaagatga caagaagcca aaggtgccaa    51000
tagttcccat ttagtataaa agctggctca gcaaatcatg ctatttcagg gcctagggtg    51060
ggccagttcc caggcagccc tggcaggaag gactctgaga ggcggacagt aaggtagggg    51120
cttgggagtg ataggtctaa acatctgatg gaagcaaaag ggaggacaag ggagggagtc    51180
aaaaaatccg ggaagcctgt ccttccagaa agtaccgaca ccaggtgag gtggatccca    51240
gcacccgcac ctctgaatgg cctttcccct gcacccctat cccgccccca ctcggagcta    51300
ccccaagcac ctgttcctct gggccccaag gtgacgccct tgtgtgtgt ataggaaagg    51360
acggtgtaca catttggtta gttccttctt ttacaccata aattatcaga gacaacccttt    51420
ttggaaagca atttggcaat aatatcaagt gacataaaga tgttcatagc ctttggccca    51480
ataatcttcc tcctgggaat taatcctaag aaaataattc acaaggaaga aagaaccatt    51540
ttgtatctac aaagacattt attggggtgt tatttatgat agggaaaaac tggagacacc    51600
ctccccagcc aacatagagg gatggtccta taaattatga tacatccatc caatgaaatg    51660
```

```
ttaccctgcc agtaaaaatg gtaaattgaa aattgtgtag caacaagaaa gagtgttcag   51720
aaaataaaag caagtgaaaa aaggagcaca ggattgtcta tatgctgtga tcaatggcaa   51780
tgctgacaaa tccatgtatg tgtagatagt tgtagtgtta cctgtaaggc acgataaggc   51840
ggatgtaact gtgcttcaaa tgttcttttc catagctgtg gagtccttct agtatgaaat   51900
cattttgta aaatcgcaat ttgtcaccag gggttttgac tttccttatt gcctcgtggg   51960
aggtggcaga ggcagcacat ctcagaccga gcctcggttc ctcccctac ctcccaccgc    52020
tgcgcttgaa gaaagatgct gcagcctccc cagtccccat gccagcgctc ccactttct    52080
ctgagctttc ggtggcagac agcgccttgg gcacttttc atgctcataa ttcgaattac    52140
ctgtttaagt cggtcaaatg aaaaaatacc agctccgccc ccacgcgggc tggccggggc   52200
gcctggagcg ccagggcggc tgcagcgcgc tctccgcggc cgtcggccct gagctcattt   52260
cctgggggcgc gcgcgccggg ctatttcagc ctggcgctgt gcaaacagga caatttactg   52320
cggccaaaag ggacccaaat tacaatcgta tcacagacaa atatccgcca cgccaggtct   52380
ccaggggcca ggaggggcct ctctcccggc gcgggggggg ggcgcggggt caggcaggtc   52440
cgcggggctc ggctcggcct cgccgtgccc tgatcggcgt ttgccaccga gctgtgcctg   52500
ctctctgcaa caggaagggg cccagctccc ccgggcgacc gttcctatct gagttctcgt   52560
tcctatctgg gttttcgtgc agaaaaactt catctcttcc cagggatttt ccctgatttt   52620
agggtcccct tttatttggt ttcttttcag cacttgggat gaaaacatcc ctccatccag   52680
ccactccagg gctcaaagtc atatctcctc gttcagaaac ctcagtgcct gtccaccact   52740
cttccggaaa agtcggaatc cttagtgtga tggtcaaaga ccgctcttag tccagtccac   52800
ctgtccaggg ccagcccctg tacccagatg ctccaaccac ggagagcaca tcagactttc   52860
acaatttat ccttgacaat tgccttttca tcctgcctaa atgttcccct gtttctttct    52920
gcctagtgag ctcttattcc ttctttaaga cccagataca catcacctct tccatgaagc   52980
cttcccagac ttcccctttc cctgcttgac atctgccttc caagcagagt cagccccttt   53040
tccttcctag caccgtgcag aggtagatgg tacttctcac atcctgtaat taattgcttg   53100
catgcctgtg gtacaccgta ccattgctca caaatatttc ctcttcctct ctggagaagg   53160
attacacttc cttgatccat tggcctcact caggcttcgc cacatgactg gtgctggcca   53220
gtgaagtggg acatgtgagt tactggggag cagaaacttt caaagccaag catggctcac   53280
cttgttctct cttccctctg ttacaaggat ggcagtgccc cagccagaaa ccacactgcc   53340
agcctggcat aggagtggag cagggcacac ataagtgtga gagaaatgaa cttcacctca   53400
gtgctcgagg ccctgggac catggactca tttgttactg cagcataaac tagctggtct   53460
tgacttcagc ttctgcctct cttccctggc tttgccttca caaaatcaag agtctgatct   53520
tactcatatt atagagctgg tcttcaacca tgttcttttt tttttttcc tttttttttt    53580
tttgagatgg agtttcgctc atgtagtcca ggatggagtg caatggtgcg atctgggctc   53640
actgcaatct ctgcctccct ggttcaagcg attctcctgc ctcagcctcc caaatgctg    53700
ggattacagg tgcttgccac cacgcctagc taattttgt attttagaa gagataggat     53760
ttcaccatgt tggccaggct atctcaaact cctgacctca ggagatctgc ccgcttcggc   53820
ctcccaaagt gctggcatta caggcatgag ccaccatgcc cagccccatg ttcttcgaat   53880
ggccaagaat atcagtaggt aaggtttgtt gagcatggat tgtgtgccag gtgctgtgct   53940
atgcctttgg caagcgttat cccattacat cctttaacag cactctctgg tgggtactgc   54000
tcttatacaa gatttacaaa agagaaaaga gactcagagg aatgtagggg ctcacgtgag   54060
```

```
attgtaaagt agtgagaagt ggagctggtc cttcagctca aatccctctg atgccaaaga    54120
actcaaactc tgcagttcca tcatgtgcat cctcactctc tcacttcctg cagaggatct    54180
gtggaggttg taactattgt tttcacctgt ctcttccact gggctctgag ctgcccgaag    54240
acagatcttt tttttttttt tgagacagaa ttttgctctt gttgcccagg ctggagtgca    54300
atggcacgat cttggctcac cacagcctct gcctcttggg ttcaagcgat tctcctgcct    54360
cagcctcccg agtaactggg attacaggca tgcgccacca tgcctggcta cttttgtatt    54420
tttagtagag acgggggttc tctgtgttgg tcaggctggt cttgaactcc cgaccttagg    54480
tgatctgtct gtctcggcct cccaaagtgc tgggattata ggcgtgagcc accacgcccg    54540
gccccgaaga cagatcttaa tcatctgatt tcccatccat taattcagtc tttcaccaag    54600
gatgtattga gtgccaatta tatgccaggc atcatctgat gtgttgggga cagagaaata    54660
aaacagataa aaatccctgc tgttaattct agcctatggt gacaagaagc agatccgtgg    54720
ctgcctgggg tgagtgtggg gtaggaaatg ggagaaatgg ggatgactgc aactttgggg    54780
gtagtggaaa atgttcagta tcgtggtagt ggtggtggct gtacaggtat atatatccgc    54840
atacatccca cagttcagaa ttatacactt taaatggtaa atggatacag tttattatat    54900
gtaaatgatc cctcaattaa gttgatttag aggaacctgg ccgggcgtgg tggctcacac    54960
ctagtattct cagcactttg ggaggccgag gtgggcggat catgaggtca ggagatagag    55020
accatcctag ctaacatggt gaaacccat ctctactaaa aacacgaaaa caaaaaatta    55080
gccgggtgtg gtggtgggcg cctgtagtcc cagctactcg ggacactgaa cctgggaggc    55140
ggagctggca gtgagctgag atcgcaccac ttcactccag cctgggcaac agagcaagac    55200
tctgccttga aaaaaaaaa aaaaaagaa cccttgctct tatggagaag cattctactg    55260
gggaaaacag acaataaaca catagataaa taaaacatat gtcagaaagg ggtaagtgat    55320
gctcagaaaa ataggacaag ggatcagaag tgctaggcgt tgcaatttaa aataatgggg    55380
tctggaaagc caccctgaga agggccaatg gagctatgcc cagcctgtgg tatccttcct    55440
caggcagggg actgtacccc cagcttacaa gccttttcga ggcaccttca gggtttgagc    55500
ccaaaatgca ctgcacatta agtgttattg atgggcttgt ggaaatctgc tctccgtcag    55560
gctctgatga aacttttcca acaggagact gaactcagta ctgggcatgg cccctgcac    55620 atagtaagtc cacagcaaat gtgtgtgggg tgaatactgt cttctttatc ctcccttttt    55680
ctactccagt ccaggtagac ggtgtatcta cccacccaat tttgctgttt ctggtaccct    55740
cagtgggtct tgcctgctct tcctccttga aatcattact cagaggtctc cgtgtcagct    55800
ccagacagat gggcctggtg ctcctttatc tcaatacaat tcccccgctc ccaggctcca    55860
ggggaaatcc tgagctaact ttggtctttc ctaaactcca cacttccctt tgggcacctc    55920
tttccccatt gcggggctcc ctttcagaat ttgctgcttt atttatttat ttatttttgt    55980
cagaggtgca ttaatgatgc tttatttaaa aacaaaaaac ttggccaggc gcggtggctt    56040
atgcctgtaa tcccagcact ttgggaggct gaggtgggcg gatcacaagg tcaggagatc    56100
aagaccatcc agaccaacat ggtgaaaccc agtctgtact aaaaatacaa aaaaaaaaa    56160 aaaaaaaat cagccgggcg tggcacatgc ctgtaattcc agctactcag gaggctgagg    56220
caggagaatc acttgaaccc gggaggcaga ggttgcagtg agccgagatt gggccactgc    56280
actccagcct gggtgacaga gcgagactcc atctcaaaca aaaaaacacc acaaataaat    56340
aaaaaataaa aacaaaaaac caaaaacagt ccattccatg tcgtgttgaa actgatcagt    56400
```

```
gtaagttaaa tggtggtttt taggctggac ccatgattta agctgtaccc atccagctca    56460
aactgaaaaa aaaaaaaatc atttgaatgt taaagcaatc gttcagagtc ttcaagaaga    56520
aaccaggcag gaaaatgcca ataatgatga ctggcaaaat caaatctaa  aacaaataaa    56580 ctgtttatca agctgccgac agaaaaagaa atcttgcatg gagactacaa gtctggattt    56640
tctgggatga aattgtacag gaatctcagt ctacagtttc ctcaatcgct gtggagatgg    56700
agctgtcact gaatctgaca gagccctgca ctccccagtc cgccgaccct ttctgtaatc    56760
cagtcttcac tgtagcctga ggaactattt caacctgctc cttttttatc ttcttctttg    56820
gcacaacctc agtggacttc tctgattcag aacaagttct aattgatctt ctctgttgct    56880
tcttttctac tgagcctgta gaaccagatg ttgcttcaag agatgatata ttctgcattg    56940
gcttttcatt tctctggttt ggtttagaaa ttataagcct gtcttgcccc ctgacactta    57000
tttctgtttt gttaccaatt cccttttgttg aataaacaaa ttaatttccc atcctctgta    57060
gcattctgaa gagcaaacac ttcttcaatt ttcacagctg gagacatgtt acacttctgc    57120
aaatccaggc tccctttgtg cattgtaatg gaagctggta ggatttcctt gctgccacag    57180
ttttccaggc tattttaaca ggaggtggct cttcctcgtc cgcgcttgtg tgctgcctcg    57240
ggctgtgtct ccaaatgtca gtacttgaga gtgaggaggc cacctcccct gcattgatct    57300
gttctggctg agtttaaagc acagatcttg gtcatcaggt ttttttaact tcggctttgg    57360
agacaacatt ctttttttttt tttttttttag atggagtctc gctctgtcgc ccaggctgga    57420
atgcagtggt gcgatctccg gttcatgcca ttctcctgcc tcagcctccc gagtacctgg    57480
gattacaggc gcccaccacc atgcccggct aattttttttg tattttttta gtagagacgg    57540
ggtttcaccg tgttagccag gatggtctca atctcctgac cttgtgatcc gcccgcctgg    57600
gcctcccaaa gtgctgggat tacagacgtg agccaccgcg cccggcccca acattctttt    57660
ttgcttggga taaaccctct tcaggctgtt aatcaatata gataaaagta tactgttcta    57720
ttctttcttc tcaagtcatt ttcaatgctt tctctgcatg ggcaatgcca aaatcccatt    57780
gagcatgttc tctctgaggt cagggtttcc aaatctttttg tttctcagag tgattgctgg    57840
cttgtttggt tgcctcagcc agtaattctt cataccgctt atgaccttta tactcctgta    57900
cccatttttc atgaacccac accctctctg gctgtttgct aaaacactgg acatgatatt    57960
ttcgggcacc tcctgtgtta attttggtat gaacctccag ctggggatca cttcaatcca    58020
tacaaggcca gcacggatag gttcccacct tggaccacac aagatcacca acttgaaact    58080
taacaccagt ggacacttct gttgttggaa cagaagatag tattggctga actggggctt    58140 cctctttttag tactggatct tcccttggtt tttctgatat ggtgtgaacc ctctcatttg    58200 gtctatttttg ttcctctggt tctaatttgg ggattttgtg tgacttgcgc tcttcagatc    58260
ttgatgagtc atgcttttttg ggttttttcc tcttttctttt tctgctttca tgctttgagt    58320
tcgtgtgctc acttgcctgt acttcattta aaaggtctcc acaaagggaa gacttgaaca    58380
attccctgcc attctggata gttttggtta tttttagttt aacttcaggt gagccactct    58440
tctttggaat cacagtttgt ggtaccgaag tggtggctgt ggagggggaag ggttttctag    58500 aatttaatgt ggtcttctgt ttagaattttc tgaatggtaa tagtcagtgg ggctaaagtt    58560
tctagctgcg ccaaagtcat tggctgaccc attaggatat tgattatgcg actggtattt    58620
ggtttgaatt tcatacatgc tgattgatgg caggtagcca tttgtgagtg gaggaagatc    58680
tgttgtaggt gagtattgaa agctttgctg caaggtagct tcgtatggtg tctggccacc    58740
atcttcagca atgtcacttt tgttatcaaa ggcatcctcc tgacggatgc tggcggagtc    58800
```

-continued

```
agtgagttga ggtggttgtt gaactgtgtt tcccgtgatc ccttgcatga aagagaaaga      58860
gaaatccatt gttctgctcc agcattctta actttccctt tctctcatcg ggccttcagt      58920
ttgtcccgtt ctaaccgccc ggccgtctca atgcgatcac aggagggaca cggagatcga      58980
ggagggccac agccggacca ggccaggcgt gctgcggcag gaggaaggct ccggaggtgg      59040
ggtgggaagg ggaggccgag agacgggtgt cgccgcgccc ccgctgccgc cagagaggag      59100
cctacggctg gcagcctggc ctgggcagca gggtcctcgg cgctcggctg ggaaatcgca      59160
cgtctctccg cggtgacctg tgcacagccc ctggcctcc gcctccgtgc tggcagcctc      59220
cgcctcagcg cacaaagccc cgtcaccccg actctcggag cgccgccgcc gccaaatcct      59280
cagcccctcc ctcattggcc gcggcgtctg ccgggaagtg cagtcccggg tttggggcga      59340
tggagcccag gaggaagcgg cgagtcagcg cggcggagag ggcggagggg acggaggggg      59400
cggaagggga cgaaccacga acgcccgcgg ccgcgaaggg tctggacgac aaaggagaga      59460
ctagcgagag ggcttgttgc ttttttttt ttttttttt tttttttttt tgagacggag      59520
tctcgctctg tcacccaggc tggagtgcaa tggcgcgatc tcggctcgct gcaacctccg      59580
cctcccgggt tcaagcgatt ctcctgcctc agcctccgag gagctgggat tacggggcg      59640 cgcctccacg cccagctaat tctttgtact tttagtagag atgaggtttc accatgttgg      59700
ccaggctggt atcgaactcc tgacctcgcg atccacccgc cttggtgttg cacttttata      59760
actcttttta ccttctcacc aaactagcat ttaggaaaaa aaaaaaaatc aacaaaaaca      59820
aaacaaaaaa accaaaaacc tctatcagtc atttacacgt tagttggaaa taatttagac      59880
cagtgtgtct ctccttcgca gaacacattc agtcctctct gattattaga agcaaggttc      59940
accttttgat cttggttaaa gaaatttcag gctaaatttc tggggaggag atgtatttca      60000
ggttccagga tccagaatt gctctgcaca agtcacagcc atccttgttc cctgaagtct      60060
ctgttggctg caccatgtct gctgctcctt tatgagtggt tttgggagag gccaggctga      60120
gctcttacta gctccttgca acaaaacaag cgaatgtgaa aagtcttaaa cactcagctt      60180
tctggtcaga ggaaatccca aaatcagcat gactcaggat tttaagtgcc ccatagagtg      60240
tccaagagaa gaaacctagg agtctagggt cttcaaaac cccaaagtta aaacctttta      60300 tcacccttc ctgaccttcc tggcttagga ttttaggcag cctcttggag gcctcccttg      60360
cctggggcac acttggccat aaacccattc attcagccct actgatttag tgcccattat      60420
gtgccaggca gaggaaaagt agaaatggta ggatctatct tcaagggct caaagtctgc      60480 aggaaacagg atccgctaac aaattagagc acaagggtgt gccgagtgct ataatagcag      60540
tgtgggttgc tgttgagaaa atacagagga gggtaccacc agggagcttc tatgagttga      60600
gctgagcctt gaaggttgaa gaggcatttc tcacatagag aagacgaaat agtaccctga      60660
ttgtatacta ggaatgaaaa caccaagtgc ttaccaagct cagataggta acgtaaatga      60720
atggagtagg tgagtaaagt agcagggatt gtcagcggtg gtggggaagt ggaaggcctg      60780
catcctgcct acagggcttc tgctggaaag acagcctggc ctggattcag cctccatttg      60840
caccttctgc taggtgcttt tgtgcagtgc acaactcaca caacctcaca tggctgccct      60900
gcctgcctaa gctggccatc agctgcttgt tgccatactg aaaagagggg tttggttttg      60960
cctcgccttg cttttttcaat agaagccaga aacttgaatt tttatgtaaa aatttccaat      61020
ttgtcaaatg ccattgtagc caaacaaaaa tctagcctca ggctggatcc accatagagt      61080
ttcagtttga gaccccgatg ggaaccagtc ccctgggcac atgctgctct ctctcctcca      61140
```

-continued

```
taccatgcaa cacagtcctt tgctgagatt tgacaaggga aacacagtca tagatgaaac    61200
cccctacagc tgctgcaaag cccttcagaa acatgagatt ggcctctgaa ccagaggaaa    61260
gtaacgtggg gctgtacaac agcagccagc ctgtgagact gatggataaa gctttaattt    61320
atcggtgcac cttgtttgga gaaagcttcc ctgccctctt ggctgccccc acctccaacc    61380
cctcctgttt tgctaatgat aaatgacaag cagtggacat ttattaatta aaccaccgc    61440 tgtagccatt ggtaaaaccc aaggccacat gcagggaag cattcaaagc attcctgctg    61500
cccctgccca gggcacaggc cccagggtta cctttgctg gagagagcag gccacgcgg    61560 ccacagcctc acatgatggg ccttcctagg atctgtctgg gttctggctg ataaatggaa    61620
atcacctcca tgggccacac agtaattaaa ctcctggcat tcttttgaca aaaaaaagt    61680 tcctcatggg acattcccac aagctgctga aggtctggga cctgcaagct cccagctgat    61740
taccaaggag ttttcgaagt tggccttgac tgaggatcaa aggaggatgg gagttcaggg    61800
aatgagggtg ggggtgggaa atgccttaga attaagttga tgatggcctg ttgcggtggc    61860
ttatgcctct aatctcagtg ctttgggagg ctgaggcggg aaaatcactt gagcccagga    61920
gtttgagacc agcatggaca acatggtgag accttttctt aacaaaaaat ttaaaaatta    61980
gcctggtgtg gtggcacatg cctgtggtcc catctacacg aggaggctga ggtgctagga    62040
ttgcttgagt ccaggaggtt gaggatgcag tgagctgtgt ttgcaccact gcacttcagc    62100
ctggtgaagg aggagaccct gagacagaag gagaccctgt ctcaaaaaaa agttgatcat    62160
ttggatgttc ggcctgaaac acccacattt atttccccag gaccgagatg ggcagagaga    62220
taaaagcagg ccttcaaggc tcatttattt atatttctac tgtttatttg ttccactgat    62280
gtaccccaag tacctaaaac agagcctggc acatagtagg tgctcaataa atatttgttg    62340
actgattagc tggagatgtg ctcatgtctt tttaacgaaa gcagtaatca ggagaaattc    62400
ctaattaagg tcctagaacc agtggcttct aattgtttgc tgccacagga ttgtaaacat    62460
gttgaagatg aggccagtgt cttattcaat tgactgtccc cagaagcagg cacagtgccc    62520
agcctagggc ctacacaccg tggtttctca acgatatcaa ttgtctgaat gactcagggg    62580
taaaccattt ttcagtgctg ggtcaggcag agccccactg ggacgtgacc tgcacacact    62640
ttggcagtcc cctgggatgc agtggtagca gcagcagagt cataaagcct ggggatcaga    62700
gccacactgg atatcacagc tggaaaggcc tgagatctca gccagtccct tgctaagcag    62760
aaagaagaaa tgaattagct acaaatcttg gggcctctaa aaacacagct tcattttctct    62820 gtttctccta tagactcccc attctgtcca actgccaaaa acatttaagt ttatttaata    62880
atcaatgtca gctgaagttg gtcatatcag acttaaattc aatctattcc cagttgcctc    62940
aacttccctt gtcaggtcat ctacttagtt ctagtggctt ctgtgccata ggaggggag    63000 ctggaggagg gggagagccg agccatggtc atcagtatct gtcttcacta acctcttggg    63060
catggtcacc ccatttttgtt ggtgtctgct aaatccacat cttttttttc tgtagtaatt    63120
agcccacaca ctctgtgtcc tcctgactct gcagctgagg ccctcccagc ccaccaggcc    63180
ctgcccagca ccttccatgc cttccttgga agtgttggaa aactagctgg cccctcatac    63240
tatagggacc cagggaagtt ctgattgacc ctgggtgcca tgatagaaca ggactccacc    63300
cactcagcat tccagataaa cagtggacac agtctccttt gcactcctat tttcccaact    63360
ggttgggagg attctgttgg tgcctgctcc ccaccctatt gggatctctg tctccctggt    63420
gagctgtgta tgtgcatgat ggtgagggtc tccagcaaca aggaaaggag ttacatttgt    63480
ccatattcac actgctataa agaaatacct gagactgggt aatttataaa gaaagaggt    63540
```

```
tcaattgact catagttcca catggctggg gaagcctcag gaaacttaca atcatggcgg    63600
aagggaaaag gcatgtctta catggtggca ggtgagagag agtgtgtagg aagtgaaggg    63660
ggaagagcat cttataaaac cgtcagatct cctgagaact cactcactat caccagaaca    63720
gcatggggga accaccctca tgatccagtc acctcccagc agctctctcc ctcaacacct    63780
ggaaattaca attcaagatg agacttgggt ggggacacaa agcctgacca tatcagaggt    63840
tgatcttgca gcattttatt ctctgaatgt cacatgggga aacggaggtc aagaaggtgg    63900
aaaagacttg cctaaggcca cacagcatga gtgagtgtgc ctaaggccac acagcattgg    63960
gccaagagcc tgggacttgg taagcccctc ctgagccctc ctcctgagcc aggccctgtc    64020
tcaggttcta gcacatgcaa ctgcaaccag cagggtatgt gtcatagtct taaaatatgg    64080
ccacaaattc tttgatggtc ttcccattga gctgtggggt ctatttctct cttttctttg    64140
aatattggca gggttatgac tgcttcaatt aattgagtac agagaggtga tgctgtatga    64200
cttccaagcc taagtcatct caggccatca gcttctgcct ttgttaatgg aacacttgcc    64260
tttggagtcc tgagcctcca ggtaaaaagt tcaactatcc caaggctacc atgctgtgag    64320
gaagcccaaa ctacacagag gggccatgtg aaggcactct ggttgacagt ccccactgag    64380
atgtctcagt ccaggcacca ggcatgtgag ggaagaagcc cccaggtgat ttcagccctc    64440
agcctttcca gccacctcta gccatttgag tcttcacaac cctggcccta gacattggag    64500
agcagagaca ggccaccctg ttgggccctg gccaaattct taaacctctg aatctgtgag    64560
cctaataaaa tggttgttgt tttatgtcac caactttggg gtggcttgtt acacagccac    64620
agatagctgt gccatcttaa cctgctggat tggtacccct taagtctctg atatccatgc    64680
ttctgcccgg ccactaatga agccacatct gttcccacca aagaccact gagaaggcca    64740 gtgagtgtgt ggtggggacc cttgtttgaa ggaagttggg tgaaggaagt tgctgacatg    64800
catgactgct aacaaaagaa tatacatctg cggaggttgt tctggaagta tcttagggaa    64860
gtaaaggaaa ggaattaaga ctcatcgaca acagactcca ttccttgccc tgcccatcct    64920
tattcattta ttcaacaagg ggtctatgag caactacgag gtgccaggcc ctgtgttaag    64980
attctgggac atggacacag gcctggcccct agtggttctc ctagtccagc tagagacaaa    65040
cattaaacga tgattaatat acatactttg aatgaaaaac ttagggtgtt ctgagagtgc    65100
gtggagacct atttaatcct cataatatcc ttctgaggta ggcaccatcc tttctatttt    65160 gcagggaat actaaggctc agaggggtta agagaccttc ccaaggtcac ccagcagggg    65220
agacaccaga ttgcaaagaa gcagccccca cccacctagt gaggccagga agcagaggc    65280 ataaatgtcc agctgagcat gagactcctt gggccaacag gagcacggtg gggtcagcac    65340
cctcagacag gcaacctctg agggagcagc attaacccct gggaagccag ggtagcttgt    65400
taatccagca aacctgcact tctcaagaaa aaatggcccct ctgttgggaa ggaatgattg    65460
agctctaatc atctagcagt ccctgggcag ccacactcac catctctata atgagggcag    65520
aaatagaggg caagaggtat ggtaaccatc cagaggcagt gactgggact cctaaacccc    65580
tccttgattc tgagtcccca ggggccagtg gagggcatt gggaggtgag acaagacatg    65640
cagacaaccc gcctccaaga gatgtcatag agaagtgggc ttcagacctt ggggtgtgga    65700
agcacctgga gaataggtga aaacgctgat gcttggcccc accctgaggg atttgggttc    65760
atttggtctg gggcgaagcc cggcatctg tgggtttttt ttttttttt tttttgagac    65820 agtcttgctt tgttgcccag gctggagtgc attggcatga tctgagctca ctgcaacttc    65880
```

```
tgcctcctgg gttcaagcga ttctcctgcc tcagcctcct gagtagctgg gattacaggc    65940
acctgctcac acacctggct aattttttgta ttttgagtag agacggggtt tcaccatgtt   66000
ggccaggctg gtctggaact ccagcactca agcgatccgc ctgcctcggc ctcccaaagt    66060
gctaggatta caggcatgag ccaccgtact ctgccaaaaa tatatatctt tagattagct    66120
tttaatagag ttcttcaaat acccaaaaga ttagggaaaa ctaggatgct aaaagatgaa    66180
ataggtgact aggcaaataa atcattaggg aaattggttt caggctcatg gtattgttcc    66240
ccacaatgct gggcaagtta cttgtccatt ccaagtttca ttttcccta cctgaacaat     66300
ggagctaata aaattgattt caccgggcgt ggtgggtcat gcctgtaatc ctagcatttg    66360
ggaggccaaa gtggggatgg atcacctgag gtcaggagtt cgagaccagc ctggcccatg    66420
tggtgaaacc tcatttctac taaaaaaaat acaaaaaatt agccgggcat ggtgtggcat    66480
gtctgtagtc ccagttactc gggaggctga ggcagagaat tgcttgaact tgggaggcgg    66540
aggttgcagt gagccgagat cgcatcactg cactcagcct gggtgagtgc agagtgagtg    66600
agactctgcc taaaaaaaaa aaaaaaaaaa tttcacagtg tagttttgag gacgttgtaa    66660
gagggcgtga gttatgtgcc aggtgggtgg taaacgttca atagatgcta ctttccttcc    66720
ttcctgagca tttggaccac acagagacct ccctgctctt ggctttggct ttaaggagct    66780
tgtggtcact gagaggattt tgcactggaa gtacatgcat tcaaaatgga tacctaagtg    66840
tatattttct ggtgtaaact atatgtcgac tctaacttta gcccgggggga gctttattat   66900
ttgtctccct ttcatgaaag ctataataga ggaagagaaa accctgcctc gcacattccg    66960
attcctaaat acataattta taattttctg ggatattatt taagtttatt ttagttctgg    67020
atacacacca tccccgtggg gtgcttattt aagtatcggg tgggctctgg aaaggcctgg    67080
aatgcctcaa aaggagggaa gaagattctt tccattcatt aaacagcagg gcctggggtc    67140
tttgcaggtt ctagggctta gaagtttcct taacaccaac tgaggagtcc cagggtggga   67200
gctgagctca cacgaagctc tacttcgcgt gtcctgaagc tttgacagtt gggcctcttt    67260
ctggctttttg catcctctgc tcatactaag gccagcagag ctacaggttg gaccatggtc    67320
tggccgggag ctccagcttc ctcttttcct ctcagtagtc atcgggccag ctgcccatac    67380
ctggtgccca ggtatgagaa gagacctttg gctttcacca ggttcttgag agggtcaggg    67440
acctccaaaa ggataaatgc cattggtcag atagtcactg tctacctccc tcccatccat    67500
ttcctgcctt caacccctgt tcttgggaca aggccttcgc tggcattcaa tggcgggtcc    67560
ctgaggaagg ccccagcctt gccgaacatc cttcaaggga gacttcagcc cctggccctg    67620
cagtgagtgt gttgttagca gcagaggggc tgagtgaggc agtgggatgg ggcttttctt    67680
ttttgttctg gttgcaaatt ataaaccccc aaatgctgga gttccagact gaggttcaca    67740
aactttagag ggcagaacta aagtcaaatg tgcttttaaa agcaccccag gagatgctga    67800
tgtgggtgga cacttgaaga aacactggtt gataaagttt ctctcttttct ttttttttg    67860
agatggagtc tcgctctgcg gcccaggctg gagtacagtg gggccatctc acctcaccac    67920
aacctccacc tcccgggttc aagcaattct cctgcctcag cctcctgagt agctgggatt    67980
acaggcgtgc gccaccatga ccagctaatt tttgtatttt tagtagagat ggggtttcgc    68040
catggtggcc aggctggtct cgaactcctg acctcaggtg atccgcctgt ctcggcctcc    68100
caaagtgctg ggattacagg tgtgagccac cacgcccagc catggttgat agtttctaga    68160
aagctgttcc aagttactgg ctgttttga attgttcaag cttaaaaaaa agtaggcacc    68220
ctttaggaag gccagtagaa gtcccattcc caaggagggc aggcctgtga gcacgttaat    68280
```

```
ggcaacagtg gcagctaaca accactttg tagccctact gtgccccaga cactgttcta  68340
agcactcata aacattaatc taaacctccc aacagcccca catgccagga cacccgtgcc  68400
tctatttcag gaaaggccat ctggatcttg caggacggca aatgggagag gacaaacaga  68460
gccccatagg tgaaaggag gaacgagagg ctggagagga atggggagca ttagagatca  68520
caaaatgtgg tagacagaat aatggtcccc agatgttcgc atccacatcc ctggaacttt  68580
tgaacgttac cttatcttac cttatgtggc aaaagggact ttgcaggtat gattacgtta  68640
agaatcctga catgtgaaga tcattctgga ttatccagat taatccaggt ggattggggg  68700
aacccagtgt catcacattt aagggtcctt agatgtggaa gatagggta gaagggtgag  68760
tcaagggagt gccatgagag aaggtggaag gggtcacaag ccgaggaatg caggccactt  68820
ctcggatccg caaaaggcga ggatatgtgg tctctccaga taggagcaca gccctgctgg  68880
aacctggatt ttagccccat gagacccatc ttacacttgt gacctttaga gctgtaaggt  68940
cataaatttg tgttgcttta aggctctaag tttgtggtaa tttgttgcag cagccataga  69000
aaactagtag aaggaagaaa aggagcatta agagagattt cccactttgc tttgaaaagt  69060
ggctagaaat agatggggaa acggggagaa gatggcccag agcggaacgg gggagaaagt  69120
cttcttctat gactaaggaa gagtgaggct ctaaacggc cctcaggaaa gtgtttgtgc  69180
catgatgctt ttcaggagag agtagagatc aattgatctc tgtgctgtgt tcttacatga  69240
aatatttggg agggaagtgt tgtggtgagt cacttgtatt ttttttttaaa tacctgccac  69300
tcccagtttt ccagatagct gaggaaaggc tggggttcaa atcccataaa aaaccaacat  69360
cattcaattg gtacattctc taaaatgtac ataagacatc taggaggact tcataatgat  69420
taagagcaat caactgttaa tgcagtgagt gcttattttt tccaggcact gtaccaggca  69480
tgctgcttca tttaaatttt gcagggactt ttgaagtagg tcctaccttg atttccattt  69540
tgcaagtgaa aagcatcaca ttgagatgtg gcccttcagc cttagcctt tgatatggtt  69600
tggctctgtg tctgcaccca aatctcattt tgaattgtgc tgccataatt cccatgtgtt  69660
gtgggaggac ctggtgggag ataattgaat cgtgggggca gtttccccca tactgttctc  69720
gtgatagtga ataagtctca cgagatctta tggttttatc aggggtttcc actttagcgt  69780
cttcctcatt ctcactttgc ctgctgccat ccatgtaaga cgggacttgc tcctccttgc  69840
tttctgccat gattatgagg cttccctaat cacatggaac tgtaagtcca attaaacctc  69900
tttcttttgt aaattgccca atgtcaggta tgtctttatt agcagtgtga aaatggacta  69960
atagacccc cttcctcctt gctaaaatac tttttttgatg gtgatcatga attggccttt  70020
gcgtgcagtg agtttgact ggtctgccaa tgcctttcct ttccagctat gaatggtttt  70080
aaaaaatatc aatgacaagg ccccacctca taaccattaa atgcaaaact ctggtagggg  70140
cccaggtgtt tcttttcttt tcttttcttt tcttttttt tttttttgag acggagtctc  70200
tctctgtcgc cagggtggag tgcagtggca caatctcagc tcactgcaac ctccacctcc  70260
caggttcaag agattctcct gcttcagcct cccaagtagc tgggactaca ggtgcgtacc  70320
accacgcccg gctaattttc tgtattttta gtagagatgg agtttcacct gttagccag  70380
gatggtctca atctcctgac ctcattatcc tcccacctcc gctcccaaa gtgctgggat  70440
tacaggtgtg agccactgtg cccagctggg cccaggtgtt tcttaaaagc tctcaggtga  70500
ttctaatgtt gcagccaggg atgagaccat ttgtctaagg caatctggat aactcctttc  70560
ccattagcca gggattagcc tgtgaactat tctgaccaag gaggcatgaa ctttctgtt  70620
```

-continued

| | |
|---|---|
| tctggatgtt gtcatctgca aataacagga aggaacctag gatctgaaga tgctgctgag | 70680 |
| ctgcctgagt agctcacctg gatccaccct atttctagac ttcttgttat atggtgaata | 70740 |
| aatgtcctcc tggtttaaga caagggttgg caaactatga cccaggagcc aagtctggcc | 70800 |
| cactgcttga ttttgtaaat aaagttttat tggaatacag ccatgcccat ttgtttatgt | 70860 |
| attgtctaca tattgtttag tgctacaatg gcagggatgc atagtcatga cagagacctt | 70920 |
| atggcctgca aagcctcaaa tatttactct ctggcccttg gccctttgca gaaaaagttt | 70980 |
| gccagctcct ggtctaaggg tcttttttgtg ggcctttcta ttacttgcag ttgagggtat | 71040 |
| ctgttaattt gggagtttag cttccccaag gtggcattgt tagtgatggc aagttttgcc | 71100 |
| ccctttaagc cattttttca tgggagaata attacagaat gatctttaag ggatttcaat | 71160 |
| aatatcagcc aatcctactg cccatgggga agtgggatca cacaggttgg ggcttcagat | 71220 |
| aggcctggat ttatggcctg gttttatcat atagatccaa ttgtctttga aaagtgactt | 71280 |
| catcttctag tcctcaactt tctcatctaa aatgaggaca gttatatcta cacgaaggat | 71340 |
| gggtaccctc atggaggcaa ttccagacaa aggaatcagt gcaagcaaag gaagcgaggt | 71400 |
| gaaaaatctc caggtccaca tggagagccg caagctgctc tgcctgacct aagccaagag | 71460 |
| catagaaaag gggtcatggg gcacactgtg gtgaagatag gctggcattt gttgcataat | 71520 |
| aatttctcca gttgtcttgg gtttctgaga ggtagcttct aaacccttgg aatttcccaa | 71580 |
| gtgataggaa tgtctttgtt attcatagtg agccactggg accatgcctg agttcatact | 71640 |
| aacaaggtga ctcatggtgg gccctagat agtttcaaga tggggactag ccattaggaa | 71700 |
| ccaaccaaat gattagaggg ttggggtttt gagccagatt atatcagcct gacttccagg | 71760 |
| gaggttagag attgagttca atcacatggc caattatttg atcaatcatg cctcgtgatg | 71820 |
| aaacaccaat aaaaactctg gacctcaagg ctcaattgag cctcctggtg ggtgaacacc | 71880 |
| agtgtgctag gagggtgata catcctgact ccatggggaa agatatgga agctctgtgt | 71940 |
| ttgggatcct cccagacctc accctatgga tctcttcatt tggctggtcc tgatttgtac | 72000 |
| cctttataat aaaagtgtaa tggtaagtat agcactttgc tgagttatgt gagtcattgt | 72060 |
| agcaaattat caaatatgag gggttgtggg aaccccccaaa tttgtagcca gttgatcaga | 72120 |
| aatgcaggta gcctggggac cccatattat gtggggtctc tgaagtgagg gcagtcttgt | 72180 |
| tgaagactat gtccttaacc tgtggagtct gtactaactc caggtagttg acactgcaaa | 72240 |
| agtatatact gctgtattgc agagctggat tcatgaatgc ctgtttccag acttggattt | 72300 |
| aatttggttg gtggtgggga gccatagaag gtttatgaga agatgaatga caggatcact | 72360 |
| aactgagatt ctggaagaat aattgggcag agataaaggc tatctagagc tctccctgag | 72420 |
| tcacaggatc ttttggtcat gcactctcaa cttttgacatg tgatgctggt caccaaagat | 72480 |
| gcttcctttc aaaaataaac agcagctata aggaactca catatattgg tagggttgga | 72540 |
| gccatcccag ggcaggccag gcctaggagc tacaggaaat cctcacttct ggaagcagaa | 72600 |
| ggtcagttgc ttcttcctgg accacaccct ctgcagacac tagggctcat ggaggagtcc | 72660 |
| tggagggata cacagcccaa gcctttgctt tccaccgtaa gaggatggca gtagaatctg | 72720 |
| ggtacagctt cctcttggag gtttgggaa cccagtgaca ttcaggagcc ccctttttta | 72780 |
| aaccttctgt gccctccagc ttgcttcttt ccagcaacag ctagccactg gggcattgta | 72840 |
| tttcagcctt tctggggcat cccctgcaag ataggcaccg gcactgcctg ctctctctct | 72900 |
| ccctggatct gatttagcct tcactgaaac cctgcccaag atgatgactt aatctctggg | 72960 |
| ctgagcgaat gcagccaata tgttcagatg gatttttgcaa gacaaaagct caaatctgtt | 73020 |

```
ttgtggctgc agatacacat tcagactgaa ccacatccgt ggtcattcca gtcacaaaca    73080
caaagggtgc catgaattct ttccatgaaa ataaatttcc attgtattgt ttctgtcatc    73140
attcatttca tgataagtca gttaaaacag ccggtccgag tctgtcattg attccaagag    73200
ccccattgtc gtgtccttaa cttactgata gttttaggtc ttaattgtta gtagcaaagt    73260
ttcttttcag gaattctgtt ttctcattga ctttgatgag aaagaaaatg tagagagatg    73320
ctagcgaaaa aatttaattg ccctcaaaga agtagcaatc ttttttcttt aatatatatt    73380
atgcatcaag caaaatcatt ttctgagaac tagttccaga ttgcgtccaa tgtcatgggt    73440
tgtgtgtctt atttatttat tttctcattg agatataatt cacataccgt aaaatttacc    73500
attttaaagt gtacaattca gtggttttag tatattcaaa agactgtaca accatcacca    73560
ctacttccag aacattttca tgacagaaaa agaaacttc gtcctcatta gcagtcactc     73620
tccacttcca ctgtcttaca ttccctgaca acaactaatc tctcttccat ctctatgtac    73680
ttgcctattc tggacatttc ataagtgg agtcatataa tatgtggcct tttggtctgg      73740 cttcttcac ttagcatgtt ttcaaggttc atccatgtcg tgcgatatat cagtacttca     73800
tttcacttca gaattgcata atactctatt gtatgtgatg cagggcagat gaaccccaaa    73860
ttgggactta gtccatgagg attttttggct ttgcccagga aggaattcaa gggcaagcca   73920
gaggtagaag acagctttat tgaagcagca gtggttacag ctctgtgact gctcctgcag    73980
aacagggcta ccccataggc aaagagtagc agctcagggt attttgcagt catatttata    74040
ccacttttaa ttacatatgg attaaggggt ggtttatgca gaaatttcta gggaaggggt    74100
agtcactttt gggtcagcgg gtcattgcca tggaaaggag tggtaactcc caggtgttgt    74160
catggcaatg gtaaactgac atggctcact ggtgggcata tcttatggaa agctggttct    74220
gccccttcct tgttttagct agtccgcagt ttggtgtctg acttcatctc tggagtcgag    74280
tctcacttcc tacctcatat ggatatacaa taatgtgtat atccattcat caattgatgg    74340
atattggatt gtttccaatt tttggctatt atgaataatg ctgctatgaa cattcatgtg    74400 caagttttg tactgacata ttttcaaatc tcttgggtat atacctagga gtggaattga    74460
cgtgtcatat agtaaactct atgtttaacc tactgaatta gagtatctgg gactacggcc    74520
cagcaatctg ttttaacagc tctccaggtg attctatgat caccacaatt tgagaggcac    74580
tgccctagag taaggggcag taaacagcta gatagtaaat attggggttt gcaggccaag    74640
agtcaaaact gaggatgtta ggtaagcact tacttgataa gacggtaaac aaatttccaa    74700
acatttttat tgacaaattg aaaaatataa taataataat tggtaacagg gttgtttctg    74760
tttgttggtt tttggttttt tgagacatgg tctcactctg tctcccaggc ttgaatgcat    74820
agctcactgc agccttgacc tcctgggctc aagtgatcct cccaagtaac ttggagctac    74880
aggcatgcac cagcacactg gctactttt acatttttg taaagatgag gtctccctgt     74940
gtcgcccagg ctggtctcaa acttctgggc tcatgcgatc ctcccacttc agcttcccaa    75000
agtgctggga ttataggcat gagtcactga gtcctgccag gaacagtttt ttgtaatgca    75060
ggtttactaa tgagaagaat gtgtttggtt ttttgtttt tttgtttgtt tgttttttgc     75120
tttgttttgt tttttgcagg attgggaggg caacatttta cttaattggg attcaaagtt    75180
ggtgttccct gtcatcaaat caattgcaga tattcatctg taaaaccat tcttccggcc     75240 agcgcagtgg ctcatgcctg taatcccagc actttgggag gccgaggcgg gcggatcacc    75300
tgatgcaggg agtctgagac cagcctgacc aacatggaga accccgtttt ctactaaaaa    75360
```

-continued

```
tacaaaatta gctgggcgtg gtggtgcatg cctgtaatcc cagctacttg ggagctgagg    75420
caggagaatc atttgaacgc gggaggtgga ggttgcagtg agctgagatt gcgccattgc    75480
actccagcct gggcaacaag agcaaaactc tgtctcaaaa ctacaacacc aacaaaaacc    75540
attcttcctt catgggctgt aaagtaataa gccgtgggcc agatttggcc tgtggctcta    75600
tggtttcaac tagttctggt gcatagcagc ccccaaagtt ttagcagcgt ggttagtgga    75660
gagctgtggc ttttgcctcc atctaaattt ttctttgagc aaattacctc tctcctgaca    75720
gccctgttgg gggtgtcagt tgtgggttc tggtacctcc catcccggcc ccagctagag     75780
caggcaggcc cacaggaatt tgaatctgga gggagttatc agtggtggag cgtagaggct    75840
gcaggaatct tcatataagt ggagtcatat aatatgtggt cttttggtct ggcttctta    75900 cttagcatgc tttcaaggtt catccatgtc gtgggatata ttagtgcttc atttcacttc    75960
tgatggcagg gtcctgaatt aagtcctgcc ctgaggatca cactgttaca tctaggcctt    76020
gtaggattcc tgaaaattgc atcccatctg ccctgctcta aaatctacac agcctttgcc    76080
atatccattt atcgatttgg ctcagcaaca tctactaatg atgcttaaat cctgggcaag    76140
tgtatttgaa gtggccccag aggttaaaga tctggatgtt ctccctccag caacagcacc    76200
actgccccac agcctgggga ttttctgttc tgcttgctat taatcactta cttattgcat    76260
acttatatgt gccaaaaatg ggatcctctc ttgccctatt gtaaagtgat acccatcttc    76320
tagaaaccaa tccagcaata tatgagaaga gccatagaaa tgtgcccct tggggaaaag     76380 aaataatcct aagtagagaa aaatgtattt gagcaaagtc attcatggcc acattctgcc    76440
cttccgtggc cagaaatgga taaaagctga atctactgcc agcaagtatc acctccactc    76500
attcatgatg cagagcgtcc ccaccttcc cactgggttg ccttccagaa aacagcttcc     76560
atgatgccca gtaatctctg tttcccttga tctctctcat ctccttcctt gtctaacctt    76620
cttctcttag aaaaggagct tcatccctt tggtcagtag ccagcaaatc tggattgctc     76680
cctgtggccc ttgtgctcaa ggcaaataga accacctgct ccacatcctc ccatcttctg    76740
agtggagggg ccttgagata tccacttct ctgcttagag tggattcttg atgtatcact     76800
ctaatgattt atgaggttaa aagactccct cctcagtagg ggtgagctta aaatgttccc    76860
tcctcagtaa ggatgagcat agagagggaa aaggagctga cagaaccaga gaatcccatc    76920
caccacattt acgatagtga aaacattaga agccatccaa tgttccaaac acctctggta    76980
ccagccaagg gggctgaccc aaggcaggat cccaggagct agggttgagt gggtggggga    77040
ggcactccag gcaacaaggc atcagatctg aggacaggtg ccaggctcag cctgacaagg    77100
taggccaagg gacagttcta gagaagcagc caggataacc tgttttattt tgttttaat     77160 tgggtgcaga cacaagggga gtatggaaag ccattggctc aggtctcaat gggtctcaaa    77220
tttagacttc tgctattttt ttcttcaagt gcaattgcat atttagtctc agagagtgac    77280
tctgacaaga cccaaagaga acatttgtca tttggccttg accttgtctc cacatctgga    77340
gagttggtat cacgtgtggt accttatttg tacatttctt gggggttcat aacaatgtta    77400
taccacatta ctggtgaaag gaatattaat ttgttcagtg taaacactga aatagctgac    77460
aatcttttat ttttaatttt aatctattta tttgttttga gactgggtta agagattggc    77520
taatatttgt atttttgggta gaggtgggat tttaccatgt tgccaaggtt ggtcctgaac    77580
tcttgggctc aagaaatcca ccccccttgg cctcccaaag tgctgggatt acaggtgtga    77640
gccaccacac ccagcctaaa atagctgaca atctttataa ccctctttag gcatatttac    77700
attttatagt atattaggaa cctcaaaaac tgatggcaat tcaggttttt ccagtattca    77760
```

-continued

```
agaaggcatt atctaagctg tcagatctag gggggtggtg agtgtgatac ataaattggg    77820
aggtaaatca aaaagtctgg agcaggcaga agaatgcagg aagaggtcag ggagtgaagg    77880
actggattga gagggccaag atttggggtt tgaacagggc tgacttcagg gagcgggagt    77940
ctggccccag gtaaaactta gtgtcattgt gtgggtcaga agacaacaaa ggatccttaa    78000
ggaaactatg gcccatcatc tcagtagacc aggcagcctt tgggaatgat ggtcacaaag    78060
actctgtggc aacatagaaa atgctaatgg tgtcatacag aatacagaac tttatggacc    78120
tatggtacaa acaaacacat gcatgtgcct gcacacacac acacacacac acacacacac    78180
atacacagag gaaacaagac tggaaggggt tacacctaaa tataagtagt gcttgtgtcc    78240
atggggtgga gtgatattgt gggtttattt gctctgtatt tttaaataaa acaatggctc    78300
aactcagaag ataactgagt cagcgtctca tccagcagcc cccggggccc ctgggagaag    78360
ccacctccca ccacctggcc aagaagatct agacaggctg agaggctccc tctccctctc    78420
ctggggtccc gagccacaaa tctaaagcca cattccttgg gtgaccaggc agggactggg    78480
gacagatgtc gaaactggca aggccccact ctgtggtacc cagcctgctg tggctcctgt    78540
cctagtgcca gctcctctgc tgtcatcccg tccccacccc acacatcccc acctcccag    78600 ccagttgggc ccaaggtgcc ctcactgata tgttggagga ataatctgct tctctccagc    78660
tcctcaggag acccgcgtgg gaggtcccgc gtcacgggct actgaggcac atgctgagtc    78720
ccctcccatg ggcctcagca cacctactat ggcttagctc ttcccaccca ggacctcctc    78780
agggcttctc ggcattccag aaagacaaga agattttctt ggggccaagg cgttgctggg    78840
cctctctgtc ccggccaggc cctcggcaag ctccatgcct cgactctact gccttctctc    78900
tggtcctctc tgtcaccctt cagagacttt taaatcccat agtctgggct tcagggcctc    78960
caataaaagc agaataagac ctataaggac ttaatagagc ttttatctat aaaagagaca    79020
gaccttctaa tctaactaga aactaaggtt aaaaaaaatg aaaagagtta gacttaaact    79080
cttaaaaaaa taaaaaaaga ttcagctctg tcagagtcag cctgatgtgg tagacaaatt    79140
gctcatgaat tactcacagt gtttgctaaa aaatgctggt tcctgggagt ctctgagcct    79200
actctggctc tagaggctgc ccaatttaaa aaaaagaaaa atgcaggttc ctgagtctag    79260
ctccagaact accaaatcaa aatctcgggg aggtgaggac tgggaatctg aatgtgtaac    79320
acgttcccta cgtgattctg aagcacactg caccggtggt ttagtggttt ccatgccagg    79380
agggcattgc gccctccttg agaaccctgc ctcccagcca ctagctgctg ggaggctggc    79440
cagcacagac acagtcctcc ttcccaagag attcctagcc ctggcgagga ggaagactcg    79500
gtgggtaaca ggagttgcaa tgtgggtttg tacccagttc ttggggagca cagaggagag    79560
gggagttctc agagagggaa gatgtctcag ggaatgagtc tctggggcca gatcctgagg    79620
gctcagtagc attgactagc taagaagag agcagaggta tcccaaattg aggacatagc    79680
atgggcagag gcacaatggg gagctgtaaa cagtttaggg cctgggcaca ggtagggagt    79740 agagggggagg aggccagaga gatgagtggg gctggtcttc ctgctggttt gtgttttgtc    79800
catttggcta atctgggaat aatacttccc agaaacccct tctccagagg ggtctagggt    79860
agagttggtc aaaagaggag cttgcatgag atttggaaaa taaagtgaa gcagcatcct    79920 gactctcagg ggggttgtcac ggtcatgtgc cgtgatgaca ctgaggcaga gatatgcctg    79980
gccaatccac ctctcgggct gctggctccc ggtctgccc gtgttctggc cagctgggct    80040
tgctgagcta cagctgcccg cagacctgtc caccggctcc cttcacggcc tcactcaggc    80100
```

-continued

```
agctgatgtg cttgcttctt gggcttccct gcaaactctg acttgtcacc cgtattaggc   80160
cattcttgca ttgctataaa gaaatatctg agaccagatg cggtggctca tgcctctgat   80220
cccagcagtt tgggagccca aggcaggagg atcacttaag cctaggaaga ggaagttgca   80280
gtgagccaag attgcaccac tacactccag cctgggcaac agaggaaaac tctgtctcaa   80340
aattaaaaaa tttaaaagaa ggaaggaagg aaggctgact gacctgagtc tgggtaattt   80400
ataaagaaaa gaggtttaat tggcttgtgg tcctgcaggc ggtacaggaa gcatggtgct   80460
gggcatctgc tgggtttctg gggaggcctc aggaagcttc caatcatgtc aaaaggtgaa   80520
gggggaagcc agcacctcac atggagaggg ggagcaaggg agataatggg ggagaggagg   80580
gaagtgctac acgccttttt ttttcttaga cagggtcttg ctctgtcacc caggctgggg   80640
tgcggtggtg caaccacagc tcactgcagc ctcaaactcc caggctcagg tgatcctccc   80700
acctcagtct gcctagtagc tgggactaca ggtgcacacc accattcctg gctaattttt   80760 tttttttgt atttttgcc atgttgacca ggctggtctt gaactcctgg gctaaagtga   80820
tccacctgac tcagcctcct aaagtattgg aattacaagc atgagccacc atgcccagcc   80880
aggagtccct ttttgttctt tttttaaatt ttatttaga cagagtttca ctcttgttgc   80940
cccggctgga gggtagtgga gcgatctcgg ctcaccgcaa cctctgcctc ctgggttcaa   81000
gcaattctcc tgcctcagcc tcccgagtag ctgggattac aggcatgtgc caccatgccc   81060
ggctaatttt gtattttat tagagacagg gtttctccat gttggtcagg ctggtctcga   81120
attcctgacc tcaggtgatc cacctgcctc ggcctcccaa actgcttgga ttacaggcat   81180
gagccaccat gcctggcagg agtcccttt taagagcagg aaaaatattt tccataagca   81240
actcctccaa cacacacaca cacacacaca cacacacaca cacacacact cagagtccct   81300
ccatggctca tcggggtaga cctttaata tccagggctg agaaggaca atcccttcac   81360 acttgaacgc tgtgaagtct gtgcccttgt ccagggcacc tgccaggagg agtaggcagt   81420
gggtccggtc tttcagtgga gggcttctgc agcttcagat cgtctctagg agtctggagg   81480
tctatcttat ggcttgtatt tctggaaccg agtcatgcct gcttgaagat aagaagatca   81540
aacaacagga tgctgtggct tctcctatcc caggggcctc gaggacaaat cagttccctt   81600
cctgggggag cagatcctcc tggctgggat cttcagtcca agttggttca atttatatcc   81660
ttcacgtctg gcttctcctg catgtccaag tcacaggaat tttaagtcag gatcttctct   81720 gcaccctga gcatgacagc cagcctctgc cctcatgaag ctcccagtct aagggaagaa   81780
ataataaatt ggtggccggg catagtggct catgcctata atcccagcac tttgggaggc   81840
caaggtgggc agatcacttg aggtcgggag ttcgagacca gcctgacaa catggtgaaa   81900 ccccatctct actaacaata caaaaattag ccaggcgtgg tggcatgtgc ctgtagtccc   81960
agctactcag gaggctgagg caggagaatc gctggaacct gggaggcaga ggttgcagtg   82020
agccaagatc atgccactgc cctccagcct gggtgacaga gcaagactct gagattatta   82080
tctcaaaata ataataataa taaaataata ataataaatt ggcagttaga gggcacttca   82140
ccaaggcaat atgagggaaa ctacaatctg tcaggaaaac acagggaag gccctaactg    82200 gcccaggagg ttcagcgggg catccaggag gatgtatgag agccgaggag ggagtagaag   82260
gtgatgtagg aaaaccactt agctgaaaga ctcgctgccc aaaggccgga ggtgggagag   82320
agtgcgggac ttgcaggaac taagaggagc ccagagaggc atctgagaag agaagggctt   82380
ggagagctgg gagcatcaga tcgggtttag cctgggggc tggctgaggt gagtgctctc   82440
catcctaagg ccacaggaag cagaggaggg acaggatcag attctgcgcc cagaggaaga   82500
```

```
ctggcttaga ggaggtgagt ccagaggcca ggagaatatc agaggccagg acaagggaga   82560
cggcggccaa accagggaag tggcactgga gagaaatgga tggattcaag agacgttagg   82620
caaatggaca gaaaacagaa accgcgcacg tggtggttgg tgagttgaat gcatgcagga   82680
gataggggcc caaggagaa ccatagggg ttgattccaa gggtctggtg gagcccctga    82740
ggggttggag acacccagct ggtcagccac acagtctggt attaaatgac acacggctgg   82800
tcagccacac agaagctggg cagtgtgaat gggtccagta ccgacttcag agtgtgcacc   82860
tctgtctccc cagacagcaa cagaaggacc agggaaattt aaaagggagt ctatgaatga   82920
tattgtaata taaatctct aatgaagatg tgactactag aaaaaaggga aataaagcga    82980
ttgaggaaag gaaaacaact tgtgcataaa gaagcaaaga ataagcaact gaaagctcaa   83040
aacatttttc caggcctggg ggatgaggtg gagagagtct cttgctccca ctccaggagg   83100
agggctgcct ggaactaaag ttggtgctta tgatctggta tttaaatgac attcttagtg   83160
gtggtgttag cggtagcaga gcaattgtgc cagggcccac cgacccttg ctggttcact    83220 cagttgccaa catatactga tatactgagc acctgctgca ggccaggctc tgtggtctca   83280
gatctcaaga acaagccagc tcagtccctg tctaatagag cttacaactg ggcagcggag   83340
gcagacctgc catgagacaa atataaaatg acaacttgtg acaagggtta ggaaaaagaa   83400
tagtggaatc ctgttttaga tgggatggtc agggaaggcc tctgaggagg tgatatttga   83460
gccgacatca gatggatggc agagaatgca agaagagtgt ccctggcaga gggaacagca   83520
tcgtcataat tgggagctgg tgctttcgag gaactaacag acaggcaggg tgggtggagg   83580
gtgggagcca gggctgggct gggggttgtg aggacactga caagagacca gttggagagg   83640 gggcggggc tgaccatgca ggaattggaa tctttcagta aagtccagac caaatgattc    83700
ttcagggtcc ttgttccccc aggtttcaat gacactttaa aggtgttgtc gtaaaaggct   83760
ggggagtctg tttctatgcc cccaatctca tttaagaagg ggggcatcca ggccatcatg   83820
gaacaggtga cctggaagat gttccttggt ccagtttctg caaactgccc cgcagcattt   83880
ttagaaaatg ttccctttta gattcgattt atcttagcca aattgaccag ggaaaatagg   83940
tgcctacaaa tagcgatcac tggcaaacaa ggagagttat tatcttaaat taaggctggt   84000
ttctaacaac aaaaaaaaac ccaccaaatg ccactggcca ccccccacca accccgatcc   84060
ccagcgcata cgtgaggacg atggctccac cacctccct gtaagtacca ggctcaatgc    84120
cgggctctgt gcaagggaa ggaaacagac agaggaagga aggcaagaga ttagagaagc    84180
tgacagatgt aaatagcctc agaggagcca cactgtcccg gcatttctcc ccagggagcc   84240
ttttgtacca aggaatctgg ttgcctgaaa gaaaaatggt atcatttatt tctttagtca   84300
gagctgagct gttttcttca gacatagaaa taacctaaca tcacacacca aattgttggc   84360
caaatgacag agatacctgt aatgtgggtg tttaataatg tccagggtaa acaatcatgg   84420
acttggtttc ttgggaaggg ccccgttccc cgccatggtt gcaaagctac agagggtctt   84480
gaatgaaata agtgctttgg aaaagttgtc ccaaagttct tgcctgctgc tgagctggga   84540
ggaagctggg cttttcattt ctgctgctca aatcatgccc cagcagccaa acatccatta   84600
attcaacaaa tatttatgga gcccggattc tggccaagcc ctgtgcaaaa gcactgaggc   84660
tacaaatgtg cagaggctgg ggtcctgtcc tcaatagcct catagtccag aggggagacg   84720
gccacgttca gcctgtgtgt caatcttgta acacagcctg gatgtggcgt ggtggtcagc   84780
tctgtggagg aggcagtctc ctcaaaagga gacttgaagg ggaatttcca ggccagagga   84840
```

```
gttggaggag gggatcctag acagactaag gagaatgtgc aaaagcagag gcttgaaacc    84900
ccctgggcga tttagaaatt aagagaaata cgatattgca gagaacaaag tgctaaggaa    84960
gtcagcggtc aaatgcgtgg ctggacaggt agatggatac cagatcatgt acttgtaagc    85020
taaggagttt agagttgacc ttttaggtaa taaattccat ggaggaattt gagcggggaa    85080
atagcatgat tagattttg tattagaaca ctcactcctc tctgtcctga agaaactcta     85140
gcatatgtcg cgtcaggaga caaattcggg catcttcctt agtgcattgg gtttgatggt    85200 gaaacactg gaaacaaact aaatcagtag aaaaatagat aagcaggcca ggcgcagtgg     85260
ctcacgcctg taatctcagc actttgggag gccgaggcag gtggatcacc tgaggccagg    85320
agttcgagac cagcctggcc aacatggtga aacctcgtct ctactacaaa tacaaaaaat    85380
tagctgggtg tggtggcaca tacctgtagt tccagctact caggaagctg aggcaggaga    85440
attgcttgaa ctcaggaggc agaagttgca gtgagccaac attgcgccat tgcactccag    85500
cctgggtgac agagcgagac tctgtctcaa aaaaaaaaa aaagaaaaa tagataagca     85560 aatagtggta tagtcataaa atataatacc attcaagatt ttaaaataat ccaacatggc    85620
tagatcttaa aagcataatt ttgagtaaaa aaaaaggtg agtttcagca tatgtatggt     85680
atgataaaat gcatgtgaaa tttaaaaacg cacgtttgta tattgattat aaataatata    85740
tgtaggatgg tatgaaaaca tggattgttg cctttggaaa caatccatgg agggaaaggc    85800
atggaaagag aaatacatag aatttttcta ttggttttat atctaaaaga aatatgggcg    85860
gggcatggtg gcttacacct ataatcccag cactttggga ggccaaggca ggaggatcac    85920
ttgagctcag gagtttaaga ccagcctggg aaacatagtg agaccttgtc tctaataaaa    85980
ataaaaaaca ttagctaggt gtagtggtgc acacctgtag tctcagcttc ttgggaggct    86040
gaggtaggaa gaccacttga gcccaggaga tagaggctgc agtgagctat gattgtgcca    86100
ctgtactgca gtctgggcaa cagagtgaaa ccctgtgtaa aaaataaaga aatactgtag    86160
atggagctaa aatgctaacg tattaaattt cctgtgttta aatatttt tgaacttttgc      86220 tttttaaaaa aacagagaaa gtaaaatcca tctggcagcg gcatagcaga tggaagggag    86280
gggattgggg aatgggaccc cgagccagtc tctgtctcca cacagcagct cctgggtgga    86340
ggagagctgg aggccgatct tgggggaccc agggagtaat gcatgcagag aacacttcac    86400
cttgttgggc tgcttttggc ctctgggcag agcggaggcg tggtcctggc atcttgtcta    86460
gtgtccctgg aagatacggg gctctgtctt gatcggaact ggcgaccatt ctgacctggg    86520
atgtcagtat cattttggga catctgccaa ccaagggtca gaaacaggag gattttagaa    86580
tacctgggaa agcttggcat tgtatattca gagtaaagat ggtgtgaatg tgtgtgtgtg    86640
agtgtgtgtg tgcatatgca agcacatgtg caaatccaga agcacagtga aggtgagtgt    86700
tccccaaggg ggtttgcagt ggatgcagtg acgaatacat tcactgatga ggatgctctt    86760
ctatagttca gagaagtaag aatgaatcat gaatctttcc agaaggaatt catttctaga    86820
ctccttctta cctttcagat ctccatcgcc tgacctagag tctcggctga atagcataaa    86880
cctgtatcca tctacatata tttatacatc tggcttagag ccacagcagg gaagaattca    86940
cagcaggatc ttataggcac acagcctata ggatcttata gattcagcc tggatcttat      87000 aggcatccat taaagaaaac tacaggcatt tccgcaactg catatgaatt gtgtcacatc    87060
tgtatgtgct agaaggagtt caagggcatc aatattccta ttgtaataca tctgcccagt    87120
gctagcagca ttacttaagc aaacctatca aaagcctaaa gaataaagat gtggcggggt    87180
gcagtggctc acacctgtaa tcccaacact ttgggaggcc gaggcggggg aatcacgagg    87240
```

-continued

```
tcaggagatt gagaccatcc tggctaacac agtgaaaccc cgtctctact aaaaatacaa    87300
aaacaaatta gccgggcgtg gtggcacgtg cctgtagtcc cggctactca ggaggctgag    87360
gcaggagaat cacttgaagc caggaggcag aggttgcagt gagccgtgag atcgcaccac    87420
tgcactccag cctgggcgac agagtgagac tctgtctcaa aaaaaaaaaa aaaaaagaat    87480
aaagatgtgc accagcttgg gcaacaaagt gaagccccat ctctaaaaaa atacaaaaat    87540
tagccgggca tggtggcaac tgcctgtagc ccagctactc aggagagtga cacaggagga    87600
tggcttgagc ctgggaggca gaggctgcag tgagccatga ttgctgccac tgcactccag    87660
tctgggtgac aaagcaagac tttgtctcaa aaaaacatg tatagctaca taattaataa     87720
tatgcaaata ttcttcttta gggtcactta ggttttcaac atacagaccc aagagaaggt    87780
acagagactc attctctctc tctttcaatc acacacacac acacacacac acacacacac    87840
acacccctct tcactataat tataattact atgttggctt ccacatcagg ggttagagcc    87900
ttggcatgga gacgcctgaa aggcacccaa ggcaattagt ggtgtccctt ctccaccccc     87960 tacataccttcaggcccttt gcacttgctg ctcccctcc cagtgcacac accccagat       88020 ccttgtgtgg ctccctctcc caccacattt tggtcttagc tcaaatgcca cctcctcaga    88080
aatgcctggc ctgccgcct tcagggctgt ctatatgctc accagcttta ttttctttc      88140 gagaactttc cattcccgga cattgtacta atgtttatt tgttatccgt ccattatcca     88200
tctccttgcc agcactccct gtgagctcca tgaggctcca agattacaac cacatgccca    88260
gagctagggt ggtgcctggc tcacagctgg catccagtca gtagcaatgg aatgaatgaa    88320
tgatcaccct ctcttcctct ccatccccac cctctccttt ttcacttcct ctcccgcccc    88380
atctcccctg cctccgcctt aaatctgctg gcatgaccag ccctcaggaa gttgtcaggc    88440
agggagggtg tgtgctctgc acccctctcc ttccatctct cttcccacc tcccttatgg     88500 gtacctatct ctcctacctg cagctgctcg ctgccagctc tggccctctt ggtgggcaga    88560
agcttaggca ccccagacaa ttgtagggaa attgggcatt ggagggcagc cgtaagaaag    88620
gattcagtac ctgccaagga atgatgaatt tagtctctca cccatgaaca ggcatgcact    88680
ttcagggctc aggttcggtc tctaaagcag aacgtcattc agggcaccct tcagtaccca    88740
tgacccagtg tctcgccttt cctgcaggag tcggtgctgc cactatggtg actcagcccc    88800
tctcttctcc tcattcatta cctgggttct tcctgcagtg attgacagta tccttttct    88860 tttgagatga agtcttgctc tgttgccagg gctggagggc agtggcacaa tcttggctca    88920
ctgcaacctc tgcctcctgg gttcaagcca ttctcctgtc tcagcctccc gagtacctgg    88980
gattacaggt gcatgccacc atgccttgct aattttttgta ttttttagtaa agatggggtt    89040 ttgccatgct ggccaggcca gtctctaact cgtgacctca ggtgatccac ccgccttgac    89100
gtcccaaagt actgggatta caggtgtgag ccaccacgcc cagcaagttg cagctcttaa    89160
tagcatgggc accatataat ttactgccca gattgggtca tttttttagag tagaagtggg    89220 agctgttaat aattacgctt ggcctacagg tgtaaacgag accaccctgg gcaaaccagg    89280
cacatggtcg cattgactaa gaggaatatt cccctgcctc ctgcatctcc agccacaaaa    89340
ggagcctcag ctgttggtca aagctgccca atagctgagc ccttgcctgc ccttggacaa    89400
gggagaagac agagggcagg ttccaagaat ggggtgggga tgtggcagga aggacggtgc    89460
aggccccaga gctataatca atgatctggg agccgggttg tggagcacag ggctgtgtca    89520
aggagcaggt gggaggtggg cgggtgtggg acatggcacc agcttttggt gtctgtgact    89580
```

```
ctgaacttgg cttactcgca ggtggcttct gcaggctctc caccctccca gctgcgtaag   89640
tcctgcctga ttcaaggaaa cagggaatt ttggggtcct gtggctcctc caacgttctt    89700
ttcctttacc tccttgtgta aatgtggcct gatttgtact tggagcataa gtagaccccc   89760
acagagcgtg tgtgtgtgtc tgtgtgtgtg tgtgagagag agagagagtg agagagagag   89820
agagagagag agagaaaggg acctatttcc ttctatccct ctgtctgtct tactctcaga   89880
ctattaatac aagccctgag tctggctgta cccccagaac atgtgccccg cccctacaa    89940 caaaatgctg cccctcccag ctaggtctgt tgtttgttcc ttttctgatt ggcgccaggc   90000
ttatagaccc catgtaggta aatataact ttccataaat aacctctaac ccgacctaca    90060
atttagcctt caggtttttt tcccctcgt ggtaatggga ttgcagcctg gctgatcca     90120 tcctgtatct tcaggtccca gaaagcagac cctaggtttg acattgctt ggaattcctg    90180 gtaccccat gttgccttgc acatggcaag gactcggtac atgttgagga atggtggatt    90240
ctcttctacc catgagcagc catgcacttg cagtctttgc ttgggctatg ccttctgcct   90300
agaagccccc ttctccacct ggaaaatctc taagcaacac ccactttgtg aagctttccc   90360
taaccactat ccctcatccc ctccacagag caaattactc ctatcttgga ttcccataac   90420
acttggtaca aaacagtgtg acctggttat tgcccatgtg cccaccaggt tctaagcagc   90480
tcaagtgagg ggtagggcaa ggaactgagc ccaagtatgc ctgtgggcaa aacatttaac   90540
cccttggtgc ttcagtctcc tcagattcaa acaccaacct ggggctgggg gtggtggctc   90600
acgcctgtaa tcccagcact tgggaggcc gaggcaggca gatcacttga ggtcaagagt    90660
tcgagactag cctggccaac atggtgaaac cccgtctcta tcaaaaatac aaaaattagc   90720
caggcgtggt ggcacgcacc tgtaatccca gctactctgg aggctgaggc aggagaatca   90780
cttgaatccg ggaaggcaga agttgcagta agccgagatt gtgacactgc actccagcct   90840
gggcaataga gcgagactct gtctcaaaac aaacaaacaa acaacacaaa cctgacccag   90900
agcccgtgtc cccacccact ggaccgcact gcctctcagg gatggaagat gtctctgttt   90960
cctacctgct ctcatattct gggccctgag acactcatga tgcatggatt ttctgcaggg   91020
gctcactgag gcctcctcgg gggctggagc cccaggaagg gaccggccac tgatacccac   91080
tcacacctat caaagacttg atgatgatga ttaattcaag tgggttattg gtagttaaac   91140
tgacaagtca tcaggaggga cctcagcttt cttttgtgggg gtgggttccc ccaaggtagg   91200
ctggacttaa tttaaagctt tccagttgac catcccacct tagggcaact gaagagtaac   91260
tttagggtta ctcttcatct gaagatgcta actcagctag catccagcac tattaagaca   91320
ccttggggag gcgagacttt gagagaagtg caggaggctg gcccactttt gaagatccta   91380
catttctacc caggaggcat caaatccaca cttcgaagaa gatgaagttt cctgtgagct   91440
ggtcctgaat tgtacttggc tttgtgttgt ctatgccagt actaagcagg acttggccag   91500
gctggtcctc catgaatgac tgtcaaatgg aaaacagaat taggaaccaa agtagtggtg   91560
tagacaaaag gggctggaac ctcagaggag agagggatca tggagattg gaacatctct    91620 ggaaggttag gggaagagat gacaagtaat gtgaatccta aagaaagagg attagttatt   91680
gggggtgcta agtgtggatg gcaaactaag gaagcaggga tctgcatgac catttggagt   91740
cagtaggaag cttggtggag tgggaggtgg gagtcaagca gagaaggcct cccatgtcag   91800 ataagggaaac tgcacttgat cctgggcaag ggggagctat ggaaggcttt tgagcagggg   91860
agtgatacaa tgagaacagc atttggaag ccagcatgga ggggaggctg ctaaaaggat    91920
acaaggctga ggttattacc atgccctggg tgaagaaatg cggtctgggt ttggaaagga   91980
```

```
agggataaac atgactttc aaaggaagac ataattgcca caagggccac cagagagcag    92040
tcaaaggtgt gtccaaggtt ggagctctag tgaccaagag aagggtgtca actttgacag    92100
aaatgacgtc atgtgtggtt gacaaaatga gaccacatc                           92139

<210> SEQ ID NO 2
<211> LENGTH: 51719
<212> TYPE: DNA
<213> ORGANISM: Homo sapiens
<220> FEATURE:
<221> NAME/KEY: misc_feature
<222> LOCATION: 1246, 2572, 2604
<223> OTHER INFORMATION: n = A,T,C or G

<400> SEQUENCE: 2
ggctaatatt ttttattttt attttattt atttatttat ttttgagatg gagtctcgct      60
ctgtcaccag gctggagtgc agtggtgcaa tctcggctca ctgcaacctc tgcctcccaa    120
gtttaagtga ttctcttgcc tcagcctccc aagtagctgg gactataggc acgcgccacc    180
acacccagcc aattttttgt acttttaata gagacgaggt ttcactatat tggctagggt    240
ggtcttgaac tcctgacctc aggtgatctg cccgcctcag cctccaaaag tgctggaatt    300
acaggcatga gccaccgcgc ctggccctga cagggctttg taatgctcaa ataatatgat    360
ccaagggtca gagttgagta aactatagaa catagtcctt gcattccacc ccaggggccc    420
aataacgagg tctttctcta aatctcagaa aacactaagc taagggaggt aagttctgca    480
gatgggtttt ctctgtgtgt gtgtgtgtgt gtgtgtatac atatatatat acacacacac    540
atatatatat atacacacat atatatacat ttaaacctt ggtgctctac ttgtctgcta    600
ccaaaattgt aggcagatga ctgaaaaatg taacacacag aatggcctgc atagaaacct    660
ggctcttgga agtcatatga gtcagttcc tcaactgtaa agtggtggct cactgtacag    720
acactcagta agcacccagc aaatgaacac cttccagggg ttctgtattg gagtcagctg    780
tatagaatga aaacaaatga caaaggggga aacacacaga gtttattat ctcccccata    840 aaaaaggccg gaggtgacag tccaagctga gatggcctct ccccaggca ctgtctctct    900 actttgcccc cctgcggcac cttgttcagc tggcatgtca gcattccaca cagcacgaag    960
gaggaaggac aaatggactc tccccatctc tctgcccact gcccccctcc ccacaacccg   1020
tttaaaaaat agatatgggg ggccgggtgc ggtggctcgt gcctgtaacc ccagcacttt   1080
gggaggccga ggcgggtgga tcacgaggtc aggagatcga gaccatcctg gctaacacgg   1140 tgaaacccg tctccactaa aaatacaaaa aattctccag gcatggtggt ggcaggcgcc   1200
tgtagtctca gctactctgg aggctgaggc aggagaatag cgtganccgg gaggcgtagc   1260
ttgcagcaag gcgagattgc gccactgcac tccaagccta ggcgacagag cgagactcca   1320
tctcaaaaaa aaaaaaaaa aaaaatag a catgggggcc tggcgcggtg gctcacgccc   1380
gtaatcctag cactttggga gtccgaggtg ggcggatcac gaggtcaggg gttcgagacc   1440
agcctggtca gcgtggtgaa aatccatctc tactaaaaat ataaaaatca gctgggcgtg   1500
gtggcgcatg gctgtagtcc caaccactca ggaggctgag gcaggagaat ctcttgaacc   1560
cgggaggcgg agcttgcagc gagccgagat cgtgccacca cactccagcc tgggcgacag   1620
aggcgagact ccgtctcaaa aaaaaaaaa aaatagacat agggtcttgc tatgttgccc   1680
aggctggtct taaactcctt ccttgagtga ttctcccacc ttggcttccc aaagtgctgg   1740
gatttacagg agtgagacac agtgcccagc ctctctacat tttttttttt tttttttaag   1800
```

```
acagactctc actcagtccc tcaggctgga gtgcagtggg tgatctcag ctcactgcaa    1860 tctccacctc ccaggttcaa ttgattctcc tgcctcagcc tcccaagtag ctgggactac    1920
acgcctggct aattttttgta ttttttagtag agacaggggtt ttgtcatgtt ggccaggctg    1980
atctcaaact cctgacctca aatcatccac ccgccttggc ctcccaaagt cctgggatta    2040
caggcatgag ccattgtgcc caaccctccc tgccctgttt taaggagggt cctgttcaac    2100
aattactcta cagaccaatt gcccgcaact atatacttgg cagtgaggaa ctgctgggga    2160
ggctgggaga ttcagcctat aggcaccttg gtggccctaa taactcttt atcttcttct    2220 tcttccccat cagaacctgt tctcaaggaa aagagctaag gtaggctgcc agataaaatg    2280
ctgaggtaag tctgttccag aaaatattgg gacatagact aaaaaattgt tgtttgttta    2340
tctgaaactc aaatttaact gagtgtcttc ttttcccct aaatctggca atcctaatcc    2400
aaggctaaac tcattttcag gacgcaaaag gctctggcct tacctttga gtcaggacgt    2460 tgcactttga cagaaggctc tggaaggaaa ctttaaaggg agccttccag agggaaatgc    2520
ggtgttgggg taggtctgcc tttggctatg ggctttctgg ctgccggagg gncccagggt    2580
cccccaggaa agccttctgt ggangtgtctt ttgagagaga caaagcagag gggtggagga    2640
agggcggctc aggtggaagg agtgaggaca aaggtgagtg cccctgggca ggaagtgctg    2700
aaagagagaa ggagggaggc caccaggcct gggcctggag ccagcctggg agactcccag    2760
ccgcccactt ctcggggcct cccttttcca gcccccttgct ttcgaggcag cagtgccatt    2820
attgggggaa accagctaac cagataggac agcaaaccgg ggatttatgt ggtgtgggaa    2880
cagctcaggt ttccctccct gtttacccag cagtattttt taaaacagaa atcagcgtgt    2940
gggtaaccgc agctgtgagt tactagctct ggctgtgagg ctggggtgg gggagtctc    3000 ttcagagccc tctgtccact ggcctgggag ctactgaagg aatgtgcctc tccccatccc    3060
aggccaggtg gagaaggtgg ccctgcggaa gttcccagat cactgcccac ctcacccttc    3120
ccctcccgac gaaggccagc acacctgggg gaggtgtgat gatggttcaa ggtctaaagc    3180
tttagagatc agtcagttta ggggtcagaa cccatggagc caggcaagta acacaggtt    3240 ccccaagcca gctgggaggg agacacctgg gtgcctttga tgggagaaag aggggggccaa    3300 cagctacttg gcactggcca atttcccctt gcatgaacat gggcccagtg taaccaacca    3360 tatcttttcca tttgtcaaaa aaaagccata tttccagatt ttttatagggc aacctgtcaa    3420 ctttttaaatg ttggcaatga attcaaaaca ctgccattca attaaaagca gcccagaaca    3480
tggcacgact ggttcttgga ataccaatct gcaatctctg atcttgtcca actctctctg    3540 ctcccccattt tacagatcag gaagctgagg cccagagagg cctagggact tagccatggc    3600
tgcagcagtt gttattggga atgccatgag gccaggatgc ctgttatgtg ttctttgccc    3660
agcctagcag tttggctggc ttggctatgc cagaggtctc accatgcagt tctcaagtgc    3720
ttcctgagca tctctcattt gcatagacat gacatttaca aacacatcca tcatctactt    3780
gattctggca atgacaccga gggagcagaa ctggcattaa tccatttttt ttaatggtga    3840
gaacactgag gtttggagag gctggtgacc tgccaaagtc acagtcctag aaagggctgc    3900
agccagggcc tccaattaca gatcaagggt ttttccaccc ccaaactcag tcatctcgta    3960
aaaacgtcag gctccttggg gaatacagct tgagatggat aatcaactcc tcctaaaagg    4020
gaaccataaa tggatgagat acttgggtaa actgaatatt ctttgtaact taaagttaat    4080
tgaaaatcca taggttatca atttttccaag caggagaata aaatagaagg tatttcaaag    4140
agcaattata gtaggcatgg cttaatcttt ctttgatgat tctgaaggca tttcagggga    4200
```

```
atgtaatgcc ttagggcatc attatgaaca ccaataatta ctgtgtaggg ctgtgacgca   4260
aattctcatc aatcccctcc tggctgtcgg ggtgttttca gagaggatca tgcagggagt   4320
gtgaacgtgt gcctgtctgt ttcttgctgc tctctccgcc tttgtcaatt tcagggtgct   4380
gttgtggaaa atgcagtgtc cctggaaggg ggaggtcact taaccttaat gagcttctgt   4440
ttctttatta aaatggggta atgcagactc ctatactcac tgtcaaggtt ttgtgggggct   4500 cagatgtcag tgtcagagca ggaagaaact ttagatcatg atatgcacca gcttcattct   4560
gccatggaaa atctgaggc ccagagaggt taggagcctc gtccaaggtc acccagccag   4620
ggagagggtg ctagaacctg ggttttctgc ttcctaacct ctttcctgaa tataacacta   4680
tggaagaaaa agatctggag gaacggaaag atgaacacat gattacacat gcaaacaata   4740
ctggggtctc tctgatcaga gaaggtgtga tcttccagcc tcaggagagg ggccatccaa   4800
gtcctggagg aggtgaaccc cttagttcag ggctgggagt agcctggggg cagcagagac   4860
actgctgtga ggtttatagt ttcatgactg tcagagcttt ttaaaatgtg gtaattttaa   4920
gtgtgcagcc tcccagggtc tttcttcttt taattgaaga aataaaccat ctcccctaag   4980
gcatgcttgg cgaaggagaa aggcaggtgc aaggctcaca gaggagagca gcagcctaga   5040
agggctctgt gtcatgggga agtaaaaacat cccagaaaca gagagcagaa ggccttgact   5100
gagccccagg agaggcagga caccagggt gcacaccat aaacacacac atacacatgt   5160
atgtctcctc cctggagcct gagagtccct atatacagca ggtgcatgtg ggccacacat   5220
cacacaaaat tgaatacagg caggctcaga gcaccagcac acacgtatgt ccttgacacc   5280
cttagagata ctactaagca cgtgtgtgta cctgctcacc catatggcag agcccctgga   5340
tctgggcaga aatgccaaag caggggcagg cgcgtgtgcg cgcacacaca cacacacaca   5400
cacacacaca cactagcaca gccacaaaag ctcaatccac atccagcatt cctaacaaca   5460
cacacacagc tagacacgct aggagacaca tcaggacaat gtttccactc ccgctgccat   5520
acacatatgc aggtccacat tcaccagtgg ggtagggtag agtctcatca gtccagactc   5580
gcagacagct ggacacagag gtgatctctg aaacccaatg tctacacact gtggtctttg   5640
ttacacacac acacacacac attgaaatga tgtcctcagc ctttggttat ttttggtttc   5700
ttctgagctg gagtttcact cttgttgcct aggctagagt gcagtggcgt gatctcagct   5760
cactgcaacc tccacctccc gggttcaagt gattctcctg cctcagcctc ccaagtggtt   5820
gggactacag gcgcccgcca ccacacccta ctaattttg tatttttagt ggaaacaggg   5880
tttcaccatg ttggccaggc tggccttgaa ctcctgacct cagatgatcc ttccgccttg   5940
gcctcccaaa gtgctgggat tacaagcttg agccaccgca cccggccgag ccttcgggta   6000
ttttgaaagc tgaatgtgtg gttacatttt cttttctttt tcttcttttt ttttgagac   6060 ggagtctctc tctgtcacca ggctggagtg cagtggcgcg atcctggctc actgcaacct   6120
ctgactcccc ggttcaagtg attctcctgt ctcagcctcc tgagtagcta ggattacagg   6180
catgcaccac cacgtccagc taattttgt attttagta gagccagggt ttcaccatgt   6240
tggccaggat ggtctccatc tcctcaaatc gtcatccgcc cgccttggcc tccgaagtg   6300 ctgggattac aggcgtgagc cacagtgccc ggcctacgtt ttcaaacagc aatagcattc   6360
gcctcctctg tcagtttaac ccccatcaca actcccactt ttggcaccta aacagttaat   6420
ttcccagttc atgggccttc aaagtcctgc tctagtctct ggaggaactt tcacctacag   6480
aggaaggtgt aagggaaact agttcatgga tttaagtaga aacattttag gtgtagcttt   6540
```

| | |
|---|---|
| cacatacaga ggagtgagaa aaaactgatt catggattta gatggaaaca ttgtagtatg | 6600 |
| aacccagcgg agggtctggg agcgccttct ggtggtgaga attagaaccg cagcactttc | 6660 |
| tgcaatgtgc ccaggccaga aagctctacc ttctgatagg acccacttct gaccctagaa | 6720 |
| tgggggaact gatggaggtg tcaagccact gtggtcccac agctgcatgc aggcacaggg | 6780 |
| gataggaaga gagctaccta caggttacta aaccattccc ttttaaaaca gcaccaggct | 6840 |
| tatgtctact ctgcgcttcc attttctagg ttttaagtgg aagatatgtg aacacccagt | 6900 |
| gggctggatg gctgtccctg ctacaagtct gtgatgtctc cgtccagtgg cagagctgga | 6960 |
| aggcaggtgc tgtcggggct gcatctgcct tgttcaccag cataggccta aaaccatgga | 7020 |
| gggggtgctt tggcttagat ccccacttgg cctgtgtgtg taagaggctc tcaggcacct | 7080 |
| taatgctaca tcaccaacca aacctcctga tgattctttt aggttctccg tttccaggca | 7140 |
| gattcacttc tgtagattta tttatttatt tttgagacag ggtctggctc tgtcccgcag | 7200 |
| gctggagtac agtgatgcaa tctcggctca ctgtagcctt gacctcaact tcaagtgatc | 7260 |
| ctccaacctc agcctcccag tatgagggac cacaggtgtg caccatcaca cctggctaat | 7320 |
| ttttgtactt tttgtagaga cggggtctca ccatgttgcc cagctggtct caaactccta | 7380 |
| ggctcaagcg atccaccaac cttggcctct gaaatgctgg gattccaggt gtgaagcacc | 7440 |
| gcgcccagtc cctgacttct gtagacgttt gtattgttta catctactgt gtgcaatgta | 7500 |
| cgagatgcag tcaggtgtct ggatggacca ggggatctgg catcttatag acttgggttt | 7560 |
| gaaccccaac tgagccattt actggctggg tgactttggg tgagttctta aacctctctg | 7620 |
| acccttaagg tggtaacagt atcaccagtg aagttggtgc acacagcagg gcccaaactg | 7680 |
| acatctcaca gcacccagca ggtcactgtg ggcatgatag gatgatgggt cactgtgcca | 7740 |
| gccctgaagg agttcaagtc cagatagggg aaggtggtgg accagaccca gacagagatt | 7800 |
| ctgagtcgct gctgagactg ggtgaggata gtgggtacat gggaggacat atagcccggc | 7860 |
| agcccagggc tggagtccac actcaggttg gggcagcctg gtctgcctct cctgcaggag | 7920 |
| acttttccag gcaggcttgt ccctccagaa tgcacgaatc aaatcctctc aggatcagtc | 7980 |
| tcattttcct cgtgctgggg gagcaggcta ctcacagaag atgttgttgc aaatgtaaga | 8040 |
| atcacatgtc gatccacaaa ctggcattga gcagctacct aggagatcaa agaaactctt | 8100 |
| actttgggag ctcctgccag ggctcttttgg gaggtctggc tagctctgga ggaagagaat | 8160 |
| gaacttgggg agggcgtgga acagatgagg acgcaggcac tgccattcaa agaggagagg | 8220 |
| tctcccggac agggctggcc tgggcaggcc cagggagggt ggggctggag cagggacttg | 8280 |
| aaaaagggag agggctcagg agactcagag gaggaggaaa gtgtgtgagc agtaggcagg | 8340 |
| gtgtgtgtgt gtgtgtgtgt gtgtgtgtgt gtgtgcac gcgcgcgcat gcaggcctgt | 8400 |
| gtagggctgg gaaagaacaa agcaaaaggg tgcacaaggc atccagaagc cagggcaatg | 8460 |
| cagaacagga acaaagcagt ttggctcaag gggaaagttc tgatggaaag caaggaaaga | 8520 |
| gaatgttaga agggctgaga gccagaatgc ccagtatggg gtacagaggg caacagaggg | 8580 |
| gctgatgttg gtggcgaggt ggggaggagc atttcacagg gaactgggca gctccaagga | 8640 |
| tgggctggag gagggacggt cctaaagggg gtggtgggag acaggcagtt agtgatgggg | 8700 |
| ggagagaaat gctctgaggg gggctgctgt aggcaggag gggcaggtag caggaggcag | 8760 |
| agggttgagc ctgcagaagc ccggagcagt ctgtagcttt ctaatgcttc ctagggaatt | 8820 |
| ctgctgctga gtagccatgg gttcaacagg tctctaggat ttgccttgaa ttactgccct | 8880 |
| gaggcccct aagtctgggg tctcataaat tcagcgggga gggcacacct gtgtctgagt | 8940 |

-continued

```
ctgagcagcc cagagccccc agtgttgtca gtgaacagct cactgaactt gcagagcaat    9000
taaatcccag ggcagaagaa agagcaggag ggcagggtgg cccccagctc cctcccatcc    9060
cgggtttggg gagagacacc tctggcctga gactcctcgt ggcctctaac aagtcttgct    9120
ctctctctct tttttttttt ttttttaaatt attgtctccc gccctccttc cttcttcttg   9180
ggaatcagaa aagaaacctc aatgcctggc tttgcccctc cctggctgtg gtcaagccat    9240
gtgacattta gacatttcag agcctcctga ctcctgaggc tggagacagc atgaagccaa    9300
atgggcttgg caaacagaag agaggggcag ttaacattct ctgcaatgct ctcttacttc    9360
ccgtttaaac acccctccta ctcggacaca gaccccccaac ccctgtgcca ttgtgctcac   9420
tcccaccttg gagggtcag gctgtggtga aggtcaagg tgaaaagtca tgatgatcct      9480
attgctgcca cctccctggg gtgagcaaga ttctgtggtg gctccagctc tccatggca    9540 gtccacacag aggctgttcc aggttctgga gaggtcactt ggtgtgacct gggaatctgc    9600
atcttttctc tgccaaagca gagggcattg cagcaaccac acctgggtcc cagtcctcaa    9660
caaagtccct ccagctcccg ctgctgtctg caaggtttgg tcatctgtcc ctgcattgga    9720
gaagagtttg cactgtgaat cttgcctcca ccagggaagg ctggtaaaag tccctgcccc    9780
gggggccctc attgctccag ggtgcatctg ggggccagac ctgtggaccc tcaccttga    9840 gcctcatttt gttcctctta gaacaaagcc atttctggta aataggtttg atgggtttgg    9900
cagcagggaa ggcacagaac ctttcacgat tagcaggctc atgacaattt ctctttaggc   9960
aagagagaag gttgaggagg aaagactggc agggcttgga gagctggaaa ggaagaaagg   10020
ccctacaggc ctggggatcc catctctgac caccgacccc agcccccaac tctcatagac    10080
tctgatttga tattcttatt taccaaagaa gctgcatgta tttgcatatc aattctcttt    10140
cccatatcga cacgcaggga ggcttcttcg ttttggatca accagagatc accaatgtct    10200
gcagggtgct cagcccctgg taccttggtc actctaggca gcctcctaga tgtgcctctt    10260
aagataggtt ttctgaaatg ggagaggacc acgccccgcc ccccaccatg gactctggag    10320
tctgcggcgc acaaatcctg cgattttaca gatggggaaa cagaggcacg gagaaagtct   10380
cagctttccc acggcccact gggaccagaa cccaggtcgc aggacgggga cagccacctc   10440 cttttctct ccttgcaacc agcctgagct cgctcagcgg gtggggctg ccgctatcca     10500 gagcaccctg tttctggatg caaaataaag gcccaggcag tgtttggccc tcctctgccc   10560
acagactttg gctccaggc agtctccgag agagaagcct tgggtccac tggtccgagc    10620 tctgcgtgct gagtctagag gctgcagtct ctaagccgaa actagcccag gcctcacagc    10680
cgccttcccg ccggtctccc actgccttgg cggggcgctg gcgccctctg ctggccaagt    10740
ctcgctctgc gcgcaaacgc cccagaaatc agccggaagt tccctggggc cccacaggag    10800
tgaggaccca cctggattca ctttgtcatt ttttttagc tgcatgacct taagaaagct    10860
aatgaacctc agagcactac ctgtgaagtg gaaataatag cgcctacact tcagggtcgg    10920
tgtaaggatt gcatagaata ccgtatagaa agcacccagc acattgtagg tatgtttaat    10980
ggtagcgatt attaataatg cccaactcac atggtgagat gagatctgag aagcctcctt    11040 ataaggtaa atgataacca agtccttgttg caaggcagct ggtgtgttac taatacatca   11100
tgaggtggtg ggccctctgg ggactgtcag gagacagcct ctgttttatt aggaaataaa    11160
acagaatctg gtctgctcca gttttcttcc ttttatttac tgcattagaa aactttcatt    11220
ttatttattg cctattctgg gggttgaggg tgaggggaag gcatgactcc agccaggtag    11280
```

-continued

```
gatacaaaag tatctcaccc cccaggaggg gtttgaggac cggccctccg gcttttagag  11340
aagggcagct ggcttctgtt gctaacgatt tggatttggc ttttaacaga atatcaaggt  11400
gaaagtgaaa ggagcttttc actccttgga gagtcaagag ggtgtggggt gggacctcca  11460
ggggaatgaa gagtgagcga gggtgctggg gggatcccag acctaggaat cagatctggg  11520 gaagggtct gcaagacccc tccatgagtc aagaaaagcc ggtgggtgga tggtgagaag  11580
gaccagtgaa gacactgttt gctggagttg tcccagccag tggctatgac tgagactgtc  11640
ccatggcgtg tgcccagggt cctgccattg atgatggga cattcttttt ttttttttt   11700 tttttgagac ggagtctcgc tctgtcatcc agagctggag tgcagtggcg caatatcaaa  11760
gtcgctgcag cctccacctc ccgggttcaa gcaattctcc tgcctcagcc tcccaagtag  11820
ctgggattac aggcgtgggc caccacatct ggctaatttt tgtattttta gtagagatgg  11880
agtttctact ccatcaggct ggtctccaac ttctggcctc aagtgatctg ctgcctcggc  11940
ctcccaaagt gctgggatta cagacgtgag tcactgtgcc tggcctggat ggaacattct  12000
gctctttctc catctgctgc ctacccatga tgtcttggga ctcctagaac cctaaaggaa  12060 gccctggac acgcaggaag gtgtggagag gagttctcat acttgcactt gggaggaggg  12120
ctcaggagaa acagaggctg gcaacacccc ctcacacact ggtcctctgg agggccagtg  12180
tctacagaca ctgtggactg agtccacaga gaggaaaggg tcctgccttc atcagaactg  12240
ctcagcaagc agttccatcc caggggtcc tgcgaggtaa gggagggca gctagctagg   12300 tgaggggctg agagagtggg gaggggaaag agggaagaag agagtgagag ggagagggag  12360
ggactgagcc gattctcagc tccttgaccg tttgctgagc tctgtctgag tggacagatg  12420
gtcccaagtc aggccacacc agagtggcct ttctgctccc ctacaccctg cattcctcaa  12480
cattgctggc cccggagaga ctttccttca gagaagcaaa tggctgggga atggtgaaag  12540
acactgcaga gaaaagaaag cacagcctgc tgccctggga attaacatga tttaggagac  12600
ctgcaggtca cccctcatg actaaaagcc atcctggaat gaaggtctgt ggctatttct  12660
aggcaaaact gtctgataag ataaaatagc tcaactcctg accattaagt cgtgaaggcc  12720
atggccatcg taaatctcat cttttccggcc ctctggcctg catgcagtgc agcccagcca  12780
gtcggtggca gccaccttgg taggaagggc cctcatcctc ctggctgtgc cccaaggact  12840
gggcaggctt cggtgccaag ggtagtgcga gcacttgaaa gccgccctgt atgtttattg  12900 ttttcccag gtgatccaga attactcccg aactctacca gctgaaatcc tcctcaactc   12960
acatcagaca agacggccct gccacttacc tgtcagatca ctttgggcag gtaagctcat  13020
tttcctgaat ctttacttcc acaccttaaa atgtgagcaa tactatctcc ctggcaaggt  13080
tgtttgtgag ggtaaaatga aacaataatc acgggtgcat cctggagctc tttcttacaa  13140
ggcgtgcccc caaatctgtc ccctcttct gaggatgccc ttcccctatt gtctccctgg    13200
ccatttccta cccattctca agggccatga tctcagggag ttcctgac tcacccaggc    13260 atattggatc tcctacgtac tgctacgact gcacacaggt gcaggaaatg gctgtttgct  13320
ttgcgtttga ggaacttgga aagggagacg tggtaggaa agtagtggtt aggggcactt   13380
tcagactgaa ggatgtgggt tggggaatac gggattcttg gagttgagga cgccgcttct  13440
ctcgtctcta gctaatgtga gaaagaccct tctggacact aagcctgcaa ttccactggt  13500
ggctaccagg tgtccgtggt gtcctgggc gggtgtaatg agagcgggag cctgtgaaac   13560
caaaagcatt gttttataa attcagcact cttcaatccc tattaataag gttagcggtg   13620
cagttcttgc gtctcctgcc ctgcctcacc ttgcaatcat attcattggc attcctttct  13680
```

-continued

```
tccaagaacc cacctaggag gccttgcagg agatatctct ggtgctggct gttcctgcag  13740
tctgaaaagc cagttaagat acaaatatgt gagaggacac tgcttgaatc tgatttcatt  13800
ttttaaaaag tttaattatt cacagacttt gcttctttct gactagtaat gtgacacctg  13860
tgactcagtt caagatggtg tgtggtgacc ttgcagttga aagcactga gcgctatagc  13920 catgccaaga aggttgccct cctgggacca gcaaaaattc catccagggg gccatctctg  13980
tcaggcttgt cctgactatc tttttggaga ggcggcagag tggagtggtt aaaagcatga  14040
ttctggagcc cagctacctg ggagcaaagc tcgtctctac cgcttaccag ctctgagagc  14100
ttaggcaagt gacctattct ctctgtgcct ctgagttttc atctgtgaaa tgggagtaac  14160
aatagtcctg tctcacaggg ttgctgggag gcttaatga gttaatgtcc atgggtgct  14220 gaatcagtgc ctggcatacg gtgaaggcca tgtgagcagt aaatattatt attattagaa  14280
aggttggctg gcgtggtgg ctcacacctg taatcccagc actttgggag gctgaggtgg  14340
gcagattacg aggtcaagag ttagagacca gcctggccaa catggtgaaa ccccatctct  14400
actaaaaata caaaagacat tagccggtat agtggtgcgt gcttgtagtc ccagctactc  14460
aggaggctaa ggcagaagga tcgcttgaac ccgggaggca gaggtttcag tgagctgaga  14520
tcacgccact gcactccagc ctgggcaaca gagtgagact ccatctcaaa aaaaaaaaa  14580 aaagaaaga aagaaagaaa aaagaaaag gtcccaacct actcacttat tgttcacttg  14640
catcaaatgc taggttcagt gtattgttct tgtaagatta gaaatggaga gatgggtcag  14700 aagggttgg tcaaaataga cctctcaacc caagcagaca gggctggctt catggccggg  14760
caaccatgca ggacccaggg ctctaagata agaaaggcac gtagtttaat gctttgctgt  14820
cccatcttga tactgttttt tttttctttt tttttggaa atggagtttc actattgtca  14880
cccaagataa agtacaatgg cgtgatctca gctcactgca atctctgcct cctgggttca  14940
agcaattctc ctgcttcagc tccttgagta gctgggatta caggcatgta ccaccacact  15000
cagctaattt ttgtattttt agtagagacg gggtttcacc atgttggcca ggctggctgg  15060
tctcgaactc ctgatcgcag gtgatccacc cacctcggcc cacaaagtg ctgggattac  15120 aggcatgaac caccgtgcct agctgatatt cttaatttat gaaggaaggg ccccaaattt  15180
tcattttgca ctgggcccac aaataacgta gcaggtccca caaacaaatt cgtctagatt  15240
cagagggccc cttgccttcc tcctctgctc acattcgttc ctttctccca tcacaggcgg  15300
gtaccctacc ttgggggatt tgccccagaa taagcctttt ttttcccttc taacatttta  15360
atgaaaaatt tcaagtgtat agcaatgttg aaaagatttt atagtgagca cccatacacc  15420
tgccacccaa agtctaccat taatgtcttc tggacttact tttgccgtct tattcatact  15480
ctgcctggac tgtcctcagc tacaggactc acatctcttg ccgacagctc taaggcttcc  15540
agtcctgctg tctggaccaa gaaaggcttc ctgggctctg agtgtcaaat gcggccttc  15600 aaggaagggg aatggtggaa aaggccgtgg ggggttttgg agaaattgct agggaaagac  15660
tggcaccaga gttccaccag cccaggcaat ggggggtaca gaacccataa gatgagttct  15720
agaaaagcaa ggaaggttc gttctggagt ttgtggactg aggtttccat tgtgactag  15780 gattctcatt ggttccttat gtagtttctt acgcccctgca tagtcttcta gcatttctc  15840 acagacgtgg tctgggggcg aacaccagca gccctgagag gtggctaaag aggagattct  15900
tctctccact tcacatcgta ggaaactgag tctcagaggt tccttccctg gcctgcccac  15960
aaccccaggg ctaaagagg cagaccaagc ccagggcctt gaaccccaac aatgggcctc  16020
```

-continued

```
tttcttttga tcccatgata ggggtgcaaa agcattgcat tccccctgggt aatttgaaga   16080 aaaaacccaa aaaactccaa ctttgtctcc aggaaaaaga gggtgtctgg gctatgattt   16140
acctctgagg gtgtggttgc actgagcgtg atcacacttc aaagggttag atctcatttc   16200
tctgcctttc tagcttgggc ccagggctca gaaatgtgtg gactccctca cagcccctcc   16260
cagcatccct gccccctccc aactgccttg gcaggtgac acctgtatta ttgctaaggg    16320
ttaaaaagcc cccaaatcaa taaaacccat taatgagtgt tggtacctcg aaggctacag   16380
ataaatccct tctactcagt gagttcaatc ccataaaaca gctctcccct ttcaatccta   16440
gcattcattt gatagaaaat gtggagaaat tttaaaaagg tgacttacta attgcctgta   16500
aaataaaagg cagatggaag ctttattaca gttgaaggaa gtcgggaata ttaaggtaaa   16560
atgtcaaata acaattgatt ttccttagac ataaaggggc gatttatggc ttcctagtta   16620
ctacaaacga gaaattattt gaagttctga aaagtatgag gagaaataaa gattaaatag   16680
aagatgaaat catagggatt tctctgggag gtgacttcag tgcccctggg gactagaatt   16740
catgtggcca gtggcctagc cagctggggc ttggcagttt caagatttag aggcaaggtg   16800
tctctgagga gcggggaagt ggctgtttgc tttgtgtctg aggaactagg aaagaaagat   16860
gaagataggg aaagttgtgg ttagggccaa tttcagactg agggatgtgg gattagggga   16920
ttcttgtgga tgggcctata gctctgcttc ctgactagca gatactgggg atctggggaa   16980
gggaagggtg agctgccttt cctgggactt cgatggcatc cttacagtca ggggacactg   17040
tccttgctgg gtcccggaca tcagtgtcta tgtatccctg caagccacag cactatccag   17100
gccctctggt ggctttgctt ggtctgggcc aacctggtct ccacactgac agtcaaagac   17160
gaggagagga aaagaactc acggctaggc gtggtggctc ctgcctgtaa ttccagcact   17220
ttgagaggcc gaggcgggtg gatcccttga gcccaggagt ttgagaccag cctgggcaac   17280
atggcgaaat ccccgtctct acaaaaaata gagaacaatt acccaggaat ggtggtactc   17340
tggaggttga ggtgggaaga tggcttgagc tcgggaggtt gaggctacag tgagctgtga   17400
ttgtgccacc gcactccagc atgggcgaca gagcaagaca ctgtctcaaa aaaaggctc    17460 atttccaggc tgccaggctt atgttagcct ggggtcccgc aggagctgac ctgagacaag   17520
tacttgaggg caagttgttt gtttgaggga tgctcacagg aagctccagt aggagggtag   17580
ggaggtgacc cagggaagga aggcagctta caggggcgtg ttgtcaggaa gggcaccccg   17640
gcgggtgacg gaagcttaat tttgctggga aactcaggag ccagcatgga acctgcacct   17700
cagagttatc ccactggaag gatgagggag cgggtactta tacaccaact ccatccccgt   17760
cctttgttaa ggctgctgga tggagtgggt gggacactca ttcttcagca ctcccagggg   17820
ccctcaggct gtcagaagtt aggtccgttg gctccagga tgagggacc cccagaagat    17880 gcgggagggc gtccgcagca tctgcctctg tgctttccct gtttatctga atcctcataa   17940
ttcccgccac atgcagatca gagcccccag ctttatggaa gagaacacag gtttggagaa   18000
gataaagagc attcccacaa ctaggaggtg gggaaagcta ggagttcagc ccagagctcc   18060
ctgacttcaa agtccattct ctttctactt cctgattttt ttttttttt tttttttg     18120 agacggagtt tcactctgtt gtctaggctg gggtgcagtg gcacaaactt ggctcactgc   18180
agtctctgcc tcctgggttc aagcaattct cctgcctcag cctctcgagt agctgggact   18240
acaggcgccc gctaccatgc ctggctaatt ttttgtgttt ttaatagaga cagggtttca   18300
ccgtgttggc caggctggtc tcgaactcct gacctcaggt gatccgcttg ccttggcctc   18360
ccaaagtgct gggattacaa gcacgagcca ctgtgctcgg cctacttcct gatttttgta   18420
```

```
taagacacat cccagcagca tggtagactg aagactcctg ggcccactct cagagattct   18480
gctctggcaa ggatgtgttt attggtgaga ggggtgtcca ggaatacgtg cctttttttt   18540
tttttctaga gacagggtct cgttgtccag gctggagtgc agtggtgcaa tcatagctta   18600
ctgcaatctc aaacttctgg gttcgagcga tcctcctatc tcagcctcct aagtagctgg   18660
gactacaggt gcacgccacc atgtctggct aattttttaaa ttttttctgg agttggggtc   18720
ttgtgatgtt gcccaggctg atctttaact tcaggtctca agagatcctc ccaccttggc   18780
ctcccaaatt tttgggatta cagccatgag ccactatgcc caactagaat atgcactttt   18840 tttttttttga gaccgagttt tgctcttgtt gcccaggctg gagtataatg gtgcgatctc   18900
ggctcaccgc aacctccccc tcccaggtcc aagcgattct tctgcctcag cctcctgagg   18960
agctgggatt acaggcatgt gccaccatac caggctaatt ttgtattttt agtagagatg   19020
gggtttcttc gtgttggtca ggctggtctt gaactcctga cctcaggtga tcagccccgc   19080
ctgctttggc ctcccaaagt gctaggatta caggcatgag ccaccaagcc tgaccttttt   19140
tttttttttt gagacagagt cttgcttgt cacccaggct ggagtgcagt ggcacgatct   19200
cggctcactg caagctctgc ctcccaggtt catgccattc tcctgcctca ggctcccaag   19260
tagctgggac tacaggcact tgccaccacg cccggctaat tttttgtatt tttagtagag   19320
atggggtttc accgtgttag ccaggatggt cttgatttcc tgacctcgtg atccacctgc   19380
cttggcctcc caaagtgctg ggattatagg cgtgagccac cgtgcccggc cttttttttt   19440
tttttttttt tttttgagac aggatcttgc ttggttgccc aggctggagt gcagtggcct   19500
gattacagct cactgcagcc tcaatctcct ggactcaagc aatcctctca cctcagcctc   19560
ttgagtagct gggaccacag gtgtgtgcta ccacacccag ataattttg tgcttttgt   19620 agagacaggg tttcgacatg ttgcccaggc cggactaaaa ttcctgggct caagtgatcc   19680
tcctgcctca gcttcccaaa gtgctgggat tacaggtatg tgccatcgtc accagccaga   19740
atatgcattt tcttttttc agacggggtc tcactctgtt gcccaggctg gagtgcagtg   19800
gtgtgatctc agctcactgc aacctctgcc ttctgagttc aagcgattct cctgcctcag   19860
cctcccaagc agctaggatt acaggtgtct gccacaacac ccggctaatt tttgcatttt   19920
tagtaaagat ggggtttcac catgttggtc aggctgatca caactcccg actgcaagtg   19980 atccgcttac ctcggcctcc caaagtgtta ggattacagg catgagccat tgtgcctggc   20040
cgaatatgca cttttaataa gcatcagcca ggctaggcag gccgggggcc acactcgaga   20100
acatttgcac cacagccact ggctacctgc cccttttttcc ataaggttcc actgccctct   20160
ctcccctcta tctgggtctg ttcttcaggt tcttccctgg gagctctctg agtgacataa   20220
ctgtccccaa gtgctgggag atggagagag gaatcaccag actggagcag gcccccagag   20280
cggagatggg aagggaggc tggtgttctg aggctcccga ggcagtgaga ggtgaccgga   20340
ggcagtgaga ggtgaccgaa gacagtggct gagaaccagg gaggggctgc gggaaaaagc   20400
cctgggtgca agtcgctctt tccttagcgt ctttgagagg agggatgggg aaaggtgagg   20460
tactagggaa aaccatctgg aaggaggtca ggctgcagaa aagctgcagg agtctggggg   20520
actaagaaaa cagtgggaga cccgctgca gcccagcacg tgagggtgag aacgtcatga   20580
atgagggaag agcaggcagg gggtggtggc cttgtggcct ctggagagga ggagccacat   20640
gactctgggg tgatctgggg tgaccctcag ggtaagggta cctccctagc actgagtaca   20700
gagggaagcc tacactgcca ggtgcagttt ccctggcaat gcttctcctt ctaacactat   20760
```

-continued

```
gtgagtttcc tagtgctgct gtaacaaact gccataaacc aagtggcttc agagaacaca  20820
gacggactat gacagttgtg gagggaagaa gtttgaaaag cggggtgccc gcaggctgca  20880
gtgcttctgc aggctccagg gagaatctgg tccttgcctc ttccagcctc tagagcctgc  20940
cgcactcctt ggctcatggc cccgtgtcat tgtagcctct gcttctgcca tcacatctcc  21000
tcctctgcct ctcctgcctc cctctgtcct ttataagaac gcttttgagt atattggacc  21060
catctggata gtccaggata aatccctcca tcctcatatc cttaatttaa tcacacctgg  21120
aaggttccct ttgccacata aggtaacata ttcacattgg acagttaggg gattgggat  21180
gtggacatct tttgaggtgg aagaaggag  ctggggttct ttttaacatt ttttttgagac  21240
agggtctctg tcacctaggc tggagtgcag tggtgtgatt gagactcact gcagcagcct  21300
caacctcctg ggctcaagtg atcctcccac ctcagcttcc tgagtagctg ggactacagg  21360
tgtgcaccac catgcccaga tgattttttgt attattttaa tattttgtac acatggaggt  21420
ctttttaatgc tgcccaggct ggactcaaac tcctgggctc aagcaatcct cccgtcttag  21480
cctcccaaag tgctgggatt acaggtgtgt gccaccagac ccagcccgga cctgggttc  21540
ctgtctcatg tcagccttag caatctgggt gaccctgggc aaggcctatc ccctctctgg  21600
gcctttgttt ctccacctgt gcaatgaggc tgttccctct ggctccttca ctctgagttt  21660
ttcagttggg agaatatctt ggcagggagc agaggtcggc gggggtggtt gtcattccat  21720
ttcagggcct ctcagagtcc tgccgtggtg tgcactgtgt gtgtgtttaa ttttctacat  21780
ttggatgtga tcctaatcca ataaatgctt aggagacttc tatagaatag attaattttt  21840
actagaaaaa aatataattg gctgatgtta aggctactgc cctgacaaat ctgccttggc  21900
catatatctg agaaggtaaa agacccgcta cgcttgcaca taaatatgcc atcttcccca  21960
caggccctgg agaagcaccc cggggaggtt tcccttggtg atttattctt cattaataag  22020
ctctatgcta tattaggatc agatttatga ctctgccttt ctaatatttc tgacatttca  22080
tctgaaaaga attacaaatg aaatcttgaa actttgccac ttctccctgc tagtgctctg  22140
gcactctgtg tccaagggga gatggtgggc tggggagacc ccaagaagca gggacagagg  22200
catgtttctc agggaaagga gcgatcagct tgactttggg agagctttat tcagtttgca  22260
agcagcttgg gaggtgagcg gttcaggcga gaaggctgca gaccagacca caagcccagc  22320
agcagcagtg atgcctgtaa catgtatgag atggtggcag gcacattcat tcattcaaca  22380
gctatttgtt aagcacttta ctgtgtgcca aacactgtgc tgcttggtgc ttgggataca  22440
ggaaagaata aaagtgaagc agtgatgaag atcttggcct tcatgcatat ggtgttctag  22500
cagaggtagg ggagtgtcaa gcactgatga atgaaaatcc tgaataggta aaatatatca  22560
tatgttcaca cgtggtaagg gctatggcaa aacagaaaca aaccctccac acagggaaaa  22620
gggaaccaag agtgccgggt ggtcaagttg caatgttaat taagaaagca cttcaactca  22680
tcaactcaag gaaccgtatt atcccatttt tacagatgag acggaggct  cagcgtggat  22740
taggagctac acaaagacac aaagggaact ttgcacaact tgaaagtttg caaagtgccg  22800
tctgagccat tagtctccct tctccccact gactgcccta ccacaatcac atggggacca  22860
taaaaatact gttgcctggg tcccgctccc ctgaggcttt gattcaattg gtttggatgc  22920
agcctgggac ttggcatgtg actcttgtgg tgccaggact aagaatcttg tgtgaactcc  22980
cagcacagcc tctcaggcct ctattttctc acctgcaaga tgtgggtaaa atattcacc  23040
ctgtactgca agaggatgtc aggagtgaag gcagaaacac agcaccagcc ctccaggacc  23100
cccaacccct cccccacccc aatccttcac ccctgttgta ccttctgacc tcaaagtggc  23160
```

-continued

```
tctgattatt tcactcccac aggccactgg ctcagaggta tagagctcac ctgtggcaga    23220
tggagatgcg gatctgaggc ttctgatgct gccacaccca gcggcgcccc ccaaattccg    23280
ggcccctgga tgacatctgg tctgttcctg cagcatcaga gcacaataga gccagccacc    23340
agtcccagcc ctgcctgcat cccatccatt cctgggtgcc taaccccgag gatcccctgg    23400
cagtatgatg cggacctgtc ttggatccca gggatatgct ggccacgggg aggagccgga    23460
aaccaacctt tgtgtcactg tgtagtgaca agtgcctttg gaggtcacaa tagccagtgg    23520
tgatttctac cactgccccc agcagccaag gtggcagagg agccctgtca gtcaccccca    23580
ttctgttcat ggtctcacgg tgggctccac atgggggtg gcagccctct cccccacccc    23640
acccgacccc tttcgacaga tagggtaata caaatacaaa taacaccaaa agattgagtt    23700
gctgggcaga aagggaccaa aggccagtgt gtgtgtgagg ggtgggggca gggcaggaga    23760
ggagcagcaa aaggctgtga ccgcctggct gagcactgga tactcactga agggcaggga    23820
ggcttcctgg agaaggagac ctggcagggg ctgagggagt gatgccaggc atgggggttt    23880
ggagggaccc caggcatggc atgcctccat tcctccctgt gctatccact ctatataagg    23940
ggtgctgtgc agggagacag cttgcatcca agcagggagg cagggaggat gagaggcaga    24000
gaggagccca gctgggttga tggaaagtct gggaaatgca ggaaatccag gaggggaga    24060 atgattccaa gctgtggcct gtgatgggcc ttgaaaccag gtgtaggcac ttggatctga    24120
tcgctgggga gccagagctg cttcctgagc agcagaaggg caggatgcga atcagactag    24180
gggcagtggg aggaactgag aggcctcagg tcaccggaga aaatgcacag ggccgggagg    24240
cagagatgct cctgttttct tgctctgggg ctcaggacag tcagtcaccc tgagcttcag    24300
actcagctca ctcattttgc agagatcctg acggcgatgc ttcaggatga tctgggaaga    24360
gtcaatgagg taaaatatgt gaaatatgcc ttgaaaacta caaaccacag cacatgttct    24420 gttttttgctt ctgcttgatg gactcagtga gatggtgggg acaagaatta gagaagccca    24480
tgaggaggcc aagggcacc aaatagaccc accaaggacc agtggggact tagagaaagg    24540
atgagtcaga gagaaatgac aggagcagaa ggcaggcctt gtatggagga tgaaggtgaa    24600
gatcatacac cattaaactt gagaaagagg cgggaggagc tgccatttct tgagtctact    24660
ggatgccagc agtagtgctg ggcaagggct taacaggtgg ggaaatcgag gcacagagag    24720
gttaagtagc ttgcctaaga tcacccagtt agtaagtagc agagcctggc agcttaactc    24780 caaagtctttt gtactaaagc cagatttttcc aaatttgccc aactgtaaga atcacctggg    24840
cctgtaatcc tagcattttg ggaggctgag gtgggtggat cacctgaggt caggagtttg    24900
agaccagcct ggccaacatg gtgaaaccct gtctctacta aaaatacaaa caattagccg    24960
ggcgtggtgg caggtgcctg taatcctgta atcccagcta cttgggaggc tgaggcagga    25020
gaattgcttg aaccccaaag gtggaggttg cagtgagctg agattgcgcc atcgcactcc    25080
agcctgggca acaagagaga aacgccatct caaaaaaata aaagcccggg agtttattac    25140
agatgcatat tcccaggcac ctcctacgga ggttttgagt tagtgagtcc aaggccttct    25200
gcctcttccc aatgtattca ttatgcacca tcattactct tgttcagata caatgtgagt    25260
gatagcttgt ctctggcagc acagcagcca cacccaacca atccagacct cagtcatgag    25320
ggtgccaatc acagctaaca ttttttttttt tgagacggag tcttgctctg tcgcccaggc    25380
tggagtgcag tggcacgatc ttggttcact gcagcctctg cctcctgggt tcaagcgatt    25440
ctcctgcctc agcctcctaa gtagctggga ttacaggcac ctgccaccat gcccggctaa    25500
```

-continued

```
ttgtatttttt agtagagatg ggggtttcac tatgttggcc aggctggcct tgaactcctg   25560
accttgtgag ccacctgcct cagcttccca aagtgctggg attacaggtg tgagccaccg   25620
cacctggccc acatagctaa catttaatca gcacatacag ggccatgctc atcatttttt   25680
gcgcacaatg ccatttaacc ttcacaacag cctgtgagaa ggtgtgttag cctcatttta   25740
cagaggaaga aactaaggcc cagagaagtt atgcaacttg cccaaggaca cacagcttga   25800
aggagctgag gtttaacccg tttctacggg gtctgaatcc tccttaccac ccctatctcc   25860
cctgactccc aggttgtgtt tggtgtactt gggtagtgtc cagctgacaa atgagatgtt   25920
ttagcttcag acagtctatg ccatgtagaa atgcacccag gactgtgcat attagggagg   25980
tttgcaaatg tgtccacatt agataatttt tctcaaaatg cccctcactg aacttctgtc   26040
atgcagtatg tactgagcac ctgcctcttg ctaggtcccg ggagagagga tgaagagggc   26100
agagccccca ccctcagggg aacctgaaaaa tgggagtcct ttgtgctcat ggaagcaggg   26160
ccttggggcc tcagcactat ggacatttgg ggccgggtaa ttctttgttg tgggggggctg   26220 tcctgtagat tgcaggatgc tccgccgcat cccttgcccc tgccctctag aagccagtag   26280
caccctccag ttgtgaaagc cgtaaaatgt ctccagacat tgctcccagt tgagagccac   26340
ttcattaaag aaaaaaaaat aaaaaagatt tctgtatcct ctatacatgg actgaatttc   26400
actgacattt ctctaaaata actgaatcta tttctatact cattttttt taccagctgc   26460 cattttattt atttttcttt tctttctttt tttaagaaac agggtctcac tctgtcaccc   26520
aggctggagt gcagtggcgc aattatggct cactgcagcc tcgacctcct gggctcaagc   26580
aatcctccca cctagcgtc cccagtagct ggcacgccac tgtgcccggc tatttatttt   26640 atttttatttt atttttttg tggagacagg gtctcccaat gttgttcagg ctggtctcaa   26700
actcctgggt ttaagcaatt cttctgcctt catttcccag agtgttagga ttgcaggcgt   26760
gagccactgc acccggccat tttatttctt aacaaagcac aaatcaaatg tacaatgcag   26820
ctagattttc ctttataaat aatgtctaat ggatttgttt ctgtcagctg cctagaacat   26880
tctggtatcc cagacagaag tgcaacacca ggtggaggtg ttgcagctga gaagttctga   26940
ccagcatacc agcaccccct taaaagctgt ctatacttgc ggttctcagc taggctgcca   27000
cagaatcgcc caagtcttaa aaaacaggt ctctgtccta ctgcttgaga tgctggttct   27060
ctaggtctga ggttctggca cctgtgtgtt tttaaaactt tacaaataat ttaaaagcgc   27120
cttcaagtcc acaacaacag aatatttccc tccactcctc attgtcctgg agttctctaa   27180
cagtgcagtt ctacaactgg acacacgatg tcgcttttca gccacagttc tcactaagcg   27240
gccccacagg gcggcaggtg ccttctgcag agagagagag agggccttgg ctgacaggcc   27300
aagaccgggc atcctggctc ctcctctgta cagacttttc acagatgtga actctcccta   27360
ctccctgtct tctgccccca aatgaagcct ctcagctggc aagagctgag aactaccaag   27420
cgagccattg ctaatttcta ttgtgtttgg aaccacaaaa ggcagaatta ttaaggctgt   27480
aaaggacctc agagcatctg gtgcagtgag tttccaactt gtgaaaatct gatgtgatct   27540
cggacaagtc acttaacccc ctgcctcaat ttcttcatct gtaaatagg ataggaatat   27600 atcttgcccg tctgattgtt atgaagacaa agagaacaaa tgcacataaa gcccgtgacc   27660
atgtgctttg tgaatggaag ctttaattta ttcattcatt tatttattta tttattttta   27720
tttatttatt tattttgag acatagtctc gctctgttgc ccaggctgga gtgcaatggt   27780
gcgacctcgg ctcactgcaa cctccatctc ccggattcaa acaattctcc tgcctcagcc   27840
ttctgagtag ctgggattac aggtgcctgt caccatggcc agctagtttt tgtattttta   27900
```

```
gtagagactg ggtttcacca tgttggccag ggtggtctca aactcctgac ctcgtgatct   27960
gcccgctttg gcctcccaaa ggaagctttt atttttatta tagttttaca taaggataaa   28020
ttcagcctta gtgaagggaa gtgacttgcc caagatcata cagtgagact gctggatctg   28080
gggctctact tcagaatttt tttttgagat ggagtttcac tctgttgccc aggctggagt   28140
gcagtggcac aatctcggct cactgcaacc tccacctccc gggttcaagc gattctcctg   28200
cctcagcatc cctgatagct gggactacag gctcccacca ccacgcccag ctaattttta   28260
tattttgagt agagacaggg tttcaccatg ttggccaggc tggtctcaac ctgcctggcc   28320
tcccagagtg ctgagattac aggtgtgagc caccacgcca gtctactgcc attgtccatg   28380
atttttccta cagggaaaat cacaatccca gaagataaga caaagaacag taaaaggtgg   28440
cttttgaggc agtgagttct acctgaaggt gggaacagcc cagagtgtct ggggacagag   28500
tggtaaattc taatcaagcc ttcccatggc tttgtggatg aggatgagtt tctaccctga   28560
agctcggcct gttcagccat aaaatcagga taatggtggc tgtgcctcct tagagtagaa   28620
tgagaatcag agcagaacaa gggaaagctg cagtgacttg tcaggtgtca accttcagca   28680
tgatgggaga gccatgggac ccttcccctt tccctaagag agccagccct cacagcaggc   28740
ctgggatcca atgcccagca cccagctggg agcccaggga ccttggccaa aatctggttc   28800
tgcttcaact tggtgcccgg cctttgtcaa gtcacttcct catttgcaaa ctgggagagt   28860
ttggatgaaa ctattgaatg aaattatttt ggggtttct ttctggctct cacagtcctc   28920
gcatgctcac catgttccct tcaatttcat tagcacagcc caacaaaggg ttaagcagtg   28980
gcagttcctc tcgttctttg gttaggacag gaaggtcagg ggtgaggcca atacaagagg   29040
tagccgccac agctgatgct ggaaatgaca atagttcttt cctagactca tatttgtccc   29100
ctctccctga agctttgcct gcagtgccct tgtaaagaag ttggcaagaa gcaggagtga   29160
ggctcagccc ctctctgaaa tggatacgcc ggttgctccc cctcatggct ggtctcattt   29220
gccttcttca tttttagaca cattccaaac ttttcagcaa attatagtgt ttgccaactg   29280
gccgtctggg gcccaggaga gatgctattt atagcgatgc tgggatgctg ccatcccaga   29340
gcagcctggt aagaaacgga gccagagtgc ctggagtgg cgtcctgcac cctggggaga   29400
ggccagggcc ctggagcagg gtggcaaagc tggtggcccg tggcaaggac cactggcaca   29460
tcccctgcct gcctgggccc tggggtctgt gcccatacc cacacggggg gctgcttccg   29520
tgctccttgg agagacgatg gtgctgtggg gccactgagc acagtaaagg ctaagaccca   29580
ccataggtca gccctagtc atgctgactg ttgccccatt tcccttcatt ctctcactcg   29640
ttcattcctc agaatctgca tcctggtttt gtcactacct ggagttgtaa agataccacc   29700
aagctcacct tgtggtgtga gccttgattt tccccatctg tgtaaagggt ggatctgagc   29760
tccaaagttc cttctagtca tatgcagagt gcataataaa tgtgtttgta ttcccactgt   29820
gctcagtggg cactggggca tgcagaagag aaattggaat aaatgtgacc cttgtcctcc   29880
agaggctcag taccagactg gaaccaggac ccagatgagg ggcctaccca gagagggcag   29940
cgtgctctcc tatttgtgtt aggcgttacc atttacaaag ggctttacgg ctttgaaggt   30000
ccccacaacg ccctgaggag gtgaagtgtg gcaatgcccg ttcacttggg aaaatactgc   30060
atctcagaga gaccaaggga ctcgcttaag gtcacacaga tacagtaagt aagtagggaa   30120
agagctgggg cctctgggct ccttttccgg ggctctggcc tcggttttaa cccgttctcc   30180
tagacctctc agtctctggg cctcccctct gtgttcccca ccccactttt ccatcaagag   30240
```

-continued

```
ctcagttctc ttaagttcta tattctctct tccccacccc tagaaatctc tgcccgcttc     30300
cagaaaaggc tttgattccg tcattttggg catttcccac ccaggaatca aggctgcctc     30360
ctctgtgagg aaggcgtgtg gaaggcgagc agctgaggac acctcttttt aagagaagct     30420
tctccatgtt cttagccagg ttatataact tcttttgctt ctttcttttc cacattctac     30480 atattttca caatgaggat gtgtcacttc tatagttaaa aatggaaatc ttcatttaaa      30540
agaacaatca gacacaaggc aagtatgct  taccttccca atgaccaagg agcagggaga     30600
cattggtcgt ggaggccata ggtgaccagc cttgagggaa gggaaggaag gggaggtgca     30660
gggaggcgca gcagaggcac ccgagtgtgc tctacgaatg taagtctgcc agctgctcct     30720
ctgtgcctag caccctggaa agcgcccgca cacagtgggc cctcagcaaa ctcccactga     30780
gcaaagggcc ctgtgagtaa ggacctagaa gcaggtgtg  cttgaggcat ggggtgggag     30840
ggcatccagc ttggctggcg gtgggagccg atgcaaaggt gagctgagac cagacggtag     30900
aagaccttca gtgctgggcc gaggagggtt ccttcatccc atagagaaga gctgccatcc     30960
aagacagaag gctggggagt gacatgttga aatcagtatc ttaggaaaat aaagccactg     31020
gctgggccac tggctcccct ttgtagaggg gtctacgaag ctcccgaggt ttcagatagt     31080
ccctgagagc ccttcccctc gcgatgggct ccgtttgagg catgtccagt gtgaaaggac     31140
cacaggccac ctgagggaca ggaccaagca gagagctagt gacagaatgc ccagggctcc     31200
aagacagggc tggagaggtg ggagtggtcc ccaccttgag agccaaaggg gctgagggct     31260
gagggttgaa ggccgagagc caggaaggtc caggggagca aaaggggggag cagaggggga     31320 gctggaggtg ttggggtggt gggtagagag ccaagatagg gaggggacaa gagagggggag   31380 aatctcaagg aaaagcagga gcatgagact gagagaaggc ccctggaaca ctggcttgaa    31440
tgtggctgac attggcactg ccagtactca tcccaaacca gggagctcag ccagcgccct    31500
ttctgcatgt ccgctctttc atcagacagc taggaacaag ttatacgaga tgatgtccaa    31560
gtccaataaa tgtctaagtc ctttccactg gatctggccc cagcctcctc tctgaaccat    31620
ctcctatcac tccaccctat ccctgctggc tccttctgct ccagccatac aggcttgctc    31680
ctgggctcag cttgtgcctg cctggggagc ctcgcgcttg ctgtttcctc cttgagaaat    31740
tcctgccctg gataactcct tcccccactt ccttcagatc tctgctccct tatcaggggg    31800
cttcccctgg ctgccctatc tataacagcc ctgaccactc ttttcctctt ctcctgcttt    31860
ctttgtcttc ctgttcttat cactaagaca tcacacatgt cttagttggc ttgtttatat    31920
tctgtctcca cccatcttag tcagctactg ctgaaatgat gctgtgtaac aaaccacccc    31980
gatactcaga ggctccaaac aagtgctgat ctttctcatt tgtgagtctg tgtgtcagcc    32040
cgagcagggc agctccaggc tatggcttgg gtttgggtgg actccatgtc tctctccatt    32100
ctccttggac cagcagctcc ctggggcaca tgcttgtctt ggagaatggc aggaacttaa    32160
aagccaagcc aaacctcaca gcacggttaa gggtgatcat gacacaccgc taacattcta    32220
gtggccaaag aagtctcatg gccaagtgta atagcagtgg attgggcaag tttactctct    32280
tacacctgtt gtgaagggga gtgggagggg atggggggt  gaccgttttc acaacaacag    32340
tgcaaactat cccatctccc aatagaacat aaacaccttta aggttggaac tgggtctgta    32400
tccccagcac ttaaaatagt ttttggcata cagtaagggt gcaatagaca tttgttaaat    32460
aaatatacag actaaccaat tagcataata cagatgacaa aggtgtctct cttctgccag    32520
cttctgtgcc tgaaatgttg atgatctcct ccctatcttc taacatctc  tcctgtcccc    32580 acctgtccat gcccagggtt tggctgctgt gacagaagtg tgagagcctc ctgtctccct    32640
```

```
tgggatccca gtaagagctt ccatgcctct ctccctgctc acctgggctc ccatccctgg   32700
ggaccttctg gaaacagctt ccagggctcc cagagcttac ttagccagat tctacatctg   32760
gctccagctg ttatcctaag cttggccttg ttttctgatc tgaccacagc ttcatcactc   32820
ctacctgact gtgggattct agcccccagt ggggtggggg accaagggtg acaattacct   32880
gggaccttga ctattgaaag gctaatcagg tttgattggg aaaaaagagt tgctaaaaag   32940
gattgtattg gataattggt gagatttgaa catggatttt atattagtat tgtgttatta   33000
cattttctga tattagtcat tctttttttt tttttttttt gacggagttt gctctgtcac   33060
caggctggag tgcaatagtg tgatctcggc tcactgcaac ctctgccacc cgggttcaag   33120
cgattcccct gcttcggcct cctgagtagc tgggactaca gcgggtgcc accacaccca    33180 gcttgttttt gtacttttag tagagacagg gtttcaacat gttggccagg atggtctcga   33240
tctcttgacc tcgtgatctg cccgcctcag cctcccaaag tgctgggatt acaggcatga   33300
gtcaccgctc ccggccgtta gtcattctta taggtatgta agaaaatgtc cttgaggtat   33360
ttagcaggga agttcatgat ctctgcagct tactcacaaa tggttaaaca gaatgagact   33420
aagaacagac tagtaagaaa agactgaaga atataattat taggccaggt gcagtgactc   33480
acacctgtaa atcccaacat tttgggaagc tgagatagga ggatcacttg aggccaggag   33540
tttgagacca gcctgggcaa catagtgaga ccccatctct acaaaaaaaa aaaaagtaa    33600 aaattacgtg ggcacggtgg tatacgcctg tacttccagc ttcttgggag gctgaagtgg   33660
gatgatcaga ggacctcagg agtttgaggc tgcagtgagc tatgattgca gcactgcact   33720
ccagccaggg agacagactg aggcccggtc tctaaaaaaa aaggaatcta tgtgagtcta   33780
tatattcgtg caactttttct ataggattga aactcttttaa aataagctta ataataaaaa  33840
caaaagctgg tgggtgagac ctttcatgta ctctccagga gagttaagcc ccccaacatt   33900
cctgtcccct tgtttactct caagcacccc ctcccccacc caaggaccag gtctttgttt   33960
actgagcatc tcagcgatga gctctcaccc cctgatttca tcaattataa atgtgctcgc   34020
tactcaccac acggcaattt gtgacggact gtggtttgtg gtgagagtag caccatccaa   34080
gttcaccgca gccgcgagta gagatgaggg ttgggggccag acacagggct gtggggggcgg  34140 caagggcacg caggcagccc tgccaccttc ctgtttgtca gccaagtgag gcttccgagg   34200
gcagcgggcg agcgggtcac tactcagggc cagctactgc ggccaggcca ggctagtcag   34260
gtctgtgcag ccagaactag aggctccgcc aggatgtgag gtctcccagc tcctgggaac   34320
tgaagcaaac actctgacta ccccttcttg aagtgcctta cggtgtatac atttgtttaa   34380
tctgcacaac aaacctagga gcagttattg ttactgtcct catttttgcag atgaggaaac   34440 tgaggcaaag agaaattaag taactccttc aaagtctggt aagtgacaga accagatttt   34500
accctcttac tcattgtcca tattgccgag taacttacat taatagatac tatgcatgtt   34560 tatttttattt tttatttttt tttagagatg gggtctcatt ctttttttttt tttttttttg  34620 agacggagtc tcgctctgtc gcccaggctg gagtccagtg gggcgtgatc ttggctcact   34680
gcaagctccg cctccctggt tcactccatt ctcctgcctc agcctcccga gtagctggga   34740
ctacaggcac ctgccaccac gcccggctaa ttttttgtat atttagtaga gtcggggttt   34800
caccgcgtta ccagtatggt ctcgatctcc cgaactcgtg atccgcccac ctcggcctcc   34860
caaagtgctg ggattacagg cgtgagccac gcgcccggt cctcattctt tcactcagac    34920
tggagtgccg tcgtgcaatc tcagctcact gcagcctcaa ctcgggctc aagcaatcct    34980
```

-continued

```
gccacctcag cctcccgagt agctgggacc acaggcagtg ccaccacacc caactaattt   35040
ttgcattttt tgtagagacc ggcttttgcc atgttgccca ggctggtctc gaactcctga   35100
gctcagacaa tccacttgcc tcggcctcca aaagtgctgg gattatagca ccacgcccag   35160
ccgatactat gcatgtttaa ctgacaccta atgattaggt agcaacaatt tcttggctgc   35220
cttattcacc ttcatgaccc ccaacattga aaatgtcttt tcccatgtga aagcatttgt   35280
gggctcctac tgccaatcta taaagtagaa atccttctgt ggtacaaagc cctctttctt   35340
atctaatttc ccatttcccg ttccccttc ccccttctgc taagagctct tccctaccca    35400
cattgtaagt agggccgggg agctaactcc accttgcgta ctccaaatca accacatgac   35460
ccaggcctga ccaatcaggg ctccaaatcc tctagctata gtgattggtt tagggaggga   35520
catgtgaccc gcctgagcca atgaggatct gttctgggac tcctgtttga actcttggga   35580
aaataaactc cttatgttgg gtggctgagg ggatgaatgt gagctgggag ctgcaagcag   35640
gcatcatgct attcccttca gctttcaagt agtgttttca ctgctgttaa caattccaaa   35700
tcttaagtgt tccttgcatc ttcctctcgc caaaaatatt acagtactgg agggcttaca   35760
tggtgtctca aatgtctgga gtttaaatct gccttgcagc ttccatggcc acagtgagtg   35820
tctgagtcct ggccgctttc tgctgatccc ggggagagtt tagcctgcct gcccttcctc   35880
cctggttcgt tctcatgtac tcagatccct gcctcactct tctctcacac agacaacaaa   35940
agagagtcag attgtggtct taagtgcaca ggactctgaa gttaggacca gaagaccttg   36000
gttagagtct aaaccttgtc agttaccaaa tatcattagg cacattagtt aatctctctg   36060
aggcttattt ccccatcagt aaagtgggta ctgctgaaga tgtagtcttt agaagtgttc   36120
tctagattgt aagccccgtg cttcctggtt attgactaaa cagggataaa aatgagtttc   36180
tcctcacctg ggtgtcattg agtttctggt cattgtgaga tgggtgatga agccaagggc   36240
atcaaacatc ccaacgaggc tgttttctgc atctccaggg ctatcccagc gttaatcaca   36300
tatggacctt taatcagagt ttgcagaata agtgagaatt gtgttagagt atgaatgtag   36360
atattatctt gttttagtca ttgttactct aggggaccat tcttactaca ggaatattgc   36420
acaaacccca gaaatttatt gactttctcc taaccaaggc ctaaagagct ggtgttagac   36480
ataggccaag gccagccaga ggcccaaagc ctgtttccca gggtaggact gccctggcct   36540
ccccctcttt ctccccaggc tccaccccag agagctgaag accaggctgg gtacggcact   36600
gctgagaaac tgaggaaaag gccactggcc tcctctctca ctgcaggctg cccacccggg   36660
aggggggaaag cttgtcacta aatcaggttc agttttggtc actgtcttgg actggatatt   36720
ctagcatcag aactgagatg tttcttgtga cttaaagtaa cttcaggact ctattctacc   36780
taggattggg cagaaaagtt atgggcctgc gggagttcca attcagaaac aggggagatt   36840
acttgcacta aagaaagtct aaaggaaggt aggagacaaa aataaagttg tgtattgatg   36900
atcctaggag ttatgcttgt ttgacatacc agttatacct gctgtcacgg tagttatgca   36960
ttaggggacc caggtgtctg aagttatatc cagaagactt ctgagggtgc accgggggt    37020
cccttggcta aaagtgtgat ttaaacccta agagcctgcc cagactatca gtcccagttt   37080
ctacgtccac tgtccctgaa tctcgctgct tcttccttag gctgctggga gtctgaaccc   37140
tcccccgcca acacccctcc cccatgcctc agtcgtggga agggggggcc cttgagcagt   37200
agggccaagc cctgttcagc ctgggaccaa gttcccatca acaagtggt ctgggcagtg    37260
gccagccaga aagcagtaat tactgtcgag gtgcaggac cccaggtagg gccccacct     37320
cccacctctg tgtgggcagt gaatgggcct gccctgggt aaggctgtgt cagcaggcgc    37380
```

```
ctgcccaccc cttgctgggt tcccaggccc ctagagccct ctcgtaatag gagccatttg   37440
cgctgtaacc agtgggtgac cagattttta atcttggaga ccccttggat cccaggcggg   37500
aagtgggatt tgtcaaatgg ggagaggcgg ggctgtctgg gaatgccaga cggggttgtg   37560
ctggggaaat atgtctcctt tccatacagc ccccttccca tacctccagc ctccctctac   37620
cccgcaagtc agctctgtag ctcctaggag gtatctccaa catgcttagc tgttgaaagt   37680
aaatgaatgc cggaagttga aatctgaatg gcttgttttg cactaactca ggtgcatgcc   37740 aaatagggt gtctctttgc ttgatcctaa tccttcctcc tctgaaatcc tttctgacct    37800
gctgcctatc agcaattgcc ctgcaaagac cctctagctg gccgcgggag aagctgtgtt   37860
cttggctatc aggagtgaga acactggacc caagcttgcc tattctctgc cacaactcac   37920
tgtgtgatct tggacaagtc acttcctttc tttcagcctc agtttcagga acttggcac    37980 ttgctgagtg ccaatgtgtg ccatgttctt gacaagtatg gtcccacaca accttgccaa   38040
tgaccctgtg acctgtgtct tcttgttccc agtttacagg agagaagatg cagcctggga   38100
gagatgcagc agttgtctga ggccacacag caagtcaccc agggccagga tctgaagctg   38160
ggtctctcca gctccactgc ctgggcactt tctcctccac agcgaccttc aggtcatcat   38220
gaggagcctt tcggactaaa gctagagagc tgggattcca acagttcagc aacccatgac   38280
ttctccatgg cagctgctgc ctgaccacct agtgcctttc cactaagatt gttccttccc   38340
tctcctgaag attatcctcc tgcccctctc tcccaaacat ctgcggtgtg cacctgctgc   38400
ccaaagttga actttttttt gttagagaca gggcctcact gtgtcatcca ggctggagtg   38460
cagtggcgtg atcatagctc actgcagcct ccaactcctg ggctcaagtg accctctcac   38520
ctcagcttcc tgagtagctg ggactacagg catgcaccac cacgcctggc taattttaa    38580 attttttgca gagacagggt ctagctatgt tgcccaccct ggtcttgaac tcctgggctc   38640
aagcaatctg tctgccttgg tctcccagct cgctgggatt acaggcatga atcaccatgc   38700
ccggtcctcc aaagttgaac ttttgagact cagtttcctt cttggtaaat tcaggctcct   38760
aggtgctacc tcctcagaga catcctcctt gaccacatca catgacctct cgcagaggcc   38820
agattcttta atgtattcat ttgtctatta tcatgtttcc ccagtagaag ttgcacaaac   38880 ggcagggct tcatctgttt tgtttgccgt tatgtcctta gcacctaaaa ttgtgcctgg    38940
cacatatagt actcagtatg tatttgctgg gtcaatgagt gagtgaattt atactaataa   39000
cagcagctac catttctaga gtgtttacca tatattgggc actgtgtcag tcttcccaac   39060
aacccacaga cgaagatcaa ttattacacc cattgtacag atcaggaaac tgagtcaggt   39120
taagaaactt gccctaaatc ctacagtctc acttagaact tctgactgca gtgctcatca   39180
gaatgcattg tcaacccaaa ggtcatttcc agctcaggtg gcttctatca aaagagctca   39240
tcctggcctt tccaagagcc agacctccga catcggtgga gccctgtgca tagctggcct   39300
ctcctgggcg tcttgtccca agtacagaga cctggatcct ttcccactca tgtgcaacag   39360
cccaaaatta aaaacaaaag ccatattaaa aaacaaaacc aactttctgc cttaaaatat   39420
tgtgagccag ggggcaatta gcaattatgc tgtatttttat tatgagaaga tagaattcta   39480
attggactga tttgaattcc acacacctcc acagattgtt ttgggaatta aggtatcagt   39540
tgtatcggta attatggttt accattcaat taccccccca cagaaaactg ttaaattgtc   39600
tgtgacgggg cttaaattta gctcagacct atgtcctatg aagactgcgc gagtcaatac   39660
aagccatccg gaaaccaccg ggtgccctgt gccaggcggt aattagggt tgaggtttcc   39720
```

-continued

```
aaagttttac ctgagacagc agggacaagt gcctgggctg ggcgtgctca cgtgggggg      39780 cttggatgct cccccagcac agtgctcttg gctcctgccc tgcgttgctg gtgcaatagc      39840
tgatcatctg gaagacaatg tggtttcagc cgcaagtgac attttggcga ggtgcaccag      39900
catagaagcc ctgagacagc gagggaccat gtaaaactca cggacattgt aattggacac      39960
atctgggatt gaattcccac tcttccactt agggagtgaa cttgagaggg ccacttaata      40020
tctttgagcc tctgtttccc cacctgtcaa atgggtacac ctcctgcctc acacacgggt      40080
tattgtgaag atggatggag aataataatg gtgcctggcc caaattgcat tttttctct       40140 tttttagta ctcactacat gccagatact ttacaaacat ctctaaacct cctaagccct        40200
atagggcagg cactgtggtt attctctgtt ttatggatgg gaaaactgag tcccagagag      40260
gttaaataac atgccgaaag tcccatgact atgaaatggg gcagctggga tccaaaccca      40320
ggtgacctag ggccaaaccc taagcatgaa gctgccctgc tgggtgcctt ctgtacctgt       40380
ccctctaagt ggaagtgcct agaaatgacc cagccaaaag cagcagactg tattttatca      40440
tttcaacaat tctctctgtc cataaaaagt tctatgcagc ttggccagtt ccttttttcct      40500 gaatacaaaa ctgagaatgg taacagggaa ctgactttt aatgtcatgg tgcaaaggag       40560
ctagctctgc catgacctcc ttgaagtgac ctggtagagt gagggtaaga caagccacac      40620
tccctaggct atggaggcca ctctccatgg agataggga ataggaatc ctgcaaaata        40680 cagtctctgg ggatgggaag gatcaggaa ggggccaggt gcagtagctc atgcctgtaa        40740
tctcagcatt tcgggaggct gaggtgggag gatcgcttga gcccaggagt ttgagaccag       40800
cagtttgaga ccagcctgag caacatatca agaccctgtc tttacaaaaa attaacaaaa      40860
aggccaggcg tgatggctca cacctgtaac cccagtactt tgagaggccg aggtgggcgg       40920
atcacctgag gtcgggagtt tgagaccagc ctggccaacg tggtgaaact ccgtctctac      40980
taaaaataca aaaattagcc aggtgtggtg gctgtaatac cagctactcg ggaggctgag      41040
gcaggagaat cacttgaatc caggaggcag aggttgcagt gagcccagat catgccactg      41100
cactccagcc tgggagacag agtgagactc cgtctcaaaa aaaaaaaaa acaattaaca       41160 aattagatgg gtgtggtggt gcacagctgt agtcccagct actcaggagg ctgaggtgaa      41220
gggatcactt gatccaggtg ttcgaggcta tagtaagctg tgatcacccc actgcactcc      41280
agcctgggtg acagagtgag atcttgtctc aaaaaaaaaa aattttttt tttaaaggat       41340 cagggtaggg acatggactc ctcctattcc ttctggcacc atcagtggtt gaacacacaa      41400
actttggttc aaatcctgcc tcttccaatt tgctagctgt gtgaccttga aaaagttact      41460 taaccctct tatccttagt ttcctcatct tcagaataaa aatagtgctt gcctgatggg        41520
ggagatgatg gatgtaaagg gcctcataga gggcttggca tttaccaagt gtttgagaaa      41580
tattggctgt ttttattcaa ggcctgctca ttgctagcat gagctacctg caacagccac      41640
ctctaggcct cttttgctcc ctatagtcca gccacaccaa gaaaccatga tggcctgaat      41700
cctctctgac tttgtcaggc ctccgtgcct ttatacatgc tgttccttct gcctagaagg      41760
cctttctctt ttttcaacct ccttgagtcc attttagtcc ctgccagatg gtcacttctc      41820
tgtgatgctg ccctaactcc ttggcagcca tgctgctccc ttgaccattc actagccct       41880 ttaattcagc cccagccaca gtgaggatta atgggatga tgtctgagaa agcccatggg       41940
caagaacctg gcatggagtg gtgccccata aatgatgaat ggagctgggg ttgctttctc      42000
agccagctgc ctggcagggg cctggcttcc tcatcttcac acgtcagtgc ctagagtaac      42060
acctggcaca cagtgaacac aatctcagta actgttagac atttgtcttt tggggagctg      42120
```

```
ctcagcctcc cacattgggg tgtgggtttt ttgttttgtt ttgttttgtt ttttgagacg   42180
gagtttcatt cttgttgccc aggctggagt gcaatggtgc gatcttggct cactgcagcc   42240
tccgctgcct gggttcaagt gattctccta cctcagcctc ccgagtagta gctgggatta   42300
caggcacgtg ccaccatgcc tggctaatgt tttgtatttt tagtagagac aggatttcac   42360
catgttggtc aggctggtct tgaactcctg acctcaggtg atccaccgc cttggcctcc    42420 caaagtgctg agattatagg cgtgagccac cacgcccggc ctaggggtgt gggtcttt    42480 accgactagg cctggtgggg gaagtcaggg accccaccac aaaagttgga gaggccacat   42540
cctcccacct ccatctgggg ttagacatgt gacccaggct tggccaatcg gatgttcctc   42600
catcttgccc agaattcaca ctcagcagtg gtcttcacga ggggtggtag tggtggccag   42660
taggagcagg gctgggcagc ctccctaacc cacgttcatg agacttgaag ctggctggtt   42720
tcctgtcccc tggcctccct tgcccattcc catcctggtg ctccctccct atggactcct   42780
tttgctcata aatatccctc caattaattg ctttgctgct tcttagctag tgttgtttct   42840
gtcacttgca accaagagcc tattcaggtg caggaagggt tgaatgaaca atggaaatgg   42900
atcaacacat gtttctgagc atgtgctgac aggcaggccc tgggcggagt accacggtgt   42960
tcaaatgatg tgtaagatgt gggcagtgcc ccgggggtc tatggggaga cagaccatgc    43020
atgacatcat aaacaagacc acattataaa gtggggttta gttggacctt gcagacaccc   43080
agagaagacg actttgagcc ctcattggat ggtgccatcg caaagtacaa aacgaattgg   43140
gttgtaggaa ctggaggcac tgggacaata ttccagatta gggattgagc tgaagggtt    43200 ggaaatggct gagtagggtg gtggaaaggg atgcctgcta gtaggcaatt gtcttagtct   43260
gttttgtgct gctgtaatgg attaccacag actgggtaat ttataacaaa cagaaattta   43320
tttggctcat ggttctgaag gatgggaaat ccaaaatcaa ggagccggca tctggtgagg   43380
gccttcttgt tgcatcataa catgccagag ggtgtcacat ggtggaaggg caaagagagg   43440
gagaaaggga aagagaggga gcaggaaagg gcaaacccac tcccatgata taagctcac    43500 tcatatcatg agtcattcat ccatcgtgag ggcagggtcc acctcccaat accatcacaa   43560
tggcaactaa acctcaacat gatttttgga gaggacaaac attcaaacca tggcagcagc   43620
gtttgtggga aacacgcgcc aaagcaagaa aagaccaacc taagagtgag tgacttggct   43680
cctcattcta cattcatttt catccaatgg ggcccaaggg catgtaccca ttacccatct   43740
gggcagttcc cttgaatgtg ggcttctgtt tgcccgtgga ggtgaggaac ttcaaggaag   43800
aaaccatgaa agacctcttg aggctgaggg ctggcaccag caccaagatc tccaggcagc   43860
tggaacagtg atggctcctc cgtcctcgca ggcgggcac ccaacagggt gtgaccgtca    43920
cctgagggga gacagccaga ggcacaggcc tgatcctggg actgaggttg gcggtttggg   43980
tggagaggtg attctgagtg tgacaccctc cagtgataaa gtgggggct tcccagcagc    44040 ccctggggaa acaggctgca tctctggaga caggagatat gtggaggcct gagggcagt    44100 ggaaagccct gtgtgtctgg gtcaggtctc tccttggcag gtaatggttt gtcccagtag   44160
ttttcagact cccatcctg ccctgtcctt ctcctgtctg atgctcagac ctgtcactcc    44220
cagctcagcc cccaccttac tgtctacccc tcagagtccc tcccaccaag ggcaccttct   44280
gtcccacatc tccatggtgc agtcatggga ggagaacttg ggagcataag aaactccacc   44340
aagttggggc caggcatggt ggctcacgcc tgtaatccca gcactttggg aggccgaggc   44400
tggtgaatca caaggtcagg agtttgagac cagcctgacc aacataatga aatcccgtct   44460
```

```
ctattaaaaa tgcaaaaaat tagccgggca tggtggcagg tgcctgtaat cccagctact   44520
cacgaggctg aggcaggaga atcacttgaa ccgggaggca gaggatgcag tgagccaaga   44580
tcgcgccatt gcactccagc ctgggtggca gtgaaagact tggtctcaaa aaaaaaaaa    44640
aagaaagaaa gaaaaaaaaa gaaactccac caagggcttt tgggtcctag ggacagcaat   44700
gatgtggctg tccagccag aacctcattt tgtcagtaaa gttgggaccc atattcccta    44760
agagatttgt cccaagaaca catgggttgc tacagcggag gagaaatcaa gtctgttttc   44820
cctctggtga attgtcccct gaacgtgctt tcttcctaca gtgttgccag gaaagtaaaa   44880
aaaaaaaaaa aaaaaaaaaa aaagtccacg atgtcagctg gggtgatacc aaaacaattg   44940
tgggaggaac aacatccgca aattgaatag tgtgaggagt gtggacagaa gatgttttgt   45000
ctttggcctc atctcccaga cttgatcttt gtaaatacag aagtttccac cagagccgaa   45060
cctggcaatg acttgaggag cagctgcaag gaagacagcc tctcccaggg tatcacctgg   45120
gggcacaccc cagcttcccc tcctgagcct catcgagggg ttagtgctac ctctcgggaa   45180
aacataaaga tgacaagaag ccaaaggtgc caatagttcc catttagtat aaaagctggc   45240
tcagcaaatc atgctatttc agggcctagg gtgggccagt tcccaggcag ccctggcagg   45300
aaggactctg agaggcggac agtaaggtag gggcttggga gtgataggtc taaacatctg   45360
atggaagcaa aagggaggac aagggaggga gtcaaaaaat ccgggaagcc tgtccttcca   45420
gaaagtaccg acaccagggt gaggtggatc ccagcacccg cacctctgaa tggccttttcc  45480
cctgcacccc tatcccgccc ccactcggag ctaccccaag cacctgttcc tctgggcccc   45540
aaggtgacgc cctttgtgtg tgtataggaa aggacggtgt acacatttgg ttagttcctt   45600
cttttacacc ataaattatc agagacaacc cttttggaaa gcaatttggc aataatatca   45660
agtgacataa agatgttcat agcctttggc ccaataatct tcctcctggg aattaatcct   45720
aagaaaataa ttcacaagga agaaagaacc attttgtatc tacaaagaca tttattgggg   45780
tgttatttat gatagggaaa aactggagac accctcccca gccaacatag agggatggtc   45840
ctataaatta tgatacatcc atccaatgaa atgttaccct gccagtaaaa atggtaaatt   45900
gaaaattgtg tagcaacaag aaagagtgtt cagaaaataa aagcaagtga aaaaaggagc   45960
acaggattgt ctatatgctg tgatcaatgg caatgctgac aaatccatgt atgtgtagat   46020
agttgtagtg ttacctgtaa ggcacgataa ggcggatgta actgtgcttc aaatgttctt   46080
ttccatagct gtggagtcct tctagtatga aatcatttt gtaaaatcgc aatttgtcac    46140
cagggtttt gactttcctt attgcctcgt gggaggtggc agaggcagca catctcagac    46200
cgagcctcgg ttcctccccc tacctccac cgctgcgctt gaagaaagat gctgcagcct    46260
ccccagtccc catgccagcg ctcccacttt tctctgagct ttcggtggca gacagcgcct   46320
tgggcacttt ttcatgctca taattcgaat tacctgttta gtcggtcaa atgaaaaat     46380
accagctccg cccccacgcg ggctggccgg ggcgcctgga gcgccagggc ggctgcagcg   46440
cgctctccgc ggccgtcggc cctgagctca tttcctgggg cgcgcgcgcc gggctatttc   46500
agcctggcgc tgtgcaaaca ggacaattta ctgcggccaa aagggaccca aattacaatc   46560
gtatcacaga caaatatccg ccacgccagg tctccagggg ccaggagggg cctctctccc   46620
ggcgcggggg gcgggcgcgg ggtcaggcag gtccgcgggg ctcggctcgg cctcgccgtg   46680
ccctgatcgg cgtttgccac cgagctgtgc ctgctctctg caacaggaag gggcccagct   46740
ccccgggcg accgttccta tctgagttct cgttcctatc tgggttttcg tgcagaaaaa    46800
cttcatctct tcccagggat tttcccctga tttagggtcc ccttttattt ggtttctttt   46860
```

```
cagcacttgg gatgaaaaca tccctccatc cagccactcc agggctcaaa gtcatatctc    46920
ctcgttcaga aacctcagtg cctgtccacc actcttccgg aaaagtcgga atccttagtg    46980
tgatggtcaa agaccgctct tagtccagtc cacctgtcca gggccagccc ctgtacccag    47040
atgctccaac cacggagagc acatcagact ttcacaattt tatccttgac aattgccttt    47100
tcatcctgcc taaatgttcc cttgtttctt tctgcctagt gagctcttat tccttcttta    47160
agacccagat acacatcacc tcttccatga agccttccca gacttcccct ttccctgctt    47220
gacatctgcc ttccaagcag agtcagcccc ttttccttcc tagcaccgtg cagaggtaga    47280
tggtacttct cacatcctgt aattaattgc ttgcatgcct gtggtacacc gtaccattgc    47340
tcacaaatat ttcctcttcc tctctggaga aggattacac ttccttgatc cattggcctc    47400
actcaggctt cgccacatga ctggtgctgg ccagtgaagt gggacatgtg agttactggg    47460
gagcagaaac tttcaaagcc aagcatggct caccttgttc tctcttccct ctgttacaag    47520
gatggcagtg ccccagccag aaaccacact gccagcctgg cataggagtg gagcagggca    47580
cacataagtg tgagagaaat gaacttcacc tcagtgctcg aggcccctgg gaccatggac    47640
tcatttgtta ctgcagcata aactagctgg tcttgacttc agcttctgcc tctcttccct    47700
ggctttgcct tcacaaaatc aagagtctga tcttactcat attatagagc tggtcttcaa    47760
ccatgttctt tttttttttt tcctttttttt tttttgaga tggagtttcg ctcatgtagt    47820
ccaggatgga gtgcaatggt gcgatctggg ctcactgcaa tctctgcctc cctggttcaa    47880
gcgattctcc tgcctcagcc tcccaaatgg ctgggattac aggtgcttgc caccacgcct    47940
agctaatttt tgtattttta gaagagatag gatttcacca tgttggccag gctatctcaa    48000
actcctgacc tcaggagatc tgcccgcttc ggcctcccaa agtgctggca ttacaggcat    48060
gagccaccat gccagcccc atgttcttcg aatggccaag aatatcagta ggtaaggttt    48120
gttgagcatg gattgtgtgc caggtgctgt gctatgcctt tggcaagcgt tatcccatta    48180
catcctttaa cagcactctc tggtgggtac tgctcttata caagatttac aaaagagaaa    48240
agagactcag aggaatgtag gggctcacgt gagattgtaa agtagtgaga agtggagctg    48300
gtccttcagc tcaaatccct ctgatgccaa agaactcaaa ctctgcagtt ccatcatgtg    48360
catcctcact ctctcacttc ctgcagagga tctgtggagg ttgtaactat tgttttcacc    48420
tgtctcttcc actgggctct gagctgcccg aagacagatc ttttttttttt ttttgagaca    48480 gaattttgct cttgttgccc aggctggagt gcaatggcac gatcttggct caccacagcc    48540
tctgcctctt gggttcaagc gattctcctg cctcagcctc ccgagtaact gggattacag    48600
gcatgcgcca ccatgcctgg ctacttttgt attttttagta gagacgggt ttctctgtgt    48660 tggtcaggct ggtcttgaac tcccgacctt aggtgatctg tctgtctcgg cctcccaaag    48720
tgctgggatt ataggcgtga gccaccacgc ccggccccga agacagatct taatcatctg    48780
atttcccatc cattaattca gtctttcacc aaggatgtat tgagtgccaa ttatatgcca    48840
ggcatcatct gatgtgttgg ggacagagaa ataaaacaga taaaaatccc tgctgttaat    48900
tctagcctat ggtgacaaga agcagatccg tggctgcctg gggtgagtgt ggggtaggaa    48960
atgggagaaa tggggatgac tgcaactttg ggggtagtgg aaaatgttca gtatcgtggt    49020
agtggtggtg gctgtacagg tatatatatc cgcatacatc ccacagttca gaattataca    49080
ctttaaatgg taaatggata cagtttatta tatgtaaatg atccctcaat taagttgatt    49140
tagaggaacc tggccgggcg tggtggctca cacctagtat tctcagcact tgggaggcc    49200
```

-continued

```
gaggtgggcg gatcatgagg tcaggagata gagaccatcc tagctaacat ggtgaaaacc    49260
catctctact aaaaacacga aaacaaaaaa ttagccgggt gtggtggtgg gcgcctgtag    49320
tcccagctac tcgggacact gaacctggga ggcggagctg gcagtgagct gagatcgcac    49380
cacttcactc cagcctgggc aacagagcaa gactctgcct tgaaaaaaaa aaaaaaaaaa    49440
gaaccettgc tcttatggag aagcattcta ctggggaaaa cagacaataa acacatagat    49500
aaataaaaca tatgtcagaa aggggtaagt gatgctcaga aaataggac aagggatcag    49560
aagtgctagg cgttgcaatt taaaataatg gggtctggaa agccaccctg agaagggcca    49620
atggagctat gcccagcctg tggtatcctt cctcaggcag gggactgtac ccccagctta    49680
caagcctttt cgaggcacct tcagggtttg agcccaaaat gcactgcaca ttaagtgtta    49740
ttgatgggct tgtggaaatc tgctctccgt caggctctga tgaaacttttt ccaacaggag    49800
actgaactca gtactgggca tggcccccctg cacatagtaa gtccacagca aatgtgtgtg    49860
gggtgaatac tgtcttcttt atcctcccct tttctactcc agtccaggta gacggtgtat    49920
ctacccaccc aattttgctg tttctggtac cctcagtggg tcttgcctgc tcttcctcct    49980
tgaaatcatt actcagaggt ctccgtgtca gctccagaca gatgggcctg gtgctccttt    50040
atctcaatac aattccccgg ctcccaggct ccaggggaaa tcctgagcta actttggtct    50100
ttcctaaact ccacacttcc ctttgggcac ctctttcccc attgcggggc tcccttcag    50160
aatttgctgc tttatttatt tatttatttt tgtcagaggt gcattaatga tgctttattt    50220
aaaaacaaaa aacttggcca ggcgcggtgg cttatgcctg taatcccagc actttgggag    50280
gctgaggtgg gcggatcaca aggtcaggag atcaagacca tccagaccaa catggtgaaa    50340
cccagtctgt actaaaaata caaaaaaaaa aaaaaaaaa aatcagccgg gcgtggcaca    50400
tgcctgtaat cccagctact caggaggctg aggcaggaga tcacttgaa cccgggaggc    50460
agaggttgca gtgagccgag attgggccac tgcactccag cctgggtgac agagcgagac    50520
tccatctcaa acaaaaaaac accacaaata aataaaaat aaaacaaaa aaccaaaaac    50580
agtccattcc atgtcgtgtt gaaactgatc agtgtaagtt aaatggtggt ttttaggctg    50640
gacccatgat ttaagctgta cccatccagc tcaaactgaa aaaaaaaaaa atcatttgaa    50700
tgttaaagca atcgttcaga gtcttcaaga agaaccagg caggaaaatg ccaataatga    50760
tgactggcaa aatcaaaatc taaaacaaat aaactgttta tcaagctgcc gacagaaaaa    50820
gaaatcttgc atggagacta caagtctgga ttttctggga tgaaattgta caggaatctc    50880
agtctacagt ttcctcaatc gctgtggaga tggagctgtc actgaatctg acagagccct    50940
gcactcccca gtccgccgac cctttctgta atccagtctt cactgtagcc tgaggaacta    51000
tttcaacctg ctccttttttt atcttcttct ttggcacaac ctcagtggac ttctctgatt    51060
cagaacaagt tctaattgat cttctctgtt gcttctttc tactgagcct gtagaaccag    51120
atgttgcttc aagagatgat atattctgca ttggcttttc atttctctgg tttggtttag    51180
aaattataag cctgtcttgc cccctgacac ttatttctgt tttgttacca attcccttg    51240
ttgaataaac aaattaattt cccatcctct gtagcattct gaagagcaaa cacttcttca    51300
attttcacag ctggagacat gttacacttc tgcaaatcca ggctcccttt gtgcattgta    51360
atggaagctg gtaggatttc cttgctgcca cagttttcca ggctatttta acaggaggtg    51420
gctcttcctc gtccgcgctt gtgtgctgcc tcgggctgtg tctccaaatg tcagtacttg    51480
agagtgagga ggccacctcc cctgcattga tctgttctgg ctgagtttaa agcacagatc    51540
ttggtcatca ggttttttta acttcggctt tggagacaac attcttttt tttttttttt    51600
```

```
tagatggagt ctcgctctgt cgcccaggct ggaatgcagt ggtgcgatct ccggttcatg    51660
ccattctcct gcctcagcct cccgagtacc tgggattaca ggcgcccacc accatgccc     51719
```

<210> SEQ ID NO 3
<211> LENGTH: 492
<212> TYPE: DNA
<213> ORGANISM: Homo sapiens

<400> SEQUENCE: 3

```
ggtttcaact agttctggtg catagcagcc cccaaagttt tagcagcgtg gttagtggag      60
agctgtggct tttgcctcca tctaaatttt tctttgagca aattacctct ctcctgacag     120
ccctgttggg ggtgtcagtt gtggggttct ggtacctccc atcccggccc cagctagagc     180
aggcaggccc acaggaattt gaatctggag ggagttatca gtggtggagc gtagaggctg     240
caggaatctt catataagtg gagtcatata atatgtggtc ttttggtctg gcttctttac     300
ttagcatgct ttcaaggttc atccatgtcg tgggatatat tagtgcttca tttcacttct     360
gatggcaggg tcctgaatta agtcctgccc tgaggatcac actgttacat ctaggccttg     420
taggattcct gaaaattgca tcccatctgc cctgctctaa aatctacaca gcctttgcca     480
tatccattta tc                                                         492
```

<210> SEQ ID NO 4
<211> LENGTH: 557
<212> TYPE: DNA
<213> ORGANISM: Homo sapiens

<400> SEQUENCE: 4

```
ctagggctta gaagtttcct taacaccaac tgaggagtcc cagggtggga gctgagctca      60
cacgaagctc tacttcgcgt gtcctgaagc tttgacagtt gggcctcttt ctggcttttg     120
catcctctgc tcatactaag gccagcagag ctacaggttg gaccatggtc tggccgggag     180
ctccagcttc ctcttttcct ctcagtagtc atcgggccag ctgcccatac ctggtgccca     240
ggtatgagaa gagaccttg gctttcacca ggttcttgag agggtcaggg acctccaaaa      300
ggataaatgc cattggtcag atagtcactg tctacctccc tcccatccat ttcctgcctt     360
caacccctgt tcttgggaca aggccttcgc tggcattcaa tggcgggtcc ctgaggaagg     420
ccccagcctt gccgaacatc cttcaaggga gacttcagcc cctggccctg cagtgagtgt     480
gttgttagca gcagaggggc tgagtgaggc agtgggatgg ggcttttctt ttttgttctg     540
gttgcaaatt ataaacc                                                    557
```

<210> SEQ ID NO 5
<211> LENGTH: 819
<212> TYPE: DNA
<213> ORGANISM: Homo sapiens

<400> SEQUENCE: 5

```
gccttcagtt tgtcccgttc taaccgcccg gccgtctcaa tgcgatcaca ggagggacac      60
ggagatcgag gagggccaca gccggaccag gccaggcgtg ctgcggcagg aggaaggctc     120
cggaggtggg gtgggaaggg gaggccgaga gacgggtgtc gccgcgcccc cgctgccgcc     180
agagaggagc ctacggctgg cagcctggcc tgggcagcag ggtcctcggc gctcggctgg     240
gaaatcgcac gtctctccgc ggtgacctgt gcacagcccc tgggcctccg cctccgtgct     300
ggcagcctcc gcctcagcgc acaaagcccc gtcaccccga ctctcggagc gccgccgccg     360
```

```
ccaaatcctc agccctccc tcattggccg cggcgtctgc cgggaagtgc agtcccgggt    420
ttggggcgat ggagcccagg aggaagcggc gagtcagcgc ggcggagagg cggaggggga    480 cggaggggc ggaaggggac gaaccacgaa cgcccgcggc cgcgaaggt ctggacgaca    540 aaggagagac tagcgagagg gcttgttgct tttttttttt tttttttttt tttttttttt    600
gagacggagt ctcgctctgt cacccaggct ggagtgcaat ggcgcgatct cggctcgctg    660
caacctccgc ctcccgggtt caagcgattc tcctgcctca gcctccgagg agctgggatt    720 acggggcgc gcctccacgc ccagctaatt ctttgtactt ttagtagaga tgaggtttca    780
ccatgttggc caggctggta tcgaactcct gacctcgcg                           819

<210> SEQ ID NO 6
<211> LENGTH: 581
<212> TYPE: DNA
<213> ORGANISM: Homo sapiens

<400> SEQUENCE: 6
ccctgccatt ctggatagtt ttggttattt ttagtttaac ttcaggtgag ccactcttct     60
ttggaatcac agtttgtggt accgaagtgg tggctgtgga ggggaagggt tttctagaat    120
ttaatgtggt cttctgttta gaatttctga atggtaatag tcagtgggc taaagttttct   180 agctgcgcca aagtcattgg ctgacccatt aggatattga ttatgcgact ggtatttggt    240
ttgaatttca tacatgctga ttgatggcag gtagccattt gtgagtggag gaagatctgt    300
tgtaggtgag tattgaaagc tttgctgcaa ggtagcttcg tatggtgtct ggccaccatc    360
ttcagcaatg tcacttttgt tatcaaaggc atcctcctga cggatgctgg cggagtcagt    420
gagttgaggt ggttgttgaa ctgtgtttcc cgtgatccct tgcatgaaag agaaagagaa    480
atccattgtt ctgctccagc attcttaact ttccctttct ctcatcgggc cttcagtttg    540
tcccgttcta accgcccggc cgtctcaatg cgatcacagg a                        581

<210> SEQ ID NO 7
<211> LENGTH: 602
<212> TYPE: DNA
<213> ORGANISM: Homo sapiens

<400> SEQUENCE: 7
attccctaag agatttgtcc caagaacaca tgggttgcta cagcggagga gaaatcaagt     60
ctgttttccc tctggtgaat tgtcccctga acgtgctttc ttcctacagt gttgccagga    120
aagtaaaaaa aaaaaaaaaa aaaaaaaaaa agtccacgat gtcagctggg gtgataccaa    180
aacaattgtg ggaggaacaa catccgcaaa ttgaatagtg tgaggagtgt ggacagaaga    240
tgttttgtct ttggcctcat ctcccagact tgatctttgt aaatacagaa gtttccacca    300
gagccgaacc tggcaatgac ttgaggagca gctgcaagga agacagcctc tcccagggta    360
tcacctgggg gcacacccca gcttccctc ctgagcctca tcgagggtt agtgctacct    420 ctcgggaaaa cataaagatg acaagaagcc aaggtgcca atagttccca tttagtataa    480
aagctggctc agcaaatcat gctatttcag ggcctagggt gggccagttc ccaggcagcc    540
ctggcaggaa ggactctgag aggcggacag taaggtaggg gcttgggagt gataggtcta    600
aa                                                                   602

<210> SEQ ID NO 8
<211> LENGTH: 572
<212> TYPE: DNA
<213> ORGANISM: Homo sapiens
```

<400> SEQUENCE: 8

```
gagaggacaa acattcaaac catggcagca gcgtttgtgg gaaacacgcg ccaaagcaag      60
aaaagaccaa cctaagagtg agtgacttgg ctcctcattc tacattcatt ttcatccaat     120
ggggcccaag ggcatgtacc cattacccat ctgggcagtt cccttgaatg tgggcttctg     180
tttgcccgtg gaggtgagga acttcaagga agaaaccatg aaagacctct tgaggctgag     240
ggctggcacc agcaccaaga tctccaggca gctggaacag tgatggctcc tccgtcctcg     300
caggcggggc acccaacagg gtgtgaccgt cacctgaggg gagacagcca gaggcacagg     360
cctgatcctg ggactgaggt tggcggtttg ggtggagagg tgattctgag tgtgacaccc     420
tccagtgata aagtgggggg cttcccagca gcccctgggg aaacaggctg catctctgga     480
gacaggagat atgtggaggc ctgagggca gtggaaagcc ctgtgtgtct gggtcaggtc     540
tctccttggc agtaatggt ttgtcccagt ag                                   572
```

<210> SEQ ID NO 9
<211> LENGTH: 606
<212> TYPE: DNA
<213> ORGANISM: Homo sapiens

<400> SEQUENCE: 9

```
gaagcttctc catgttctta gccaggttat ataacttctt ttgcttcttt cttttccaca      60
ttctacatat ttttcacaat gaggatgtgt cacttctata gttaaaaatg gaaatcttca     120
tttaaaagaa caatcagaca caaggcaagg tatgcttacc ttcccaatga ccaaggagca     180
gggagacatt ggtcgtggag ccataggtg accagccttg aggaaggga aggaagggga     240
ggtgcaggga ggcgcagcag aggcacccga gtgtgctcta cgaatgtaag tctgccagct     300
gctcctctgt gcctagcacc ctggaaagcg cccgcacaca gtgggccctc agcaaactcc     360
cactgagcaa agggccctgt gagtaaggac ctagaagcag ggtgtgcttg aggcatgggg     420
tgggagggca tccagcttgg ctgcggtgg gagccgatgc aaaggtgagc tgagaccaga     480
cggtagaaga ccttcagtgc tgggccgagg agggttcctt catcccatag agaagagctg     540
ccatccaaga cagaaggctg gggagtgaca tgttgaaatc agtatcttag gaaaataaag     600
ccactg                                                               606
```

<210> SEQ ID NO 10
<211> LENGTH: 664
<212> TYPE: DNA
<213> ORGANISM: Homo sapiens

<400> SEQUENCE: 10

```
gccataaaat caggataatg gtggctgtgc ctccttagag tagaatgaga atcagagcag      60
aacaagggaa agctgcagtg acttgtcagg tgtcaacctt cagcatgatg ggagagccat     120
gggacccttc ccctttccct aagagagcca gccctcacag caggcctggg atccaatgcc     180
cagcacccag ctgggagccc aggaccttg gccaaaatct ggttctgctt caacttggtg     240
cccggccttt gtcaagtcac ttcctcattt gcaaactggg agagtttgga tgaaactatt     300
gaatgaaatt attttggggg tttctttctg gctctcacag tcctcgcatg ctcaccatgt     360
tcccttcaat ttcattagca cagcccaaca aagggttaag cagtggcagt cctctcgtt     420
ctttggttag acaggaagg tcaggggtga ggccaataca agaggtagcc gccacagctg     480
atgctggaaa tgacaatagt tctttcctag actcatattt gtccctctc cctgaagctt     540
```

| | |
|---|---|
| tgcctgcagt gcccttgtaa agaagttggc aagaagcagg agtgaggctc agccctctc | 600 |
| tgaaatggat acgccggttg ctcccctca tggctggtct catttgcctt cttcatttt | 660 |
| agac | 664 |

<210> SEQ ID NO 11
<211> LENGTH: 688
<212> TYPE: DNA
<213> ORGANISM: Homo sapiens

<400> SEQUENCE: 11

| | |
|---|---|
| tgcctagaac attctggtat cccagacaga agtgcaacac caggtggagg tgttgcagct | 60 |
| gagaagttct gaccagcata ccagcacccc cttaaaagct gtctatactt gcggttctca | 120 |
| gctaggctgc cacagaatcg cccaagtctt aaaaaaacag gtctctgtcc tactgcttga | 180 |
| gatgctggtt ctctaggtct gaggttctgg cacctgtgtg tttttaaaac tttacaaata | 240 |
| atttaaaagc gccttcaagt ccacaacaac agaatatttc cctccactcc tcattgtcct | 300 |
| ggagttctct aacagtgcag ttctacaact ggacacacga tgtcgctttt cagccacagt | 360 |
| tctcactaag cggccccaca gggcggcagg tgccttctgc agagagagag agagggcctt | 420 |
| ggctgacagg ccaagaccgg gcatcctggc tcctcctctg tacagacttt tcacagatgt | 480 |
| gaactctccc tactccctgt cttctgcccc caaatgaagc ctctcagctg caagagctg | 540 |
| agaactacca gcgagccat tgctaatttc tattgtgttt ggaaccacaa aaggcagaat | 600 |
| tattaaggct gtaaaggacc tcagagcatc tggtgcagtg agtttccaac ttgtgaaaat | 660 |
| ctgatgtgat ctcggacaag tcacttaa | 688 |

<210> SEQ ID NO 12
<211> LENGTH: 550
<212> TYPE: DNA
<213> ORGANISM: Homo sapiens

<400> SEQUENCE: 12

| | |
|---|---|
| caaagtggct ctgattattt cactcccaca ggccactggc tcagaggtat agagctcacc | 60 |
| tgtggcagat ggagatgcgg atctgaggct tctgatgctg ccacacccag cggcgccccc | 120 |
| caaattccgg gcccctggat gacatctggt ctgttcctgc agcatcagag cacaatagag | 180 |
| ccagccacca gtcccagccc tgcctgcatc ccatccattc ctgggtgcct aaccccgagg | 240 |
| atccctggc agtatgatgc ggacctgtct tggatcccag ggatatgctg gccacgggga | 300 |
| ggagccggaa accaaccttt gtgtcactgt gtagtgacaa gtgcctttgg aggtcacaat | 360 |
| agccagtggt gatttctacc actgcccca gcagccaagg tggcagagga gccctgtcag | 420 |
| tcaccccat tctgttcatg gtctcacggt gggctccaca tgggggtgg cagccctctc | 480 |
| ccccacccca cccgacccct ttcgacagat agggtaatac aaatacaaat aacaccaaaa | 540 |
| gattgagttg | 550 |

<210> SEQ ID NO 13
<211> LENGTH: 531
<212> TYPE: DNA
<213> ORGANISM: Homo sapiens

<400> SEQUENCE: 13

| | |
|---|---|
| ggatctccta cgtactgcta cgactgcaca caggtgcagg aaatggctgt ttgctttgcg | 60 |
| tttgaggaac ttggaaaggg agacgtggta gggaaagtag tggttagggg cactttcaga | 120 |
| ctgaaggatg tgggttgggg aatacgggat tcttggagtt gaggacgccg cttctctcgt | 180 |

```
ctctagctaa tgtgagaaag acccttctgg acactaagcc tgcaattcca ctggtggcta      240
ccaggtgtcc gtggtgtcct ggggcgggtg taatgagagc gggagcctgt gaaaccaaaa      300
gcattgtttt tataaattca gcactcttca atccctatta ataaggttag cggtgcagtt      360
cttgcgtctc ctgccctgcc tcaccttgca atcatattca ttggcattcc tttcttccaa      420
gaacccacct aggaggcctt gcaggagata tctctggtgc tggctgttcc tgcagtctga      480
aaagccagtt aagatacaaa tatgtgagag acactgcttg aatctgatt t                531

<210> SEQ ID NO 14
<211> LENGTH: 673
<212> TYPE: DNA
<213> ORGANISM: Homo sapiens

<400> SEQUENCE: 14
tgagggtaaa atgaaacaat aatcacgggt gcatcctgga gctctttctt acaaggcgtg      60
cccccaaatc tgtcccctct ttctgaggat gcccttcccc tattgtctcc ctggccattt      120
cctacccatt ctcaagggcc atgatctcag ggagttctcc tgactcaccc aggcatattg      180
gatctcctac gtactgctac gactgcacac aggtgcagga aatggctgtt tgctttgcgt      240
ttgaggaact tggaaaggga gacgtggtag ggaaagtagt ggttaggggc actttcagac      300
tgaaggatgt gggttgggga atacgggatt cttggagttg aggacgccgc ttctctcgtc      360
tctagctaat gtgagaaaga cccttctgga cactaagcct gcaattccac tggtggctac      420
caggtgtccg tggtgtcctg gggcgggtgt aatgagagcg ggagcctgtg aaaccaaaag      480
cattgttttt ataaattcag cactcttcaa tccctattaa taaggttagc ggtgcagttc      540
ttgcgtctcc tgccctgcct caccttgcaa tcatattcat tggcattcct ttcttccaag      600
aacccaccta ggaggccttg caggagatat ctctggtgct ggctgttcct gcagtctgaa      660
aagccagtta aga                                                          673

<210> SEQ ID NO 15
<211> LENGTH: 570
<212> TYPE: DNA
<213> ORGANISM: Homo sapiens

<400> SEQUENCE: 15
aaagacactg cagagaaaag aaagcacagc ctgctgccct gggaattaac atgatttagg      60
agacctgcag gtcaccccct catgactaaa agccatcctg gaatgaaggt ctgtggctat      120
ttctaggcaa aactgtctga taagataaaa tagctcaact cctgaccatt aagtcgtgaa      180
ggccatggcc atcgtaaatc tcatctttcc ggccctctgg cctgcatgca gtgcagccca      240
gccagtcggt ggcagccacc ttggtaggaa gggccctcat cctcctggct gtgcccaag       300 gactgggcag gcttcggtgc caagggtagt gcgagcactt gaaagccgcc ctgtatgttt      360
attgttttcc ccaggtgatc cagaattact cccgaactct accagctgaa atcctcctca      420
actcacatca gacaagacgg ccctgccact tacctgtcag atcactttgg caggtaagc       480 tcattttcct gaatctttac ttccacacct taaaatgtga gcaatactat ctccctggca      540
aggttgtttg tgagggtaaa atgaaacaat                                        570

<210> SEQ ID NO 16
<211> LENGTH: 517
<212> TYPE: DNA
<213> ORGANISM: Homo sapiens
```

<400> SEQUENCE: 16

```
actcctagaa ccctaaagga agcccctgga cacgcaggaa ggtgtggaga ggagttctca        60
tacttgcact tgggaggagg gctcaggaga aacagaggct ggcaacaccc cctcacacac       120
tggtcctctg gagggccagt gtctacagac actgtggact gagtccacag agaggaaagg       180
gtcctgcctt catcagaact gctcagcaag cagttccatc ccaggggtc ctgcgaggta        240
agggaggggc agctagctag gtgagggct gagagagtgg ggaggggaaa gagggaagaa        300
gagagtgaga gggagaggga gggactgagc cgattctcag ctccttgacc gtttgctgag       360
ctctgtctga gtggacagat ggtcccaagt caggccacac cagagtggcc tttctgctcc       420
cctacaccct gcattcctca acattgctgg ccccggagag actttccttc agagaagcaa       480
atggctgggg aatggtgaaa gacactgcag agaaaag                                517
```

<210> SEQ ID NO 17
<211> LENGTH: 586
<212> TYPE: DNA
<213> ORGANISM: Homo sapiens

<400> SEQUENCE: 17

```
gtatcaccag tgaagttggt gcacacagca gggcccaaac tgacatctca cagcacccag        60
caggtcactg tgggcatgat aggatgatgg gtcactgtgc cagccctgaa ggagttcaag       120
tccagatagg ggaaggtggt ggaccagacc cagacagaga ttctgagtcg ctgctgagac       180
tgggtgaggg tagtgggtac atgggaggac atatagcccg gcagcccagg gctggagtcc       240
acactcaggt tggggcagcc tggtctgcct ctcctgcagg agactttcc aggcaggctt        300
gtccctccag aatgcacgaa tcaaatcctc tcaggatcag tctcattttc ctcgtgctgg       360
gggagcaggc tactcacaga agatgttgtt gcaaatgtaa gaatcacatg tcgatccaca       420
aactggcatt gagcagctac ctaggagatc aaagaaactc ttactttggg agctcctgcc       480
agggctcttt gggaggtctg gctagctctg gaggaagaga atgaacttgg ggagggcgtg       540
gaacagatga ggacgcaggc actgccattc aaagaggaga ggtctc                      586
```

<210> SEQ ID NO 18
<211> LENGTH: 1100
<212> TYPE: DNA
<213> ORGANISM: Homo sapiens

<400> SEQUENCE: 18

```
cacagctgga gacatgttac acttctgcaa atccaggctc cctttgtgca ttgtaatgga        60
agctggtagg atttccttgc tgccacagtt ttccaggcta ttttaacagg aggtggctct       120
tcctcgtccg cgcttgtgtg ctgcctcggg ctgtgtctcc aaatgtcagt acttgagagt       180
gaggaggcca cctcccctgc attgatctgt tctggctgag tttaaagcac agatcttggt       240
catcaggttt ttttaacttc ggctttggag acaacattct tttttttttt tttttagat        300
ggagtctcgc tctgtcgccc aggctggaat gcagtggtgc gatctccggt tcatgccatt       360
ctcctgcctc agcctcccga gtacctggga ttacaggcgc ccaccaccat gcccggctaa       420
ttttttttgta ttttttagt agagacgggg tttcaccgtg ttagccagga tggtctcaat       480
ctcctgacct tgtgatccgc cgcctgggc ctcccaaagt gctgggatta cagacgtgag        540
ccaccgcgcc cggccccaac attcttttt gcttgggata aaccctcttc aggctgttaa       600
tcaatataga taaaagtata ctgttctatt cttttcttctc aagtcatttt caatgctttc     660
tctgcatggg caatgccaaa atcccattga gcatgttctc tctgaggtca gggtttccaa      720
```

```
atcttttgtt tctcagagtg attgctggct tgtttggttg cctcagccag taattcttca      780
taccgcttat gacctttata ctcctgtacc cattttcat gaacccacac cctctctggc       840
tgtttgctaa aacactggac atgatatttt cgggcacctc ctgtgttaat tttggtatga     900
acctccagct ggggatcact tcaatccata caaggccagc acggataggt tcccaccttg     960
gaccacacaa gatcaccaac ttgaaactta acaccgtgg acacttctgt tgttggaaca     1020
gaagatagta ttggctgaac tggggcttcc tcttttagta ctggatcttc ccttggtttt     1080
tctgatatgg tgtgaaccct                                                  1100

<210> SEQ ID NO 19
<211> LENGTH: 1236
<212> TYPE: DNA
<213> ORGANISM: Homo sapiens

<400> SEQUENCE: 19
gagctgagat cgcaccactt cactccagcc tgggcaacag agcaagactc tgccttgaaa      60
aaaaaaaaaa aaaagaacc cttgctctta tggagaagca ttctactggg gaaacagac      120 aataaacaca tagataaata aaacatatgt cagaaggggg taagtgatgc tcagaaaaat    180
aggacaaggg atcagaagtg ctaggcgttg caatttaaaa taatgggtc tggaaagcca    240 ccctgagaag ggccaatgga gctatgccca gcctgtggta tccttcctca ggcaggggac    300
tgtaccccca gcttacaagc cttttcgagg caccttcagg gtttgagccc aaaatgcact    360
gcacattaag tgttattgat gggcttgtgg aaatctgctc tccgtcaggc tctgatgaaa    420
cttttccaac aggagactga actcagtact gggcatggcc cctgcacat agtaagtcca     480 cagcaaatgt gtgtggggtg aatactgtct tctttatcct ccctttttct actccagtcc   540
aggtagacgg tgtatctacc cacccaattt tgctgtttct ggtaccctca gtgggtcttg   600
cctgctcttc ctccttgaaa tcattactca gaggtctccg tgtcagctcc agacagatgg    660
gcctggtgct cctttatctc aatacaattc ccccgctccc aggctccagg ggaaatcctg   720
agctaacttt ggtctttcct aaactccaca cttccctttg ggcacctctt tccccattgc    780
ggggctccct ttcagaattt gctgctttat ttatttattt attttttgtca gaggtgcatt    840 aatgatgctt tatttaaaaa caaaaaactt ggccaggcgc ggtggcttat gcctgtaatc    900
ccagcacttt gggaggctga ggtgggcgga tcacaaggtc aggagatcaa gaccatccag   960
accaacatgg tgaaacccag tctgtactaa aatacaaaa aaaaaaaaa aaaaaatca     1020 gccgggcgtg gcacatgcct gtaattccag ctactcagga ggctgaggca ggagaatcac   1080
ttgaacccgg gaggcagagg ttgcagtgag ccgagattgg gccactgcac tccagcctgg   1140
gtgacagagc gagactccat ctcaaacaaa aaacaccac aataaataa aaaataaaaa     1200 caaaaaacca aaacagtcc attccatgtc gtgttg                                1236

<210> SEQ ID NO 20
<211> LENGTH: 1171
<212> TYPE: DNA
<213> ORGANISM: Homo sapiens

<400> SEQUENCE: 20
accgtgcaga ggtagatggt acttctcaca tcctgtaatt aattgcttgc atgcctgtgg      60
tacaccgtac cattgctcac aaatatttcc tcttcctctc tggagaagga ttacacttcc   120
ttgatccatt ggcctcactc aggcttcgcc acatgactgg tgctggccag tgaagtggga    180
```

-continued

```
catgtgagtt actggggagc agaaactttc aaagccaagc atggctcacc ttgttctctc    240
ttccctctgt tacaaggatg gcagtgcccc agccagaaac cacactgcca gcctggcata    300
ggagtggagc agggcacaca taagtgtgag agaaatgaac ttcacctcag tgctcgaggc    360
ccctgggacc atggactcat tgttactgc agcataaact agctggtctt gacttcagct     420
tctgcctctc ttccctggct ttgccttcac aaaatcaaga gtctgatctt actcatatta    480
tagagctggt cttcaaccat gttcttttt tttttttcct tttttttttt ttgagatgga    540
gtttcgctca tgtagtccag gatggagtgc aatggtgcga tctgggctca ctgcaatctc    600
tgcctccctg gttcaagcga ttctcctgcc tcagcctccc aaatggctgg gattacaggt    660
gcttgccacc acgcctagct aattttttgta tttttagaag agataggatt tcaccatgtt    720
ggccaggcta tctcaaactc ctgacctcag gagatctgcc cgcttcggcc tcccaaagtg    780
ctggcattac aggcatgagc caccatgccc agcccatgt tcttcgaatg gccaagaata     840
tcagtaggta aggtttgttg agcatggatt gtgtgccagg tgctgtgcta tgcctttggc    900
aagcgttatc ccattacatc ctttaacagc actctctggt gggtactgct cttatacaag    960
atttacaaaa gagaaaagag actcagagga atgtaggggc tcacgtgaga ttgtaaagta   1020
gtgagaagtg gagctggtcc ttcagctcaa atccctctga tgccaaagaa ctcaaactct   1080
gcagttccat catgtgcatc ctcactctct cacttcctgc agaggatctg tggaggttgt   1140
aactattgtt ttcacctgtc tcttccactg g                                  1171

<210> SEQ ID NO 21
<211> LENGTH: 1007
<212> TYPE: DNA
<213> ORGANISM: Homo sapiens

<400> SEQUENCE: 21 acgtgtaca catttggtta gttccttctt ttacaccata aattatcaga gacaaccctt      60
ttggaaagca atttggcaat aatatcaagt gacataaaga tgttcatagc ctttggccca    120
ataatcttcc tcctgggaat taatcctaag aaaataattc acaaggaaga agaaccatt     180 ttgtatctac aaagacattt attggggtgt tatttatgat agggaaaaac tggagacacc    240
ctccccagcc aacatagagg gatggtccta taaattatga tacatccatc caatgaaatg    300
ttaccctgcc agtaaaaatg gtaaattgaa aattgtgtag caacaagaaa gagtgttcag    360
aaaataaaag caagtgaaaa aaggagcaca ggattgtcta tatgctgtga tcaatggcaa    420
tgctgacaaa tccatgtatg tgtagatagt tgtagtgtta cctgtaaggc acgataaggc    480
ggatgtaact gtgcttcaaa tgttcttttc catagctgtg gagtccttct agtatgaaat    540 cattttgta aaatcgcaat ttgtcaccag gggttttgac tttccttatt gcctcgtggg     600
aggtggcaga ggcagcacat ctcagaccga gcctcggttc ctccccctac ctcccaccgc    660
tgcgcttgaa gaaagatgct gcagcctccc cagtcccat gccagcgctc ccacttttct     720
ctgagctttc ggtggcagac agcgccttgg gcacttttc atgctcataa ttcgaattac     780
ctgtttaagt cggtcaaatg aaaaaatacc agctccgccc cacgcgggc tggccggggc     840 gcctggagcg ccaggcggc tgcagcgcgc tctccgcggc cgtcggccct gagctcattt     900
cctggggcgc gcgcgccggg ctatttcagc ctggcgctgt gcaaacagga caattactg     960 cggccaaaag ggacccaaat tacaatcgta tcacagacaa atatccg                 1007

<210> SEQ ID NO 22
<211> LENGTH: 198
```

```
<212> TYPE: DNA
<213> ORGANISM: Homo sapiens

<400> SEQUENCE: 22
ggctggagca gggacttgaa aaagggagag ggctcaggag actcagagga ggaggaaagt    60
gtgtgagcag taggcagggt gtgtgtgtgt gtgtgtgtgt gtgtgtgtgt gtgtgcacgc   120
gcgcgcatgc aggcctgtgt agggctggga agaacaaag caaaagggtg cacaaggcat    180
ccagaagcca gggcaatg                                                 198

<210> SEQ ID NO 23
<211> LENGTH: 369
<212> TYPE: DNA
<213> ORGANISM: Homo sapiens

<400> SEQUENCE: 23
gagcagaagg ccttgactga gccccaggag aggcaggaca ccagggtgc acacccataa     60 acacacacat acacatgtat gtctcctccc tggagcctga gagtccctat atacagcagg   120
tgcatgtggg ccacacatca cacaaaattg aatacaggg ggctcagagc accagcacac    180
acgtatgtcc ttgacaccct tagagatact actaagcacg tgtgtgtacc tgctcaccca   240
tatggcagag cccctggatc tgggcagaaa tgccaaagca ggggcaggcg cgtgtgcgcg   300
cacacacaca cacacacaca cacacacaca ctagcacagc cacaaaagct caatccacat   360
ccagcattc                                                          369

<210> SEQ ID NO 24
<211> LENGTH: 436
<212> TYPE: DNA
<213> ORGANISM: Homo sapiens
<220> FEATURE:
<221> NAME/KEY: misc_feature
<222> LOCATION: 121,153
<223> OTHER INFORMATION: n = A,T,C or G

<400> SEQUENCE: 24
tcaggacgtt gcactttgac agaaggctct ggaaggaaac tttaaaggga gccttccaga    60
gggaaatgcg gtgttggggt aggtctgcct ttggctatgg gctttctggc tgccggaggg   120
ncccagggtc ccccaggaaa gccttctgtg ganggtcttt tgagagagac aaagcagagg   180
ggtggaggaa gggcggctca ggtggaagga gtgaggacaa aggtgagtgc ccctgggcag   240
gaagtgctga aagagagaag gagggaggcc accaggcctg ggcctggagc cagcctggga   300
gactcccagc cgcccacttc tcggggcctc cctttccag ccccttgctt tcgaggcagc    360
agtgccatta tttggggaaa ccagctaacc agataggaca gcaaaccggg gatttatgtg   420
gtgtgggaac agctca                                                  436

<210> SEQ ID NO 25
<211> LENGTH: 670
<212> TYPE: DNA
<213> ORGANISM: Homo sapiens

<400> SEQUENCE: 25
ctgggattac aggtgtctgg caccatacct agctaatttt tgtattttta gtagagatgg    60
ggtcttgcca tgttggccag actggtttcc aactccccac ctcaggtgat ctgcccgccc   120
tggcctccca agtgctggg attacgggca tgagccactg tgcctgacct cagctctgtt    180
attaataagc taaatggctt tgagcgactt gccttatcac ttgagcctca gtttcctcat   240
```

```
ctgtaaaatg gggataaact tcttccgtcc gcatgaggat gctgagagac gtgagtgagg      300
tggtctatga aagctcttgt catagcctgg catgcagggg taacatctgg atgatgaaga      360
tgatgatacc tgagattttt gccttacaga caactccaga gagccctgtg aaatatttat      420
atgccactga acagggcaca agatgaagcc attagcctgc gcttacatag tagaatgtgt      480
gaatcagatg agatgcttgg tctctagtaa gaccttaagg gatggacaga agacaggcag      540
attttggata tggtatacgt ggctgtgggc tagcgtgttt actactgggc tgggatgta       600 tttggaatgt acacatgtgt cctttgcttc tcagaacact tgaggcagc agagttacta      660 ctgcctgcca                                                             670

<210> SEQ ID NO 26
<211> LENGTH: 460
<212> TYPE: DNA
<213> ORGANISM: Homo sapiens

<400> SEQUENCE: 26
gaggttagac gggtctgagt tcaagcccca ggtctgccac ttcctggctg tgtgccctgg       60
aacaagtcac cttatctctc tgaacttctt ttttttttt ttcttttttga gatggagtct      120 cgttctgtcg cccaggctgg agtgcagtgg catgatctca gctcactgca agctccgcct      180
cccgggctca cgccattctc ttgcctcagc ctcccgagta gctgggacta caagcacccg      240
ccaccacgcc cggctaattt tttgtatttt ttagtagaga cggggtttca ccgtgttagc      300
caggatggtc tcaatctcct gacctcgtga tccgcccgcc tcggcctccc aaagtgctgg      360
gattacaggc atgagccacc atgcctggcc atctctctga acttctgttt cctcatctga      420
gatgacagtc agagtgggat ctgtgtaagg cactttgcac                            460

<210> SEQ ID NO 27
<211> LENGTH: 482
<212> TYPE: DNA
<213> ORGANISM: Homo sapiens

<400> SEQUENCE: 27
tgccaattag ccacactctt ctctagagag gtttcaagtc attttcttc acagcaatgg        60 caaggctctt aaataaggtc cttgaagttt cttcgggtct cctcccacct gctccctgcc      120
cccttcacct ccacccacct gcttcccttt ctcatccccc agaggcggag gcttccgagg      180
aatttggggt agggaaatag gaatcagggg ctcctcattc cccaaaggag cctctttggc      240
aagcaggcac gtgggtctcc gggctggtgc acatcacagg gcagccagcc caagtgccat      300
cttgatgccc aatcagtctt cctcatggct gcgccctgct ggtctctcag agggttaatg      360
caatttcttg gaggacgaca ttcctaacac ccaggggcca gaactccttc cccactggtt      420
attcccatgg cccagagcag caggatgggg gcagaaacag gcatggacct taacagcagc      480
gt                                                                     482

<210> SEQ ID NO 28
<211> LENGTH: 16
<212> TYPE: DNA
<213> ORGANISM: Artificial Sequence
<220> FEATURE:
<223> OTHER INFORMATION: PCR primer

<400> SEQUENCE: 28
attggcctgg cttctg                                                       16
```

```
<210> SEQ ID NO 29
<211> LENGTH: 16
<212> TYPE: DNA
<213> ORGANISM: Artificial Sequence
<220> FEATURE:
<223> OTHER INFORMATION: PCR primer

<400> SEQUENCE: 29
ggctggagca gggact                                                         16

<210> SEQ ID NO 30
<211> LENGTH: 20
<212> TYPE: DNA
<213> ORGANISM: Artificial Sequence
<220> FEATURE:
<223> OTHER INFORMATION: PCR primer

<400> SEQUENCE: 30
tcctgtgatc gcattgagac                                                     20

<210> SEQ ID NO 31
<211> LENGTH: 21
<212> TYPE: DNA
<213> ORGANISM: Artificial Sequence
<220> FEATURE:
<223> OTHER INFORMATION: PCR primer

<400> SEQUENCE: 31
ccctgccatt ctggatagtt t                                                   21

<210> SEQ ID NO 32
<211> LENGTH: 20
<212> TYPE: DNA
<213> ORGANISM: Artificial Sequence
<220> FEATURE:
<223> OTHER INFORMATION: PCR primer

<400> SEQUENCE: 32
cagtggcttt attttcctaa                                                     20

<210> SEQ ID NO 33
<211> LENGTH: 20
<212> TYPE: DNA
<213> ORGANISM: Artificial Sequence
<220> FEATURE:
<223> OTHER INFORMATION: PCR primer

<400> SEQUENCE: 33
gaagcttctc catgttctta                                                     20

<210> SEQ ID NO 34
<211> LENGTH: 20
<212> TYPE: DNA
<213> ORGANISM: Artificial Sequence
<220> FEATURE:
<223> OTHER INFORMATION: PCR primer

<400> SEQUENCE: 34
gtctaaaaat gaagaaggca                                                     20

<210> SEQ ID NO 35
<211> LENGTH: 20
<212> TYPE: DNA
<213> ORGANISM: Artificial Sequence
<220> FEATURE:
<223> OTHER INFORMATION: PCR primer
```

<400> SEQUENCE: 35
ttaagtgact tgtccgagat					20

<210> SEQ ID NO 36
<211> LENGTH: 20
<212> TYPE: DNA
<213> ORGANISM: Artificial Sequence
<220> FEATURE:
<223> OTHER INFORMATION: PCR primer

<400> SEQUENCE: 36
caactcaatc ttttggtgtt					20

<210> SEQ ID NO 37
<211> LENGTH: 20
<212> TYPE: DNA
<213> ORGANISM: Artificial Sequence
<220> FEATURE:
<223> OTHER INFORMATION: PCR primer

<400> SEQUENCE: 37
aaatcagatt caagcagtgt					20

<210> SEQ ID NO 38
<211> LENGTH: 20
<212> TYPE: DNA
<213> ORGANISM: Artificial Sequence
<220> FEATURE:
<223> OTHER INFORMATION: PCR primer

<400> SEQUENCE: 38
tcttaactgg cttttcagac					20

<210> SEQ ID NO 39
<211> LENGTH: 20
<212> TYPE: DNA
<213> ORGANISM: Artificial Sequence
<220> FEATURE:
<223> OTHER INFORMATION: PCR primer

<400> SEQUENCE: 39
attgtttcat tttaccctca					20

<210> SEQ ID NO 40
<211> LENGTH: 20
<212> TYPE: DNA
<213> ORGANISM: Artificial Sequence
<220> FEATURE:
<223> OTHER INFORMATION: PCR primer

<400> SEQUENCE: 40
gccataaaat caggataatg					20

<210> SEQ ID NO 41
<211> LENGTH: 20
<212> TYPE: DNA
<213> ORGANISM: Artificial Sequence
<220> FEATURE:
<223> OTHER INFORMATION: PCR primer

<400> SEQUENCE: 41
tgcctagaac attctggtat					20

<210> SEQ ID NO 42
<211> LENGTH: 20

```
<212> TYPE: DNA
<213> ORGANISM: Artificial Sequence
<220> FEATURE:
<223> OTHER INFORMATION: PCR primer

<400> SEQUENCE: 42
caaagtggct ctgattattt                                              20

<210> SEQ ID NO 43
<211> LENGTH: 20
<212> TYPE: DNA
<213> ORGANISM: Artificial Sequence
<220> FEATURE:
<223> OTHER INFORMATION: PCR primer

<400> SEQUENCE: 43
ggatctccta cgtactgcta                                              20

<210> SEQ ID NO 44
<211> LENGTH: 20
<212> TYPE: DNA
<213> ORGANISM: Artificial Sequence
<220> FEATURE:
<223> OTHER INFORMATION: PCR primer

<400> SEQUENCE: 44
tgagggtaaa atgaaacaat                                              20

<210> SEQ ID NO 45
<211> LENGTH: 20
<212> TYPE: DNA
<213> ORGANISM: Artificial Sequence
<220> FEATURE:
<223> OTHER INFORMATION: PCR primer

<400> SEQUENCE: 45
aaagacactg cagagaaaag                                              20

<210> SEQ ID NO 46
<211> LENGTH: 20
<212> TYPE: DNA
<213> ORGANISM: Artificial Sequence
<220> FEATURE:
<223> OTHER INFORMATION: PCR primer

<400> SEQUENCE: 46
cttttctctg cagtgtcttt                                              20

<210> SEQ ID NO 47
<211> LENGTH: 20
<212> TYPE: DNA
<213> ORGANISM: Artificial Sequence
<220> FEATURE:
<223> OTHER INFORMATION: PCR primer

<400> SEQUENCE: 47
gagacctctc ctctttgaat                                              20

<210> SEQ ID NO 48
<211> LENGTH: 20
<212> TYPE: DNA
<213> ORGANISM: Artificial Sequence
<220> FEATURE:
<223> OTHER INFORMATION: PCR primer

<400> SEQUENCE: 48
```

```
ggtttcaact agttctggtg                                              20

<210> SEQ ID NO 49
<211> LENGTH: 20
<212> TYPE: DNA
<213> ORGANISM: Artificial Sequence
<220> FEATURE:
<223> OTHER INFORMATION: PCR primer

<400> SEQUENCE: 49
ctagggctta gaagtttcct                                              20

<210> SEQ ID NO 50
<211> LENGTH: 20
<212> TYPE: DNA
<213> ORGANISM: Artificial Sequence
<220> FEATURE:
<223> OTHER INFORMATION: PCR primer

<400> SEQUENCE: 50
actcctagaa ccctaaagga                                              20

<210> SEQ ID NO 51
<211> LENGTH: 20
<212> TYPE: DNA
<213> ORGANISM: Artificial Sequence
<220> FEATURE:
<223> OTHER INFORMATION: PCR primer

<400> SEQUENCE: 51
gtatcaccag tgaagttggt                                              20

<210> SEQ ID NO 52
<211> LENGTH: 20
<212> TYPE: DNA
<213> ORGANISM: Artificial Sequence
<220> FEATURE:
<223> OTHER INFORMATION: PCR primer

<400> SEQUENCE: 52
gataaatgga tatggcaaag                                              20

<210> SEQ ID NO 53
<211> LENGTH: 20
<212> TYPE: DNA
<213> ORGANISM: Artificial Sequence
<220> FEATURE:
<223> OTHER INFORMATION: PCR primer

<400> SEQUENCE: 53
ggtttataat ttgcaaccag                                              20

<210> SEQ ID NO 54
<211> LENGTH: 20
<212> TYPE: DNA
<213> ORGANISM: Artificial Sequence
<220> FEATURE:
<223> OTHER INFORMATION: PCR primer

<400> SEQUENCE: 54
attccctaag agatttgtcc                                              20

<210> SEQ ID NO 55
<211> LENGTH: 20
<212> TYPE: DNA
<213> ORGANISM: Artificial Sequence
```

```
<220> FEATURE:
<223> OTHER INFORMATION: PCR primer

<400> SEQUENCE: 55
gagaggacaa acattcaaac                                              20

<210> SEQ ID NO 56
<211> LENGTH: 20
<212> TYPE: DNA
<213> ORGANISM: Artificial Sequence
<220> FEATURE:
<223> OTHER INFORMATION: PCR primer

<400> SEQUENCE: 56
tttagaccta tcactcccaa                                              20

<210> SEQ ID NO 57
<211> LENGTH: 20
<212> TYPE: DNA
<213> ORGANISM: Artificial Sequence
<220> FEATURE:
<223> OTHER INFORMATION: PCR primer

<400> SEQUENCE: 57
ctactgggac aaaccattac                                              20

<210> SEQ ID NO 58
<211> LENGTH: 20
<212> TYPE: DNA
<213> ORGANISM: Artificial Sequence
<220> FEATURE:
<223> OTHER INFORMATION: PCR primer

<400> SEQUENCE: 58
agagagggtg agtaacttcc                                              20

<210> SEQ ID NO 59
<211> LENGTH: 20
<212> TYPE: DNA
<213> ORGANISM: Artificial Sequence
<220> FEATURE:
<223> OTHER INFORMATION: PCR primer

<400> SEQUENCE: 59
aataaaagaa agtttggggt                                              20

<210> SEQ ID NO 60
<211> LENGTH: 20
<212> TYPE: DNA
<213> ORGANISM: Artificial Sequence
<220> FEATURE:
<223> OTHER INFORMATION: PCR primer

<400> SEQUENCE: 60
gcagagtgct tttagaacat                                              20

<210> SEQ ID NO 61
<211> LENGTH: 20
<212> TYPE: DNA
<213> ORGANISM: Artificial Sequence
<220> FEATURE:
<223> OTHER INFORMATION: PCR primer

<400> SEQUENCE: 61
aggtggaggt tacagtaaga                                              20
```

```
<210> SEQ ID NO 62
<211> LENGTH: 20
<212> TYPE: DNA
<213> ORGANISM: Artificial Sequence
<220> FEATURE:
<223> OTHER INFORMATION: PCR primer

<400> SEQUENCE: 62
aagcagtatc tctgaagctg                                               20

<210> SEQ ID NO 63
<211> LENGTH: 20
<212> TYPE: DNA
<213> ORGANISM: Artificial Sequence
<220> FEATURE:
<223> OTHER INFORMATION: PCR primer

<400> SEQUENCE: 63
ccttttcttg gttcagataa                                               20

<210> SEQ ID NO 64
<211> LENGTH: 21
<212> TYPE: DNA
<213> ORGANISM: Artificial Sequence
<220> FEATURE:
<223> OTHER INFORMATION: PCR primer

<400> SEQUENCE: 64
acggtgtaca catttggtta g                                             21

<210> SEQ ID NO 65
<211> LENGTH: 21
<212> TYPE: DNA
<213> ORGANISM: Artificial Sequence
<220> FEATURE:
<223> OTHER INFORMATION: PCR primer

<400> SEQUENCE: 65
cggatatttg tctgtgatac g                                             21

<210> SEQ ID NO 66
<211> LENGTH: 21
<212> TYPE: DNA
<213> ORGANISM: Artificial Sequence
<220> FEATURE:
<223> OTHER INFORMATION: PCR primer

<400> SEQUENCE: 66
accgtgcaga ggtagatggt a                                             21

<210> SEQ ID NO 67
<211> LENGTH: 20
<212> TYPE: DNA
<213> ORGANISM: Artificial Sequence
<220> FEATURE:
<223> OTHER INFORMATION: PCR primer

<400> SEQUENCE: 67
ccagtggaag agacaggtga                                               20

<210> SEQ ID NO 68
<211> LENGTH: 20
<212> TYPE: DNA
<213> ORGANISM: Artificial Sequence
<220> FEATURE:
<223> OTHER INFORMATION: PCR primer
```

<400> SEQUENCE: 68
gagctgagat cgcaccactt                                              20

<210> SEQ ID NO 69
<211> LENGTH: 21
<212> TYPE: DNA
<213> ORGANISM: Artificial Sequence
<220> FEATURE:
<223> OTHER INFORMATION: PCR primer

<400> SEQUENCE: 69
caacacgaca tggaatggac t                                            21

<210> SEQ ID NO 70
<211> LENGTH: 21
<212> TYPE: DNA
<213> ORGANISM: Artificial Sequence
<220> FEATURE:
<223> OTHER INFORMATION: PCR primer

<400> SEQUENCE: 70
cacagctgga gacatgttac a                                            21

<210> SEQ ID NO 71
<211> LENGTH: 21
<212> TYPE: DNA
<213> ORGANISM: Artificial Sequence
<220> FEATURE:
<223> OTHER INFORMATION: PCR primer

<400> SEQUENCE: 71
agggttcaca ccatatcaga a                                            21

<210> SEQ ID NO 72
<211> LENGTH: 19
<212> TYPE: DNA
<213> ORGANISM: Artificial Sequence
<220> FEATURE:
<223> OTHER INFORMATION: PCR primer

<400> SEQUENCE: 72
acgctgctgt taaggtcca                                               19

<210> SEQ ID NO 73
<211> LENGTH: 21
<212> TYPE: DNA
<213> ORGANISM: Artificial Sequence
<220> FEATURE:
<223> OTHER INFORMATION: PCR primer

<400> SEQUENCE: 73
tgccaattag ccacactctt c                                            21

<210> SEQ ID NO 74
<211> LENGTH: 20
<212> TYPE: DNA
<213> ORGANISM: Artificial Sequence
<220> FEATURE:
<223> OTHER INFORMATION: PCR primer

<400> SEQUENCE: 74
gtgcaaagtg ccttacacag                                              20

<210> SEQ ID NO 75

```
<211> LENGTH: 21
<212> TYPE: DNA
<213> ORGANISM: Artificial Sequence
<220> FEATURE:
<223> OTHER INFORMATION: PCR primer

<400> SEQUENCE: 75
gaggttagac gggtctgagt t                                              21

<210> SEQ ID NO 76
<211> LENGTH: 21
<212> TYPE: DNA
<213> ORGANISM: Artificial Sequence
<220> FEATURE:
<223> OTHER INFORMATION: PCR primer

<400> SEQUENCE: 76
tggcaggcag tagtaactct g                                              21

<210> SEQ ID NO 77
<211> LENGTH: 20
<212> TYPE: DNA
<213> ORGANISM: Artificial Sequence
<220> FEATURE:
<223> OTHER INFORMATION: PCR primer

<400> SEQUENCE: 77
ctgggattac aggtgtctgg                                                20

<210> SEQ ID NO 78
<211> LENGTH: 21
<212> TYPE: DNA
<213> ORGANISM: Artificial Sequence
<220> FEATURE:
<223> OTHER INFORMATION: PCR primer

<400> SEQUENCE: 78
tgagctgttc ccacaccaca t                                              21

<210> SEQ ID NO 79
<211> LENGTH: 21
<212> TYPE: DNA
<213> ORGANISM: Artificial Sequence
<220> FEATURE:
<223> OTHER INFORMATION: PCR primer

<400> SEQUENCE: 79
tcaggacgtt gcactttgac a                                              21

<210> SEQ ID NO 80
<211> LENGTH: 21
<212> TYPE: DNA
<213> ORGANISM: Artificial Sequence
<220> FEATURE:
<223> OTHER INFORMATION: PCR primer

<400> SEQUENCE: 80
gaatgctgga tgtggattga g                                              21

<210> SEQ ID NO 81
<211> LENGTH: 20
<212> TYPE: DNA
<213> ORGANISM: Artificial Sequence
<220> FEATURE:
<223> OTHER INFORMATION: PCR primer

<400> SEQUENCE: 81
```
gagcagaagg ccttgactga                                              20

<210> SEQ ID NO 82
<211> LENGTH: 21
<212> TYPE: DNA
<213> ORGANISM: Artificial Sequence
<220> FEATURE:
<223> OTHER INFORMATION: PCR primer

<400> SEQUENCE: 82
gccttcagtt tgtcccgttc t                                            21

<210> SEQ ID NO 83
<211> LENGTH: 20
<212> TYPE: DNA
<213> ORGANISM: Artificial Sequence
<220> FEATURE:
<223> OTHER INFORMATION: PCR primer

<400> SEQUENCE: 83
cgcgaggtca ggagttcgat                                              20

<210> SEQ ID NO 84
<211> LENGTH: 21
<212> TYPE: DNA
<213> ORGANISM: Artificial Sequence
<220> FEATURE:
<223> OTHER INFORMATION: PCR primer

<400> SEQUENCE: 84
ccactgaaca gggcacaaga t                                            21

<210> SEQ ID NO 85
<211> LENGTH: 21
<212> TYPE: DNA
<213> ORGANISM: Artificial Sequence
<220> FEATURE:
<223> OTHER INFORMATION: PCR primer

<400> SEQUENCE: 85
gaattactgg ctgaggcaac c                                            21

<210> SEQ ID NO 86
<211> LENGTH: 17
<212> TYPE: DNA
<213> ORGANISM: Artificial Sequence
<220> FEATURE:
<223> OTHER INFORMATION: PCR primer

<400> SEQUENCE: 86
gcctgcgctt acatagt                                                 17

<210> SEQ ID NO 87
<211> LENGTH: 21
<212> TYPE: DNA
<213> ORGANISM: Artificial Sequence
<220> FEATURE:
<223> OTHER INFORMATION: PCR primer

<400> SEQUENCE: 87
aggcgggcgg atcacaaggt c                                            21

<210> SEQ ID NO 88
<211> LENGTH: 22
<212> TYPE: DNA

<213> ORGANISM: Artificial Sequence
<220> FEATURE:
<223> OTHER INFORMATION: PCR primer

<400> SEQUENCE: 88
ggctcactgc aacctccacc ta                                                22

<210> SEQ ID NO 89
<211> LENGTH: 24
<212> TYPE: DNA
<213> ORGANISM: Artificial Sequence
<220> FEATURE:
<223> OTHER INFORMATION: PCR primer

<400> SEQUENCE: 89
aaccaaacaa gccagcaatc actc                                              24

<210> SEQ ID NO 90
<211> LENGTH: 22
<212> TYPE: DNA
<213> ORGANISM: Artificial Sequence
<220> FEATURE:
<223> OTHER INFORMATION: PCR primer

<400> SEQUENCE: 90
tgggaggctg aggcaagaga at                                                22

<210> SEQ ID NO 91
<211> LENGTH: 18
<212> TYPE: DNA
<213> ORGANISM: Artificial Sequence
<220> FEATURE:
<223> OTHER INFORMATION: PCR primer

<400> SEQUENCE: 91
actgggcctg ggatgtat                                                     18

<210> SEQ ID NO 92
<211> LENGTH: 19
<212> TYPE: DNA
<213> ORGANISM: Artificial Sequence
<220> FEATURE:
<223> OTHER INFORMATION: PCR primer

<400> SEQUENCE: 92
aaaaattggc tgggtgtgg                                                    19

<210> SEQ ID NO 93
<211> LENGTH: 22
<212> TYPE: DNA
<213> ORGANISM: Artificial Sequence
<220> FEATURE:
<223> OTHER INFORMATION: PCR primer

<400> SEQUENCE: 93
caggctggag tgcaatggtg tg                                                22

<210> SEQ ID NO 94
<211> LENGTH: 22
<212> TYPE: DNA
<213> ORGANISM: Artificial Sequence
<220> FEATURE:
<223> OTHER INFORMATION: PCR primer

<400> SEQUENCE: 94
tgggaggctg aggcaagaga at                                                22

<210> SEQ ID NO 95
<211> LENGTH: 20
<212> TYPE: DNA
<213> ORGANISM: Artificial Sequence
<220> FEATURE:
<223> OTHER INFORMATION: PCR primer

<400> SEQUENCE: 95
ctcactgcag cctcaactcg                                                    20

<210> SEQ ID NO 96
<211> LENGTH: 24
<212> TYPE: DNA
<213> ORGANISM: Artificial Sequence
<220> FEATURE:
<223> OTHER INFORMATION: PCR primer

<400> SEQUENCE: 96
tagcagaagg gggaaggggg aacg                                               24

<210> SEQ ID NO 97
<211> LENGTH: 24
<212> TYPE: DNA
<213> ORGANISM: Artificial Sequence
<220> FEATURE:
<223> OTHER INFORMATION: PCR primer

<400> SEQUENCE: 97
gacggtgtac acatttggtt agtt                                               24

<210> SEQ ID NO 98
<211> LENGTH: 24
<212> TYPE: DNA
<213> ORGANISM: Artificial Sequence
<220> FEATURE:
<223> OTHER INFORMATION: PCR primer

<400> SEQUENCE: 98
gcacagttac atccgcctta tcgt                                               24

<210> SEQ ID NO 99
<211> LENGTH: 24
<212> TYPE: DNA
<213> ORGANISM: Artificial Sequence
<220> FEATURE:
<223> OTHER INFORMATION: PCR primer

<400> SEQUENCE: 99
tgcagacacc cagagaagac gact                                               24

<210> SEQ ID NO 100
<211> LENGTH: 22
<212> TYPE: DNA
<213> ORGANISM: Artificial Sequence
<220> FEATURE:
<223> OTHER INFORMATION: PCR primer

<400> SEQUENCE: 100
tggaccctgc cctcacgatg ga                                                 22

<210> SEQ ID NO 101
<211> LENGTH: 56
<212> TYPE: DNA
<213> ORGANISM: Homo sapiens -continued

```
<400> SEQUENCE: 101
tgggattaca ggtgcatgct accatgcccg gctaattttt ttgtattttt ttagta         56

<210> SEQ ID NO 102
<211> LENGTH: 16
<212> TYPE: DNA
<213> ORGANISM: Homo sapiens

<400> SEQUENCE: 102
accatgcccg gctaat                                                    16

<210> SEQ ID NO 103
<211> LENGTH: 21
<212> TYPE: DNA
<213> ORGANISM: Homo sapiens

<400> SEQUENCE: 103
ctaccatgcc cggctaattt t                                              21

<210> SEQ ID NO 104
<211> LENGTH: 21
<212> TYPE: DNA
<213> ORGANISM: Artificial Sequence
<220> FEATURE:
<223> OTHER INFORMATION: PCR primer

<400> SEQUENCE: 104
tactactggg cctgggatgt a                                              21

<210> SEQ ID NO 105
<211> LENGTH: 22
<212> TYPE: DNA
<213> ORGANISM: Artificial Sequence
<220> FEATURE:
<223> OTHER INFORMATION: PCR primer

<400> SEQUENCE: 105
tagagaaaga cctcgttatt gg                                             22
```

METHODS FOR IDENTIFYING GENOMIC DELETIONS

CROSS-REFERENCE TO RELATED APPLICATION

Figure 1:
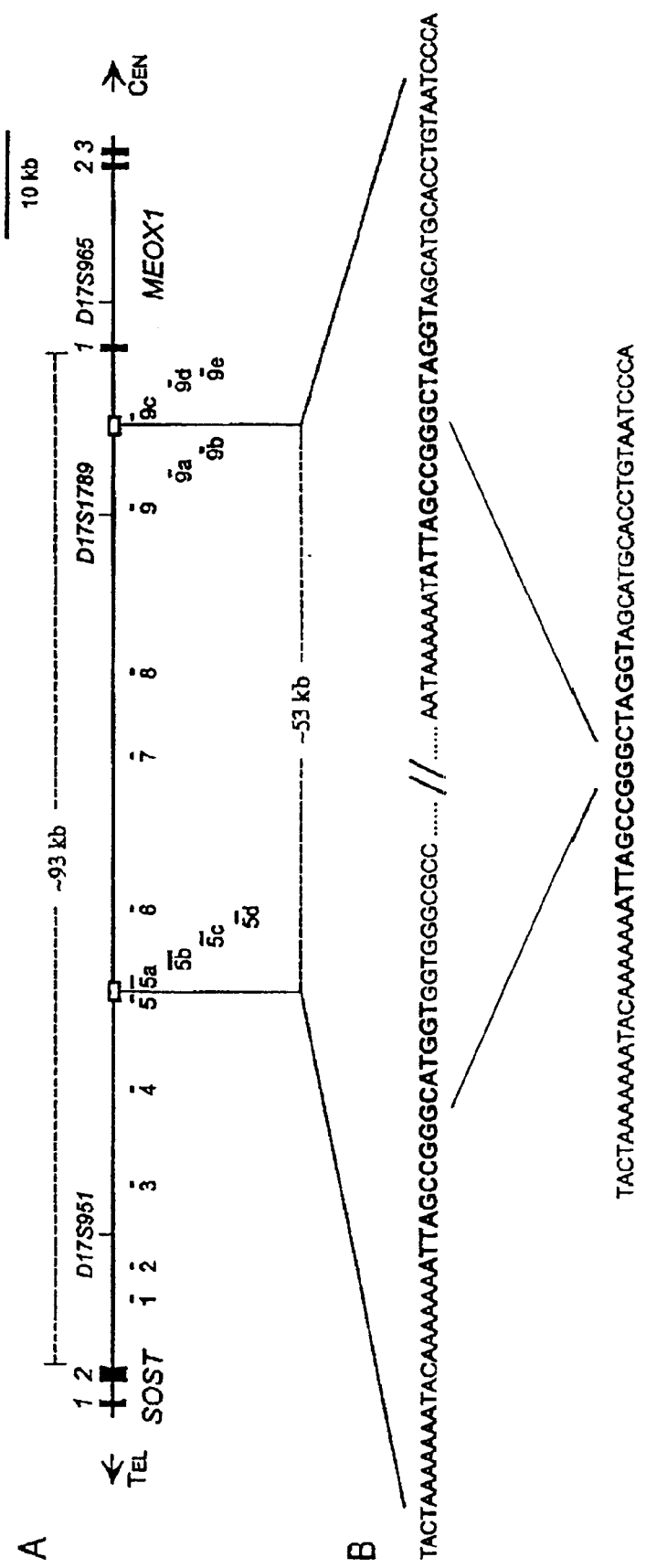

This application claims the benefit of U.S. Provisional Patent Application No. 60/303,386, filed Jul. 6, 2001 and U.S. Provisional Patent Application No. 60/221,855, filed Jul. 28, 2000 where these provisional applications are incorporated herein by reference in their entireties.

BACKGROUND OF THE INVENTION

1. Field of the Invention

This invention relates generally to disease diagnosis and to the identification of disease carriers. More specifically, the present invention provides methods for identifying individuals who are afflicted with or carriers of diseases associated with one or more genomic deletion.

2. Description of the Related Art

Van Buchem's disease (VBD) is a rare autosomal recessive disorder that results in a bone dysplasia referred to as craniotubular hyperostosis. VBD was first described in 1962 as including osteosclerosis of the skull, mandible, clavicles, ribs, and diaphysis of the long bones beginning during puberty and, in some cases, leading to optic atrophy and perceptive deafness from nerve pressure. Van Buchem et al., *Am. J. Med.* 33:387–397 (1962).

More recently, additional occurrences of VBD have been reported. In 1988, Fryns et al. described a 7.5-year-old boy with VBD. This patient had presented at 2 months of age with left-side peripheral facial nerve palsy but had, at that time, no radiologically visible signs of sclerosis of the skull. *Europ. J. Pediat.* 147:99–100 (1988).

In 1997, Balemans et al. studied 11 VBD patients from a highly inbred and geophraphically isolated Dutch family. Each of these patients shared a common ancestor from 9 preceding generations. By applying a genome wide search for linkage using more than 300 microsatellite markers having an average spacing of 10 cM, these authors found a maximum lod score of 9.33 at theta=0.01 with marker D17S1299 and narrowed the assignment to a region of less than 1 cM between markers D17S1787 and D17S934. *Am. J. Hum. Genet.* 61(Suppl.):A12 (1997); See, also, Van Hul et al., *Am. J. Hum. Genet.* 62:391–399 (1998).

A related disease sclerosteosis is an autosomal semi-dominant disease that shares some of the clinical symptoms of VBD. The term "sclerosteosis" has been applied to a disorder similar to Van Buchem hyperostosis corticalis generalisata but differing in the radiologic appearance of the bone changes and in the presence of asymmetric cutaneous syndactyly of the index and middle fingers in many cases. In *Handbuch der Kinderheilkunde* 351–355 (Opitz, H. et al., Berlin: Springer (pub.), 1967). More specifically, this disease resembles VBD in that it comprises a progressive sclerosing bone dysplasia characterized by generalized osteosclerosis and hyperostosis of the skeleton, affecting mainly the skull and mandible thereby causing facial paralysis and hearing loss. In contrast to VBD, however, sclerosteosis is further characterized by gigantism and hand abnormalities.

The rare genetic mutation responsible for the sclerosteosis syndrome has been localized to the region of human chromosome 17 that encodes a novel member of the TGF-beta binding-protein family (one representative example of which is designated "hSOST"). In 1999, Balemans et al. assigned the locus for sclerosteosis to 17q12-q21 which is the same general region as the locus for VBD. *Am. J. Hum. Genet.* 64:1661–1669 (1999). Due to the clinical similarities between VBD and sclerosteosis, Beighton et al. suggested that these conditions might be caused by mutations within the same gene. *Clin. Genet* 25:175–181 (1984). This hypothesis was further supported by the genetic experimentation later performed by Balemans et al. Supra.

Traditional methodologies for identifying genomic deletions such as, for example, restriction fragment length polymorphism (RFLP), fluorescence in situ hybridization (FISH) and Southern blotting permit the identification of individuals who are homozygous for a genomic deletion and, as a consequence, are afflicted with the associated genetic disease. Because these methods are time consuming and/or require high-quality DNA samples or live cells, they are of limited use in the identification of individuals who are heterozygous for and, therefore, carriers of a genetic disease. What is needed in the art are methods that permit the rapid identification of genetic disease carriers, which methods distinguish between individuals who are homozygous for a genomic deletion, individuals who are heterozygous for a genomic deletion and individuals who do not possess a given genomic deletion. As described in detail herein, the present invention fulfills this and other related needs.

BRIEF SUMMARY OF THE INVENTION

The present invention is directed generally to disease diagnosis and to the identification of disease carriers. More specifically, the invention disclosed herein provides methods for identifying chromosomal deletions that are associated with a disease phenotype. Particular methods within the scope of the present invention are directed to the identification of individuals who are afflicted with or carriers for the genomic deletion associated with Van Buchem's disease. By alternate embodiments, the present invention also provides methods having general utility in the detection of a wide variety of diseases characterized by genomic deletions.

The present invention provides, in one embodiment, methods for distinguishing between an individual who is homozygous for a genomic deletion, an individual who is heterozygous for a genomic deletion and an individual who is negative for a genomic deletion.

A first method comprises: (a) obtaining a sample of genomic DNA from an individual; (b) performing a first amplification reaction with a first oligonucleotide primer pair comprising a first oligonucleotide primer and a second oligonucleotide primer wherein the first oligonucleotide primer is complementary to the nucleotide sequence upstream of the genomic deletion and the second oligonucleotide primer is complementary to the nucleotide sequence downstream of said genomic deletion; (c) performing a second amplification reaction with a second oligonucleotide primer pair comprising a third oligonucleotide primer and a fourth oligonucleotide primer wherein the third oligonucleotide primer is complementary to the nucleotide sequence either upstream or downstream of the genomic deletion and the fourth oligonucleotide primer is complementary to the nucleotide sequence comprising the genomic deletion; and (d) detecting the product of the amplification reactions of (b) and (c).

By this first type method, a positive amplification reaction of (b) and a negative amplification reaction of (c) indicates an individual who is homozygous for the large genomic deletion; a positive amplification reaction of (b) and a positive amplification reaction of (c) indicates an individual who is heterozygous for the large genomic deletion; and a negative amplification reaction of (b) and a positive amplification reaction of (c) indicates an individual who is negative for the large genomic deletion.

A second method comprises: (a) obtaining a sample of genomic DNA from said individual; (b) performing an amplification reaction employing at least two oligonucleotide primer pairs in which an oligonucleotide primer is common to both said primer pairs, wherein a first primer pair has a first oligonucleotide primer complementary to a nucleotide sequence that flanks said genomic deletion upstream of said genomic deletion and a second oligonucleotide primer complementary to a nucleotide sequence that flanks said genomic deletion downstream of said genomic deletion, and a second primer pair has third oligonucleotide primer complementary to a nucleotide sequence within said genomic deletion and either said first or second oligonucleotide primer; and (c) detecting an amplified product of said amplification reaction.

By this second method, a positive amplification reaction of said first primer pair and a negative amplification reaction of said second primer pair indicates an individual that is homozygous for said large genomic deletion; a positive amplification reaction of said first primer and a positive amplification reaction of said second primer pair indicates an individual that is heterozygous for said large genomic deletion; and a negative amplification reaction of said first primer pair and a positive amplification reaction of said second primer pair indicates an individual that is negative for said large genomic deletion.

Both these methodologies will find utility in the detection of large genomic deletions comprising at least 2, 3, 4, 5, 6, 7, 8, 9, 10, 15, 20, 25, 30, 40 or 50 kb. By some embodiments, the presence of the large genomic deletion is indicative of an individual who is either afflicted with or a carrier of a genetic disease. The genetic disease is exemplified herein by Van Buchem's disease, but the methods are suitable for any disease characterized by large genomic deletions.

In further embodiments, the present invention provides a first method for identifying individuals who are afflicted with or carriers of Van Buchem's disease. This first method comprises (a) obtaining a sample of genomic DNA from an individual; (b) performing a first amplification reaction with a first oligonucleotide pair primer having a first oligonucleotide primer and a second oligonucleotide primer wherein the first oligonucleotide primer is complementary to the nucleotide sequence upstream of the 51,719 bp sequence depicted in SEQ ID NO:2 which sequence corresponds to nucleotides 5,798 through 57,516 of the 92,149 bp nucleic acid sequence depicted in SEQ ID NO:1 and the second oligonucleotide primer is complementary to the nucleotide sequence downstream of the 51,719 bp sequence depicted in SEQ ID NO:2; and (c) performing a second amplification reaction with a second oligonucleotide pair primer comprising a third oligonucleotide primer and a fourth oligonucleotide primer wherein the third oligonucleotide primer is complementary to the nucleotide sequence either upstream or downstream of the 51,719 bp sequence depicted in SEQ ID NO:2 and the fourth oligonucleotide is complementary to the nucleotide sequence within the 51,719 bp sequence depicted in SEQ ID NO:2; and (d) detecting the product of the amplification reactions of (b) and (c).

By this first method, a positive amplification reaction of (b) and a negative amplification reaction of (c) indicates an individual afflicted with Van Buchem's disease; a positive amplification reaction of (b) and a positive amplification reaction of (c) indicates an individual who is a carrier of Van Buchem's disease; and a negative amplification reaction of (b) and a positive amplification reaction of (c) indicates an individual that is neither afflicted with nor a carrier of Van Buchem's disease.

Exemplary first oligonucleotide primer pairs may be selected from the group consisting of 12952/VBspan1 (SEQ ID NO:84/SEQ ID NO:85), Span1F/Span1R (SEQ ID NO:86/SEQ ID NO:87), Span2F/Span2R (SEQ ID NO:88/SEQ ID NO:89) and Vbspan2/Vbspan1 (SEQ ID NO:104/SEQ ID NO:85). Exemplary second oligonucleotide pairs may be selected from the group consisting of 12952/Wt1R (SEQ ID NO:84/SEQ ID NO:90), Wt2F/Wt2R (SEQ ID NO:91/SEQ ID NO:92), Wt3F/Wt3R (SEQ ID NO:93/SEQ ID NO:94) and VBspan2/VBint1 (SEQ ID NO:105/SEQ ID NO:102).

A second method comprises: (a) obtaining a sample of genomic DNA from said individual; (b) performing a polymerase chain reaction employing at least two oligonucleotide primer pairs in which an oligonucleotide primer is common to both said primer pairs, wherein a first primer pair has a first oligonucleotide primer that is complementary to a nucleotide sequence upstream of the 51,719 bp sequence provided in SEQ ID NO:2 and a second oligonucleotide primer that is complementary to a nucleotide sequence downstream of the 51,719 bp sequence provided in SEQ ID NO:2, and a second primer pair has a third oligonucleotide primer that is complementary to a nucleotide sequence within said genomic deletion and either said first or second oligonucleotide primer; and (c)detecting an amplified product of said amplification reaction.

By this second method, a positive polymerase chain reaction of said first primer pair and a negative polymerase chain reaction of said second primer pair indicates an individual afflicted with Van Buchem's disease; a positive polymerase chain reaction of said first primer pair and a positive polymerase chain reaction of said second primer pair indicates an individual that is a carrier of Van Buchem's disease; and a negative polymerase chain reaction of said first primer pair and a positive polymerase chain reaction of said second primer pair indicates an individual that is neither afflicted with nor a carrier of Van Buchem's disease.

Exemplary first oligonucleotide primer pair is selected from the group consisting of 12952/VBspan1 (SEQ ID NO:84/SEQ ID NO:85), Span1F/Span1R (SEQ ID NO:86/SEQ ID NO:87), Span2F/Span2R (SEQ ID NO:88/SEQ ID NO:89), Wt2F/VBspan1 (SEQ ID NO:91/SEQ ID NO:85) and VBspan2/VBspan1 (SEQ ID NO:104/SEQ ID NO:85).

Still further embodiments of the present invention provide alternative methods for identifying individuals afflicted with Van Buchem's disease. Exemplary methods comprise the steps of performing an amplification reaction with a pair of oligonucleotides selected from the region between nucleotide 1 and nucleotide 51,719 of SEQ ID NO:2 wherein the absence of an amplification product indicates an individual homozygous for Van Buchem's disease. Exemplary oligonucleotide pairs are selected from the group consisting of Del1F/Del1R (SEQ ID NO:95/SEQ ID NO:96), Del2F/Del2R (SEQ ID NO:97/SEQ ID NO:98), and Del3F/Del3R (SEQ ID NO:99/SEQ ID NO:100).

Other embodiments provide methods for identifying an individual who is homozygous for Van Buchem's disease comprising the step of detecting a deletion in human chromosome 17 at 17q21 between nucleotide 5,798 and nucleotide 57,516 as depicted in SEQ ID NO:1.

Figure 2:
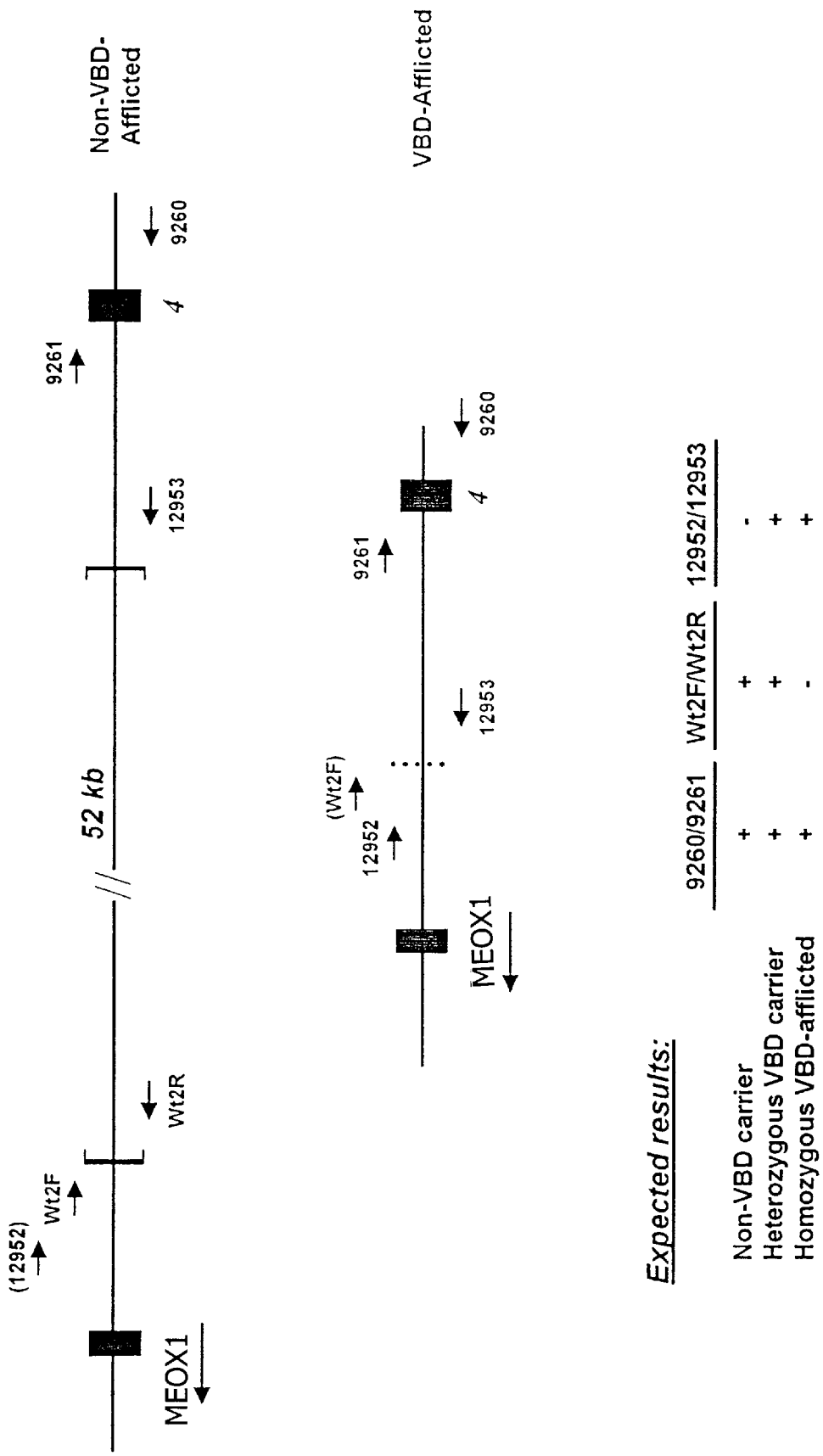

By still other embodiments are provided methods for detecting an individual who is afflicted with or a carrier of Van Buchem's disease which methods comprise detecting the nucleotide sequence spanning the deletion breakpoint as depicted in FIG. 2 and SEQ ID NO:101. By these methods, the presence of a deletion breakpoint indicates an individual who is either afflicted with or a carrier of Van Buchem's disease. Exemplary nucleotide sequences spanning the deletion breakpoint comprise the nucleotide sequence 5'-ACCATGCCCGGCTAAT-3' (SEQ ID NO:102); the nucleotide sequence 5'-CTACCATGCCCGGCTAATTTT-3' (SEQ ID NO:103); and the nucleotide sequence 5'-TGGGATTACAGGTGCATGCTACCATGCCCGG CTAATTTTTTTGTA TTTTTTTAGTA-3' (SEQ ID NO:101).

In still further embodiments of the present invention are provided isolated polynucleotides. Preferred polynucleotides comprise at least 10, 15, 20, 25, 30, 40, 50, 100, 250 or 500 contiguous nucleotides of the nucleic acid depicted in SEQ ID NO:1. Alternatively, isolated polynucleotides according to the present invention hybridize under moderately stringent conditions to the nucleic acid depicted in SEQ ID NO:1 or the complement thereof. Preferred moderately stringent conditions comprise 2xSSC, 0.1% SDS at 65° C.

Other embodiments provide isolated polynucleotides that comprise at least 10, 15, 20, 25, 30, 40, 50, 100, 250 or 500 nucleotides of one of the amplicons comprising the predicted exons within human chromosome 17 at 17q21 which amplicons are selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17.

Still further embodiments of the present invention provide diagnostic kits for distinguishing between an individual who is homozygous for a large genomic deletion, an individual who is heterozygous for a large genomic deletion and an individual who is negative for a large genomic deletion.

A first kit comprises: (a) a first oligonucleotide primer pair comprising a first oligonucleotide primer and a second oligonucleotide primer, wherein said first oligonucleotide primer is complimentary to a nucleotide sequence upstream of said genomic deletion and said second oligonucleotide primer is complementary to a nucleotide sequence downstream of said genomic deletion; and (b) a second oligonucleotide primer pair comprising a third oligonucleotide primer and a fourth oligonucleotide primer wherein said third oligonucleotide primer is complementary to a nucleotide sequence either upstream or downstream of said genomic deletion and said fourth oligonucleotide primer is complementary to a nucleotide sequence within said genomic deletion. These types of diagnostic kit can further comprises instructions for distinguishing between an individual who is homozygous for a large genomic deletion, an individual who is heterozygous for a large genomic deletion and an individual who is negative for a large genomic deletion.

A second kit comprises: (a) a first primer pair having a first oligonucleotide primer that is complementary to a nucleotide sequence that flanks said genomic deletion upstream of said genomic deletion and a second oligonucleotide primer that is complementary to a nucleotide sequence that flanks said genomic deletion downstream of said genomic deletion; and (b) a second primer pair having a third oligonucleotide primer that is complementary to a nucleotide sequence within said genomic deletion and either said first or second oligonucleotide primer.

The genomic deletion mentioned can be associated with Van Buchem's disease. In which case one type of diagnostic kit for identifying a carrier of Van Buchem's disease comprises: (a) a first oligonucleotide primer pair comprising a first oligonucleotide and a second oligonucleotide wherein said first oligonucleotide is complementary to a nucleotide sequence upstream of the 51,719 bp sequence depicted in SEQ ID NO:2 and said second oligonucleotide is complementary to a nucleotide sequence downstream of the 51,719 bp sequence depicted in SEQ ID NO:2; and (b) a second oligonucleotide primer pair comprising a third oligonucleotide and a fourth oligonucleotide wherein said third oligonucleotide is complementary to either the nucleotide sequence upstream or downstream of said 51,719 bp sequence depicted in SEQ ID NO:2 and said fourth oligonucleotide is complementary to a nucleotide sequence within said 51,719 bp sequence depicted in SEQ ID NO:2. These diagnostic kits can further comprise instructions for identifying a carrier of Van Buchem's disease.

A second kit comprises: (a) a first oligonucleotide pair having a first oligonucleotide primer that is complementary to a nucleotide sequence upstream of the 51,719 bp sequence provided in SEQ ID NO:2 and a second oligonucleotide primer that is complementary to a nucleotide sequence downstream of the 51,719 bp sequence depicted in SEQ ID NO:2; and (b) a second oligonucleotide pair having a third oligonucleotide primer that is complementary to a nucleotide sequence within said 51,719 bp sequence provided in SEQ ID NO:2 and either said first or second oligonucleotide primer.

BRIEF DESCRIPTION OF THE SEVERAL VIEWS OF DRAWINGS

FIG. 1A illustrates results obtained from microsatellite typing and exon sequencing of the approximately 90 kb region between the MEOXI and SOST genes within human chromosome region 17q21. FIG. 1B shows the about 53 bp genomic deletion as well as illustrates the nucleotide sequence spanning the deletion breakpoint (SEQ ID NO:101) in nucleic acid sequences obtained from individuals afflicted with Van Buchem's disease.

FIG. 2 illustrates expected results from the polymerase chain reactions utilizing exemplary oligonucleotide primer pairs in the first-described method, where the nucleic acid sample is obtained from an individual who is (1) a non-carrier for Van Buchem's disease; (2) heterozygous for, and therefore a carrier of, Van Buchem's disease; or (3) homozygous for, and therefore afflicted with, Van Buchem's disease.

Figure 3:
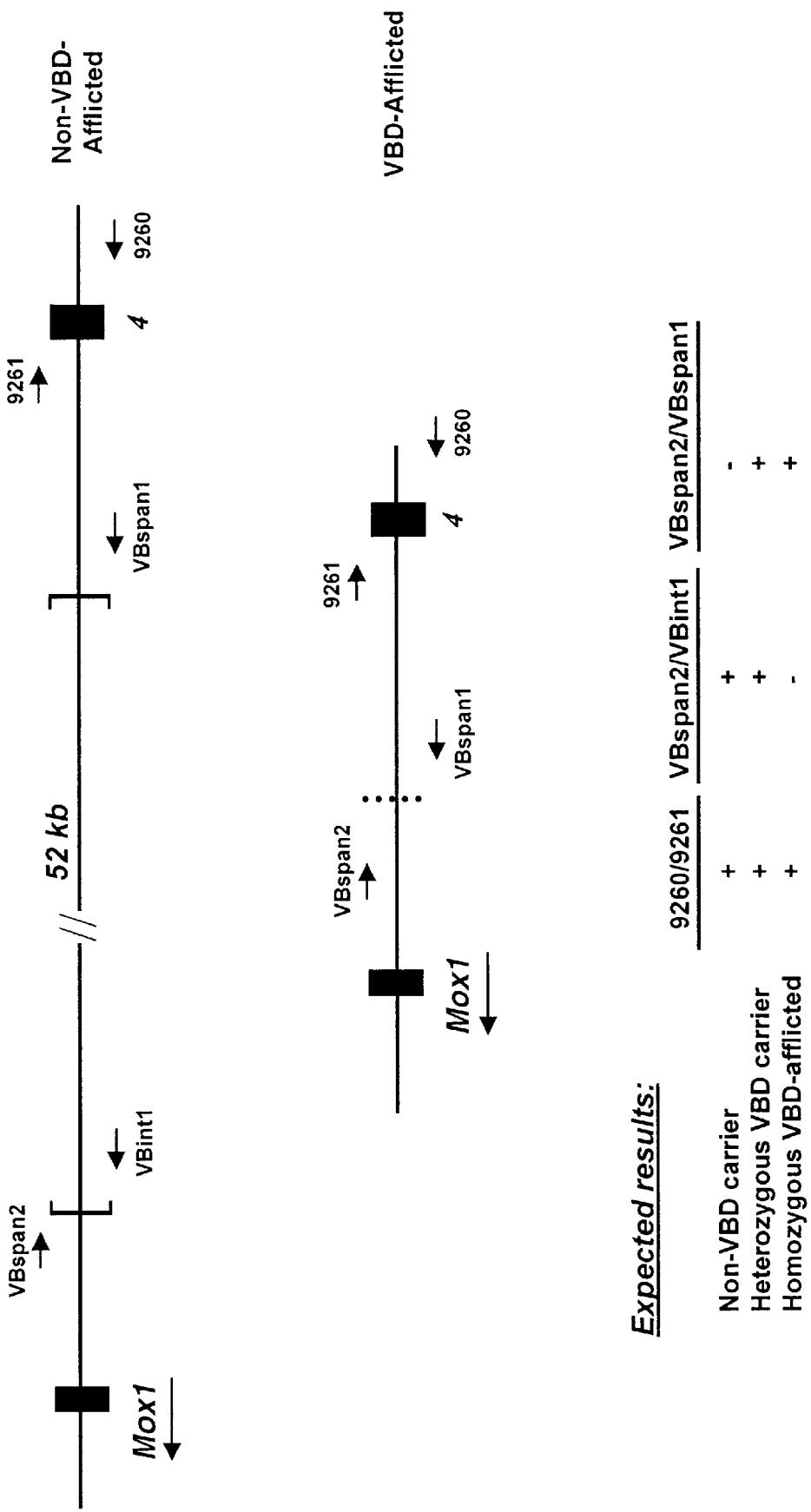

FIG. 3 illustrates expected results from the polymerase chain reaction utilizing exemplary oligonucleotide primer pairs in the second-described method, where the nucleic acid sample is obtained from an individual who is (1) a non-carrier for Van Buchem's disease; (2) heterozygous for, and therefore a carrier of, Van Buchem's disease; or (3) homozygous for, and therefore afflicted with, Van Buchem's disease.

DETAILED DESCRIPTION OF THE INVENTION

As part of the present invention, it was discovered, through haplotype analysis of a number of VBD patients carrying recombinant chromosomes, that the VBD gene localized to a critical region of less than 1 Mb, between the polymorphic markers BP12574 (D17S2250) and JM6307 (D17S2253) (see Example 1). Further microsatellite typing, as well as characterization of the candidate genes within the 1 Mb region through exon sequencing, revealed a specific chromosomal aberration that segregated absolutely with VBD (see Example 3).

As discussed in detail in Example 3, two independent experimental approaches to identifying the VBD candidate region revealed the presence of a chromosomal deletion associated with VBD. First, the oligonucleotide pair D17S1789 (see FIG. 1 and Table 3) did not permit the PCR amplification of a DNA fragment from genomic DNA isolated from VBD patients but did facilitate the amplification of a fragment from normal individuals. Second, nucleotide sequencing and computational analysis, with the GENSCAN exon prediction algorithm of Burge et al., of a 92,149 bp fragment (SEQ ID NO:1) within the human 17q21 chromosomal locus revealed the presence of 15 putative exon sequences. *J. Mol. Biol.* 268:78–94 (1997). As presented in FIG. 1 and as discussed in detail in Example 3, 12 of these 15 exon fragments did not amplify from genomic DNA isolated from VBD-afflicted individuals.

In total, these results demonstrated for the first time the presence of a genomic deletion within human chromosome 17q21 that segregates absolutely with Van Buchem's disease. Furthermore, nucleotide sequencing of the region spanning the deletion breakpoint (SEQ ID NO:101) revealed that approximately 52 kb of contiguous genomic DNA is invariably deleted from chromosome 17 at position 17q21 in individuals afflicted with VBD. The sequence of the 52 kb region is presented herein as SEQ ID NO:2.

Isolated Polynucleotides

As noted above, the present invention provides isolated polynucleotides comprising at least 10, 15, 20, 25, 30, 40, 50, 100, 250, 500, 600, 700, 800 up to and including the 92,101 base pairs (bp) nucleotide sequence of human chromosome 17 at 17q21 disclosed herein as SEQ ID NO:1. Also provided by the present invention are isolated polynucleotides comprising at least 10, 15, 20, 25, 30, 40, 50, 100, 250, 500 bp up to and including the 52 kb sequence of 17q21 that is deleted in individuals who are either afflicted with or carriers of Van Buchem's disease (i.e. SEQ ID NO:2). As well, the present invention provides polynucleotides comprising at least 10, 15, 20, 25, 30, 40, 50, 100, 250, 300, 350, 400, 450, 500, 550, 600, 650, 700, 750, 800, 850 or 890 bp of any of the exons depicted in SEQ ID NOs: 3–17. Other embodiments of the present invention provide oligonucleotide probes of at least 10, 15, 20, 25, 30, 40, 50, 100, 250, 500, 600, 750, 1000, 1050, 1100, 1200 or 1300 that hybridize under moderately stringent conditions to the nucleotide sequence of SEQ ID NO:1 or complements thereto. Exemplary oligonucleotide probes according to the present invention include those designated herein by SEQ ID NOs:28–100.

As used herein, the phrase "isolated polynucleotide" refers to a DNA molecule that has been isolated free of total genomic DNA of a particular species. As will be understood by those skilled in the art, the isolated polynucleotides of the present invention can include genomic sequences, extragenomic and plasmid-encoded sequences and smaller engineered gene segments that express, or may be adapted to express, proteins, polypeptides, peptides and the like. Such segments may be naturally isolated, or synthesized de novo.

Thus, "isolated," as used herein, means that the polynucleotide is substantially separated away from other genomic sequences and that the polynucleotide does not contain large portions of unrelated coding DNA, such as large chromosomal fragments. Of course, this refers to the polynucleotide as originally isolated, and does not exclude genes or coding regions later added to the segment.

As will be recognized by the skilled artisan, isolated polynucleotides may be single-stranded or double-stranded, and may be DNA or RNA molecules. Additional coding or non-coding sequences may, but need not, be present within a polynucleotide of the present invention, and a polynucleotide may, but need not, be linked to other molecules and/or support materials.

It is also contemplated that the present invention encompasses polynucleotides having substantial identity to any of the sequences disclosed herein, for example the present invention encompasses those isolated polynucleotides comprising at least 50% or more sequence identity, preferably at least 55%, 60%, 65%, 70%, 75%, 80%, 85%, 90%, 95%, 96%, 97%, 98%, or 99% or higher, sequence identity compared to a polynucleotide sequence of this invention using the methods described herein, (e.g., BLAST, described in Altschul et al., *J. Mol. Biol.* 215:403–410 (1990)). For the purposes of this invention, a preferred method of calculating percent identity is the Smith-Waterman algorithm, using the following. Global DNA sequence identity must be at least 50% as determined by the Smith-Waterman homology search algorithm as implemented in MPSRCH program (Oxford Molecular) using an affine gap search with the following search parameters: gap open penalty, 12; and gap extension penalty, 1.

In additional embodiments, the present invention provides isolated polynucleotides comprising various lengths of contiguous stretches of sequence identical to or complementary to one or more of the sequences disclosed herein. For example, isolated polynucleotides are provided by this invention that comprise at least about 10, 15, 20, 25, 30, 40, 50, 100, 250, 500, 600, 750, 1000, 1050, 1100, 1200 or 1300 or more contiguous nucleotides of one or more of the sequences disclosed herein.

The polynucleotides of the present invention, or fragments thereof, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

In other embodiments, the present invention is directed to polynucleotides that are capable of hybridizing under moderately stringent conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides includes hybridization in a solution of 2×SSC, 0.1% SDS, 1.0 mM EDTA (pH 8.0) at 65° C.

In still other embodiments of the present invention, the polynucleotide sequences provided herein may be employed as primers in the amplification methodology disclosed herein, infra. As such, it is contemplated that polynucleotides comprising at least about 10 nucleotides that have the same sequence as, or that are complementary to, a 10 nucleotide long contiguous sequence disclosed herein will find utility as an amplification primer. Longer contiguous identical or complementary sequences, e.g., those of about 15, 20, 25, 30, 40, 50, 100, 250, 500, 600, 750, 1000, 1050, 1100, 1200 or 1300 or more will also be of use in certain embodiments.

Small polynucleotide segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 (incorporated herein by reference), by introducing selected sequences into recombinant vectors for recombinant production, and by other recombinant DNA techniques generally known to those of skill in the art of molecular biology. See, e.g., Ausubel et al. (eds.), *Short Protocols in Molecular Biology* (3$^{rd}$ Ed., John Wiley & Sons 1995).

Methodologies for Detecting Van Buchem's Disease Carriers

As noted above, the present invention provides methods for detecting carriers of Van Buchem's disease. More specifically, within certain embodiments, these methods permit the differentiation between individuals who are homozygous for, and therefore afflicted with, VBD; individuals who are heterozygous for, and therefore carriers of, VBD; and individuals who are normal with respect to VBD. As described in detail herein, infra, the presently disclosed methodology will find general utility in the detection of a wide variety of diseases associated with genomic deletions of any length.

The methodology according to the present invention relies, in part, on the inability of various DNA polymerases that are typically utilized in amplification reactions to amplify DNA fragments beyond a maximum nucleotide length. As discussed above, the genomic locus associated with Van Buchem's disease is associated with a large chromosomal deletion of approximately 52 kb at 17q21. Consequently, this deletion results in the juxtapositon of nucleotide sequences present in the genomic DNA of non-VBD-afflicted individuals that are normally separated by greater than 52 kb. Because DNA polymerases normally utilized for the amplification of DNA fragments cannot amplify a 52 kb fragment, a pair of oligonucleotide primers that bind to nucleotide sequences upstream or downstream of this 52 kb region will not permit the amplification of DNA from a non-VBD-afflicted individual. In contrast, however, the same pair of oligonucleotide primers will facilitate the amplification of a DNA fragment from genomic DNA isolated from either a VBD-afflicted individual or from a VBD carrier.

The figures illustrate the genomic DNA corresponding to human chromosome 17 at 17q21 between the MEOXI gene and exon 4. The genomic DNA from non-VBD-afflicted individuals comprises a 52 kb fragment described above while genomic DNA from VBD-afflicted individuals lack this 52 kb region. FIGS. 2 and 3 also illustrate exemplary oligonucleotide primers that hybridize to various regions within the 17q21 locus. Oligonucleotide primers designated VBspan2 and VBspan1/12953, and 12952 and VBspan1/12953 hybridize to nucleotide sequences, on complementary strands, that flank this 52 kb region in normal genomic DNA and, consequently, that flank the deletion breakpoint in genomic DNA from VBD-afflicted individuals. Because of the intervening 52 kb fragment in normal genomic DNA, neither the VBspan2/VBspan1 oligonucleotide primer pair nor the 12952/12953 oligonucleotide primer pair will permit the amplification (e.g., by PCR; see infra) of a DNA fragment from non-VBD-afflicted individuals. In contrast, the VBspan2/VBspan1 oligonucleotide pair primer will facilitate the amplification of a 642 bp fragment, and the 12952/12953 oligonucleotide pair primer will facilitate the amplification of a 798 bp fragment from the DNA of a VBD-afflicted individual.

The methodology according to the present invention additionally permits the differentiation between an individual who is heterozygous for the 52 kb genomic deletion and therefore a carrier of VBD; an individual who is homozygous for the 52 kb genomic deletion and therefore afflicted with VBD; and an individual who is neither a carrier of nor afflicted with VBD. This is achieved by the performance of a second amplification reaction employing a second pair of oligonucleotide primers wherein a third oligonucleotide primer hybridizes to a region of the genomic DNA flanking, either upstream or downstream of, the 52 kb sequence and a fourth oligonucleotide primer hybridizes to a region of the genomic DNA within the 52 kb sequence.

Alternatively, this can be performed using a single multiplex reaction employing a second pair of oligonucleotide primers wherein a third oligonucleotide primer hybridizes to a region of the genomic DNA within the 52 kb sequence and the other oligonucleotide primer is one of the primers from the first oligonucleotide primer pair. Such an oligonucleotide pair is exemplified in FIG. 3 by the VBspan2/VBint1 (SEQ ID NO:104/SEQ ID NO:105) oligonucleotide pair (SEQ ID NO:91/SEQ ID NO:92). As depicted in FIG. 3, a PCR reaction employing this oligonucleotide pair will amplify a 720 bp DNA fragment from the genomic DNA from an individual who is neither afflicted nor a VBD-carrier and from the genomic DNA of a heterozygous VBD-carrier but will not amplify a DNA fragment from the genomic DNA of a homozygous VBD-afflicted individual.

The methodologies according to the present invention permit an alternative approach to differentiating between an individual who is heterozygous for the 52 kb genomic deletion and therefore a carrier of VBD; an individual who is homozygous for the 52 kb genomic deletion and therefore afflicted with VBD; and an individual who is neither a carrier of nor afflicted with VBD, as described in Examples 4 and 5.

In Example 4, this can be achieved using at least two amplification reactions. In Example 5, this can be achieved by the performance of a single multiplex amplification reaction employing at least two oligonucleotide primer pairs, in which one oligonucleotide is common to both pairs. Thus the amplification reaction includes three oligonucleotide primers in total.

Thus, by the present invention provides two methodologies that permit the identification of VBD carriers by allowing the differentiation between an individual who is homozygous for the 52 kb genomic deletion and, therefore, afflicted with VBD; an individual who is heterozygous for the 52 kb genomic deletion and, therefore, a carrier for VBD; and an individual who is normal with respect to the 52 kb deletion and, therefore, neither a carrier of nor afflicted with VBD.

While the present invention discloses the nucleotide sequences of specific exemplary oligonucleotide primers that may be utilized according to the methodologies disclosed herein, it will be apparent to the skilled artisan that alternative oligonucleotide primers may be designed based on the nucleotide sequence depicted in SEQ ID NO:1 which primers are entirely within the scope of the present invention. Thus, for example, suitable oligonucleotide primers according to the present invention include polynucleotides comprising at least 10, 15, 20, 25, 30, 40, 50, 60, 75, 90 or 100 contiguous nucleotides of the nucleic acid depicted in SEQ ID NO:1.

It will also be apparent to one skilled in the art that the choice of reaction conditions and DNA polymerases employed for performing the amplification reactions may be varied in accordance with such parameters as the nucleotide sequence of the oligonucleotide primers and the distance between the primer pairs. Exemplary conditions for 25 ul reactions according to the present methodologies include, but are not limited to, the following: 10 ng genomic DNA; 60 mM TrisHCl pH 7.5; 15 mM ammonium sulfate; 2.5 mM magnesium chloride; 0.4 mM dNTP; and 0.2 uM of each oligonucleotide primer. A typical amplification protocol involves an initial denaturation at 94° C. for 3 min.; 40 cycles of 94° C. for 1 min., 68° C. for 1 min. and 72° C. for 1 min.; and a final extension reaction at 72° C. for 5 min. Amplicons may be resolved by electrophoresis on a 1% agarose gel run in 1×TAE buffer and may be detected by staining with ethidium bromide. Further exemplary conditions for 50 µl reactions according to the present methodologies include, but are not limited to, the following: 20 ng genomic DNA, 0.4 µM each of VBspan1 and VBint1, 0.8 µM of VBspan2, 0.2 mM of each dNTP, 120 mM TrisHCl, pH 7.5, 30 mM ammonium sulfate, 5.0 mM magnesium chloride and 2.5U Taq polymerase (Roche Molecular Biochemicals, Indianapolis, Ind.). A further typical amplification protocol involves an initial denaturation at 94° C. for 3 min, 40 cycles of 94° C. for 30 sec, 63° C. for 30 sec, 72° C. for 2 min and a final extension of 72° C. for 5 min. Amplicons may be resolved by electrophoresis on a 2.5% agarose gel run in 1×TAE buffer and may be detected by staining with ethidium bromide.

Genomic DNA may be isolated by standard procedures that are readily available to those of skill in the art. Representative methodology are provided, for example, in Sambrook et al., *Molecular Cloning: A Laboratory Manual* (Cold Spring Harbor Laboratories, Cold Spring Harbor, N.Y., 1989) and in Ausubel et al. (eds.), *Short Protocols in Molecular Biology* ($4^{th}$ Ed., John Wiley & Sons 1999).

General methodology for performing the polymerase chain reaction (PCR™) are described in detail in U.S. Pat. Nos. 4,683,195; 4,683,202 and 4,800,159, each of which is incorporated herein by reference in its entirety. Briefly, in PCR™, two primers are prepared which have sequences that are complementary to regions on opposite complementary strands of the target sequence. An excess of deoxynucleoside triphosphates is added to a reaction mixture along with a DNA polymerase (e.g., Taq polymerase; see, infra, for exemplary alternative polymerases). If the target sequence is present in a sample, the primers will bind to the target and the polymerase will cause the primers to be extended along the target sequence by adding on nucleotides. By raising and lowering the temperature of the reaction mixture, as indicated, supra, the extended primers will dissociate from the target to form reaction products, excess primers will bind to the target and to the reaction product and the process is repeated.

In addition to the polymerase chain reaction, it is contemplated that alternative amplification procedures that are readily available in the art may be employed in the methodology disclosed herein. For example, another suitable method for amplification is the ligase chain reaction (LCR) and is disclosed in Eur. Pat. Appl. Publ. No. 320,308 (incorporated herein by reference). Briefly, in LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. For a related technique, see also, U.S. Pat. No. 4,883,750, incorporated herein by reference in its entirety.

Alternatively, other methods may be similarly employed in place of the polymerase chain reaction for amplification of nucleic acid sequences include the following: (1) Qbeta Replicase, PCT Intl. Pat. Appl. Publ. No. PCT/US87/00880; (2) the isothermal amplification method of Walker et al.; (3) strand displacement amplification (SDA); (4) repair chain reaction (RCR); (5) cyclic probe reaction (CPR); see, also, Great Britain Pat. Appl. No. 2 202 328, and in PCT Intl. Pat. Appl. Publ. No. PCT/US89/01025; (7) transcription-based amplification systems (TAS) Kwoh et al., 1989; PCT Intl. Pat. Appl. Publ. No. WO 88/110315; (8) Eur. Pat. Appl. Publ. No. 329,822; (9) PCT Intl. Pat. Appl. Publ. No. WO 89/06700; (10) "RACE" (Frohman, 1990); (11) "one-sided PCR" (Ohara, 1989). Each of these methods is incorporated herein by reference.

The choice of DNA polymerase to be employed in the polymerase chain or other amplification reaction can also be determined by the skilled artisan without undue experimentation. As discussed above, the major consideration in selecting an appropriate polymerase is the maximum length of DNA fragment that may be amplified. Such a determination may be achieved initially by reference to the guidelines set forth by the individual manufacturers and ultimately through empirical means by testing stepwise increases in the length of DNA fragment amplified. Additionally or alternatively, the precise reaction condition parameters such as, for example, salt concentration, divalent cation employed and reaction temperature may all be varied in order to adjust, as desired, the length of DNA fragment that may be amplified. The determination of optimal reaction parameters is wholly within the expertise of the skilled artisan.

Exemplary polymerases that may be employed in the present methodology include the various DNA polymerases, and variants thereof, isolated from thermostable bacteria such as the following: Taq, Vent and Deep Vent DNA polymerases (New England BioLabs; Beverly, Mass.); AdvanTaq™, AdvanTaq Plus™, and Advantage$^R$ 2 (Clontech; Palo Alto, Calif.); SuperTaq (Ambion; Austin, Tex.); Tth and Pwo polymerases Roche Molecular Biochemicals; Indianapolis, Ind.); AmpliTaq (PE Biosystems; Foster city, Calif.); and Taq2000 and Pfu DNA polymerases (Stratagene; La Jolla, Calif.).

General Methods for Detection of Large Genomic Deletions

The methodology disclosed herein, supra, for the detection of the large genomic deletion associated with Van Buchem's disease and carriers thereof may be applied broadly, and therefore will find general utility, in the detection of a wide variety of diseases associated with large genomic deletions. In short, the present methods take advantage of the inability of commonly available DNA polymerases to amplify nucleic acid fragments above a certain maximum size when employed in a polymerase chain or other amplification reaction.

Thus, as noted above, the present invention provides general methodologies for distinguishing between an individual who is homozygous for a large genomic deletion, an individual who is heterozygous for a large genomic deletion and an individual who is negative for a large genomic deletion. These methods are discussed in detail in Examples 4 and 5.

As used herein, the phrase "large genomic deletion" refers to those deletions that result from the loss of a contiguous stretch of genomic DNA of such a length that it cannot be amplified in an amplification reaction as disclosed herein, supra. One skilled in the art will recognize, therefore, that the phrase "large genomic deletion" will vary depending on the precise reaction conditions and DNA polymerases employed in the amplification reactions. Generally, the phrase "large genomic deletion" may refer to deletions of at least 2 contiguous kilobases (kb) of genomic DNA. Alternatively, a "large genomic deletion" refers to deletions of at least 3, 4, 5, 6, 7, 8, 9, 10 or more contiguous kb of genomic DNA. Also included within the definition of "large genomic deletions" are deletions of at least 15, 20, 25, 30, 40 or 50 contiguous kb of genomic DNA.

EXAMPLES

The following experimental examples are offered by way of illustration, not limitation.

Example 1
The Van Buchem's Disease Locus Localizes to a Region of Less Than 1 Mb This example discloses that haplotype analysis of a number of Van Buchem's Disease patients carrying recombinant chromosomes localized the disease to a critical region of less than 1 Mb in a region between the polymorphic markers BP12574 (D17S2250) and JM6307 (D17S2253).

The Van Buchem's Disease region was previously localized to the ~1 cM interval between polymorphic markers D17S1787 and D17S1861 on chromosome 17q12-21. To refine the interval further, genomic DNA samples were obtained from 15 affected individuals, 4 of whom had not been previously analyzed. A number of microsatellite markers from chromosome 17q12-21 were used to analyze the DNA samples. Patient DNA samples were genotyped using PCR amplification of polymorphic microsatellite markers. The microsatellite markers selected (see Table 1) are described in public databases or were developed using the SPUTNIK algorithm on sequence obtained from a BAC contig across the van Buchem disease/selerosteosis region (Brunkow et al., *Am. J. Hum. Genet.* 68:577–584 (2001)), D17S1787 to D17S1861. PCR products were labeled with infrared IRDyes™ using an M13 tailing approach as described in Oetting et al., *Genomics* 30:450–458 (1995) and were resolved on a LiCor 4000 DNA sequencer. Allele determinations were made using the SAGA genotyping analysis software (University of Washington) or by a trained eye.

Using this large set of novel polymorphic markers derived from a BAC contig across the D17S1787 and D17S1861 interval, a large region of homozygosity across the disease locus was observed. Furthermore, all affected individuals (including 12–15) shared a common disease haplotype (Table 1). Individuals 2, 3, 6–8 and 12–15 were nonrecombinant across the entire D17S1787–D17S1861 interval, while individuals 1, 4, 5 and 9, 10, 11 carried recombinant chromosomes. Accordingly, the disease locus was refined to the <1 Mb region between BP12574 (D17S2250) and JM6307 (D17S2253) (see Table 1).

TABLE 1

Marker genotypes of affected individuals for selected markers at the van Buchem disease locus on chromosome 17q12–q21

| MARKER | DUTCH VAN BUCHEM DISEASE GENOTYPES AFFECTED INDIVIDUAL | | | | | | CONSENSUS VBD HAPLOTYPE (DUTCH) | CONSENSUS SCLEROSTEOSIS HAPLOTYPE (AFRIKANER) |
|---|---|---|---|---|---|---|---|---|
| | 1 | 4 | 5 | 9 | 10 | 11 | | |
| D17S1787 | 4 4 | 4 4 | 4 4 | 4 *8* | 4 *8* | 4 *8* | 4 | 1 |
| D17S2231 | 4 4 | 4 4 | 4 4 | 4 *11* | 4 *11* | 4 *11* | 4 | 6 |
| D17S1793 | 4 4 | 4 4 | 4 4 | 4 *7* | 4 *7* | 4 *7* | 4 | 4 |
| BP7060 | 11 11 | 11 11 | 11 11 | 11 *12* | 11 *12* | 11 *12* | 11 | 11 |
| BP7872 | 2 2 | 2 2 | 2 2 | 2 *3* | 2 *3* | 2 *3* | 2 | 2 |
| D17S855 | 6 6 | 6 6 | 6 6 | 6 *8* | 6 *8* | 6 *8* | 6 | 7 |
| BP12568 | 1 1 | 1 1 | 1 1 | 1 *3* | 1 *3* | 1 *3* | 1 | ND |
| BP12574 (D17S2250) | 3 3 | 3 3 | 3 3 | 1 *3* | 1 *3* | 1 *3* | 3 | ND |
| BP12578 | 2 2 | 2 2 | 2 2 | 2 2 | 2 2 | 2 2 | 2 | ND |
| BP6991 | 3 3 | 3 3 | 3 3 | 3 3 | 3 3 | 3 3 | 3 | 3 |
| D17S1789 | Δ | Δ | Δ | Δ | Δ | Δ | Δ | 8 |
| D17S951 | 1 1 | 1 1 | 1 1 | 1 1 | 1 1 | 1 1 | 1 | 3 |
| SOST | C | C | C | C | C | C | C | T |
| JM6307 (D17S2253) | 1 *7* | 1 1 | 1 1 | 1 1 | 1 1 | 1 1 | 1 | 4 |
| D17S2234 | 2 *1* | 2 2 | 2 2 | 2 2 | 2 2 | 2 2 | 2 | 2 |
| D17S1860 | 7 *11* | 7 7 | 7 7 | 7 7 | 7 7 | 7 7 | 7 | 10 |
| BP7129 | 2 *6* | 2 2 | 2 2 | 2 2 | 2 2 | 2 2 | 2 | 4 |
| BP7141 | 10 *1* | 10 *1* | 10 *1* | 10 10 | 10 10 | 10 10 | 10 | 8 |
| D17S2235 | 3 *1* | 3 *1* | 3 *1* | 3 3 | 3 3 | 3 3 | 3 | 3 |
| D17S1861 | 8 *13* | 8 *2* | 8 *2* | 8 8 | 8 8 | 8 8 | 8 | 8 |

Example 2
Sclerosteosis and Van Buchem's Haplotypes are Distinct

To determine whether the Dutch van Buchem disease haplotype was related directly to the disease haplotype found in Afrikaner individuals affected with sclerosteosis, sclerosteosis DNA samples were typed with the same set of markers described in Example 1. These were then directly compared to the van Buchem disease DNA samples. The analysis showed marked differences between the two disease haplotypes (Table 1). In instances where the two disease chromosomes carried identical alleles at adjacent markers, true identity by descent (IBD) was unlikely, due either to the fact that one or the other shared allele was found at a high frequency (>0.50) in normal unaffected controls (not shown), or to the close spacing (i.e., <50 kb) between the markers. Finally, the van Buchem disease samples were typed for a single nucleotide polymorphism (SNP) specific for the Afrikaner SOST gene mutation. It was found that they all carried the normal "C" allele. These results indicate that van Buchem disease haplotype is distinct from sclerosteosis haplotype.

Example 3
Van Buchem's Disease is Caused by a Specific Chromosomal Deletion that Represents a Unique Identifier for the Disease Chromosome This example discloses that patients afflicted with VBD have a chromosomal deletion of approximately 52 kb that is correlative of the disease phenotype.

Characterization of all the candidate genes within the 1 Mb region between polymorphic markers BP12574 (D17S2250) and JM6307 (D17S2253) revealed a specific chromosomal aberration that segregated absolutely with Van Buchem's disease. Two independent experimental approaches to identifying the VBD candidate region revealed the presence of a chromosomal deletion associated with VBD.

First, a publicly available oligonucleotide primer pair (i.e. the SSLP designated D17S1789; see FIG. 1A and Table 5) failed to PCR amplify a DNA fragment from genomic DNA obtained from VBD patients while permitting the amplification of a DNA fragment from genomic DNA obtained from normal individuals. As part of the present invention, the nucleotide sequence of a 92,101 bp stretch of genomic DNA from a normal individual, encompassing the D17S1789 amplified fragment, was obtained and is presented herein as SEQ ID NO:1.

Second, the 92 kb stretch of DNA was computationally analyzed, using the GENSCAN exon prediction algorithm, to identify putative exon sequences (Burge et al., *J. Mol. Biol.* 268:78–94 (1997)). PCR primer pairs corresponding to sequences flanking each exon were designed and tested in amplification reactions using as template the genomic DNA obtained from non-VBD-afflicted individuals and individuals afflicted with VBD.

FIG. 1A discloses the normal exon structure across the relevant chromosomal region between the Mox1 and SOST genes, as predicted by the GENSCAN exon prediction algorithm. Exons that amplified from both VBD and normal DNAs are indicated by the filled blocks (i.e. 1–4 and 26–28) while exons that failed to amplify from VBD DNA are indicated by the open blocks (i.e. 9–19). The location of the amplicons that include these exon sequences within the 92 kb nucleic acid of SEQ ID NO:1 and the respective SEQ ID NO assigned to each of the exon sequences as provided by the present invention are indicated in Table 2. The results of these amplification reactions using genomic DNA from VBD afflicted and nonafflicted individuals is summarized in Table 4.

TABLE 2

Amplicons Spanning Potential Exons Predicted by GENSCAN

| Amplicon Name | Amplicon # | Primers (DMO#) | Location in SEQ ID NO:1 | SEQ ID NO |
|---|---|---|---|---|
| Gscn12.210A.09 | 19 | 12098/12104 | 14021-13436 | SEQ ID NO:17 |
| Gscn12.210A.8 | 18 | 12097/12103 | 18353-17837 | SEQ ID NO:16 |
| Gscn12.210A.7 | 17 | 12090/12096 | 18903-18334 | SEQ ID NO:15 |
| Gscn12.210A.6 | 16 | 12089/12095 | 19556-18884 | SEQ ID NO:14 |
| Gscn12.210A.5 | 15 | 12088/12094 | 19593-19063 | SEQ ID NO:13 |
| Gscn12.210A.4 | 14 | 12087/12093 | 29498-28949 | SEQ ID NO:12 |
| Gscn12.210A.3 | 13 | 12086/12092 | 33353-32666 | SEQ ID NO:11 |
| Gscn12.210A.2 | 12 | 12085/12091 | 35036-34373 | SEQ ID NO:10 |
| Gscn12.210A.1 | 11 | 12078/12084 | 36817-36212 | SEQ ID NO:9 |
| Gscn12.668.08 | 10 | 12110/12116 | 49386-49957 | SEQ ID NO:8 |
| Gscn12.668.07 | 9 | 12109/12115 | 50550-51151 | SEQ ID NO:7 |
| Gscn12.668.06 | 4 | 9260/9261 | 58974-58394 | SEQ ID NO:6 |
| Gscn12.668.05 | 3 | 12709/12710 | 58922-59740 | SEQ ID NO:5 |
| Gscn12.668.04 | 2 | 12101/12107 | 67161-67717 | SEQ ID NO:4 |
| Gscn12.668.03 | 1 | 12100/12106 | 75612-76103 | SEQ ID NO:3 |

In total, 16 fragments, corresponding to the SSLP (D17S1789) and at least 15 potential coding exons, were successfully amplified from genomic DNA obtained from non-VBD-afflicted individuals. In contrast, 12 of these 16 fragments did not amplify from genomic DNA obtained from individuals afflicted with VBD. These results revealed the presence of, and partially localized, a genomic deletion within human chromosome 17q21 in the locus associated with VBD (see FIG. 1A).

To better define the endpoints of this chromosomal deletion, additional PCR amplification reactions were performed with primers designed to amplify within the presumably non-coding regions located between the exons at either end of the VBD-specific deletion. The PCR primer pairs used and results obtained are summarized in Tables 3 and 4.

TABLE 3

Amplicons Corresponding to Non-coding Sequences Located within SEQ ID NO:1

| Amplicon Name | Amplicon # | Primers (DMO#) | Location in SEQ ID NO:1 | SEQ ID NO |
|---|---|---|---|---|
| 5'moxA | 25 | 12697/12698 | 1499-1018 | SEQ ID NO:27 |
| 5'moxB | 24 | 12699/12700 | 2524-2065 | SEQ ID NO:26 |
| 5'moxC | 23 | 12701/12702 | 5608-4939 | SEQ ID NO:25 |
| 5'moxD | 22 | 12703/12704 | 8684-8249 | SEQ ID NO:24 |
| 5'moxE | 21 | 12705/12706 | 11248-10880 | SEQ ID NO:23 |
| D17S1789 | 20 | 1789for/rev | 14257-14060 | SEQ ID NO:22 |
| 668intronD | 8 | 12622/12623 | 51371-52377 | SEQ ID NO:21 |
| 668intronC | 7 | 12624/12625 | 53062-54232 | SEQ ID NO:20 |
| 668intronB | 6 | 12626/12627 | 55163-56398 | SEQ ID NO:19 |
| 668intronA | 5 | 12628/12629 | 57103-58202 | SEQ ID NO:18 |

The deletion associated with VBD was further characterized by amplifying a fragment from VBD genomic DNA, using the PCR primer pair 9260/12702 (SEQ ID NO:30/ SEQ ID NO:77), sub-cloning this fragment and sequencing it to completion. As disclosed in FIG. 2, the 9260/12702 primer pair spans the deletion identified in VBD afflicted individuals. The 2317 bp fragment obtained from PCR amplification comprised a deletion breakpoint flanked on both the 5' and 3' ends with normal genomic DNA sequences. Without being limited to any particular theory of the present invention, it is believed that these results indicate that the VBD aberration is a simple chromosomal deletion, with no other associated rearrangements. The nucleotide sequence spanning the deletion breakpoint is depicted in FIG. 1B and is provided in SEQ ID NO:101.

Comparison of the SEQ ID NO:101 with the 92,149 bp sequence obtained from non-VBD-afflicted individuals revealed that approximately 52 kb of contiguous genomic DNA is invariably deleted from chromosome 17 at position 17q21 in individuals afflicted with Van Buchem's disease. This deletion is not present in individuals who are non-carriers or not afflicted with Van Buchem's disease. The sequence of the 52 kb sequence is provided in SEQ ID NO:2.

TABLE 4

Amplification Results Obtained from VBD Affected and Unaffected Genomic DNA Samples

| | | | PCR Results | |
|---|---|---|---|---|
| Amplicon Name | Amplicon # | Primers (DMO#) | VBD Affected | Unaffected |
| Mox1.03 | 28 | 12158/12164 | + | + |
| Mox1.02 | 27 | 12157/12163 | + | + |
| Mox1.0i | 26 | 12265/12156 | + | + |
| 5'moxA | 25 | 12697/12698 | + | + |
| 5'moxB | 24 | 12699/12700 | + | + |
| 5'moxC | 23 | 12701/12702 | + | + |
| 5'moxD | 22 | 12703/12704 | − | + |
| 5'moxE | 21 | 12705/12706 | − | + |
| D17S1789 | 20 | 1789for/rev | − | + |
| gscn12.210A.09 | 19 | 12098/12104 | − | + |
| gscn12.210A.8 | 18 | 12097/12103 | − | + |
| gscn12.210A.7 | 17 | 12090/12096 | − | + |
| gscn12.210A.6 | 16 | 12089/12095 | − | + |
| gscn12.210A.5 | 15 | 12088/12094 | − | + |
| gscn12.210A.4 | 14 | 12087/12093 | − | + |
| gscn12.210A.3 | 13 | 12086/12092 | − | + |
| gscn12.210A.2 | 12 | 12085/12091 | − | + |
| gscn12.210A.1 | 11 | 12078/12084 | − | + |
| gscn12.668.08 | 10 | 12110/12116 | − | + |
| gscn12.668.07 | 9 | 12109/12115 | − | + |
| 668intronD | 8 | 12622/12623 | − | + |
| 668intronC | 7 | 12624/12625 | − | + |
| 668intronB | 6 | 12626/12627 | − | + |
| 668intronA | 5 | 12628/12629 | − | + |
| gscn12.668.06 | 4 | 9260/9261 | + | + |
| gscn12.668.05 | 3 | 12709/12710 | + | + |
| gscn12.668.04 | 2 | 12101/12107 | + | + |
| gscn12.668.03 | 1 | 12100/12106 | + | + |

TABLE 5

Polynucleotide Sequences Derived from SEQ ID NO: 1

| Primer Name | Nucleotide Sequence (5'—3') | SEQ ID NO |
|---|---|---|
| 1789for (5522) | ATTGGCCTGGCTTCTG | SEQ ID NO:28 |
| 1789rev (5524) | GGCTGGAGCAGGGACT | SEQ ID NO:29 |
| 9260 | TCCTGTGATCGCATTGAGAC | SEQ ID NO:30 |
| 9261 | CCCTGCCATTCTGGATAGTTT | SEQ ID NO:31 |
| 12078 | CAGTGGCTTTATTTTCCTAA | SEQ ID NO:32 |
| 12084 | GAAGCTTCTCCATGTTCTTA | SEQ ID NO:33 |
| 12085 | GTCTAAAAATGAAGAAGGCA | SEQ ID NO:34 |
| 12086 | TTAAGTGACTTGTCCGAGAT | SEQ ID NO:35 |
| 12087 | CAACTCAATCTTTTGGTGTT | SEQ ID NO:36 |
| 12088 | AAATCAGATTCAAGCAGTGT | SEQ ID NO:37 |
| 12089 | TCTTAACTGGCTTTTCAGAC | SEQ ID NO:38 |
| 12090 | ATTGTTTCATTTTACCCTCA | SEQ ID NO:39 |
| 12091 | GCCATAAAATCAGGATAATG | SEQ ID NO:40 |
| 12092 | TGCCTAGAACATTCTGGTAT | SEQ ID NO:41 |
| 12093 | CAAAGTGGCTCTGATTATTT | SEQ ID NO:42 |
| 12094 | GGATCTCCTACGTACTGCTA | SEQ ID NO:43 |
| 12095 | TGAGGGTAAAATGAAACAAT | SEQ ID NO:44 |
| 12096 | AAAGACACTGCAGAGAAAAG | SEQ ID NO:45 |
| 12097 | CTTTTCTCTGCAGTGTCTTT | SEQ ID NO:46 |
| 12098 | GAGACCTCTCCTCTTTGAAT | SEQ ID NO:47 |
| 12100 | GGTTTCAACTAGTTCTGGTG | SEQ ID NO:48 |
| 12101 | CTAGGGCTTAGAAGTTTCCT | SEQ ID NO:49 |
| 12103 | ACTCCTAGAACCCTAAAGGA | SEQ ID NO:50 |
| 12104 | GTATCACCAGTGAAGTTGGT | SEQ ID NO:51 |
| 12106 | GATAAATGGATATGCAAAG | SEQ ID NO:52 |
| 12107 | GGTTTATAATTTGCAACCAG | SEQ ID NO:53 |
| 12109 | ATTCCCTAAGAGATTTGTCC | SEQ ID NO:54 |
| 12110 | GAGAGGACAAACATTCAAAC | SEQ ID NO:55 |
| 12115 | TTTAGACCTATCACTCCCAA | SEQ ID NO:56 |
| 12116 | CTACTGGGACAAACCATTAC | SEQ ID NO:57 |
| 12156 | AGAGAGGGTGAGTAACTTCC | SEQ ID NO:58 |
| 12157 | AATAAAAGAAAGTTTGGGGT | SEQ ID NO:59 |
| 12158 | GCAGAGTGCTTTTAGAACAT | SEQ ID NO:60 |
| 12163 | AGGTGGAGGTTACAGTAAGA | SEQ ID NO:61 |
| 12164 | AAGCAGTATCTCTGAAGCTG | SEQ ID NO:62 |
| 12265 | CCTTTTCTTGGTTCAGATAA | SEQ ID NO:63 |
| 12622 | ACGGTGTACACATTTGGTTAG | SEQ ID NO:64 |
| 12623 | CGGATATTTGTCTGTGATACG | SEQ ID NO:65 |
| 12624 | ACCGTGCAGAGGTAGATGGTA | SEQ ID NO:66 |
| 12625 | CCAGTGGAAGAGACAGGTGA | SEQ ID NO:67 |
| 12626 | GAGCTGAGATCGCACCACTT | SEQ ID NO:68 |
| 12627 | CAACACGACATGGAATGGACT | SEQ ID NO:69 |
| 12628 | CACAGCTGGAGACATGTTACA | SEQ ID NO:70 |
| 12629 | AGGGTTCACACCTATCAGAA | SEQ ID NO:71 |
| 12697 | ACGCTGCTGTTAAGGTCCA | SEQ ID NO:72 |
| 12698 | TGCCAATTAGCCACACTCTTC | SEQ ID NO:73 |
| 12699 | GTGCAAAGTGCCTTACACAG | SEQ ID NO:74 |
| 12700 | GAGGTTAGACGGGTCTGAGTT | SEQ ID NO:75 |
| 12701 | TGGCAGGCAGTAGTAACTCTG | SEQ ID NO:76 |
| 12702 | CTGGGATTACAGGTGTCTGG | SEQ ID NO:77 |
| 12703 | TGAGCTGTTCCCACACCACAT | SEQ ID NO:78 |
| 12704 | TCAGGACGTTGCACTTTGACA | SEQ ID NO:79 |
| 12705 | GAATGCTGGATGTGGATTGAG | SEQ ID NO:80 |
| 12706 | GAGCAGAAGGCCTTGACTGA | SEQ ID NO:81 |
| 12709 | GCCTTCAGTTTGTCCCGTTCT | SEQ ID NO:82 |
| 12710 | CGCGAGGTCAGGAGTTCGAT | SEQ ID NO:83 |
| 12952 | CCACTGAACAGGGCACAAGAT | SEQ ID NO:84 |
| VBspan1/ 12953 | GAATTACTGGCTGAGGCAACC | SEQ ID NO:85 |
| Span1F | GCCTGCGCTTACATAGT | SEQ ID NO:86 |
| Span1R | AGGCGGGCGGATCACAAGGTC | SEQ ID NO:87 |
| Span2F | GGCTCACTGCAACCTCCACCTA | SEQ ID NO:88 |
| Span2R | AACCAAACAAGCCAGCAATCACTC | SEQ ID NO:89 |
| Wt1R | TGGGAGGCTGAGGCAAGAGAAT | SEQ ID NO:90 |
| Wt2F | ACTGGGCCTGGGATGTAT | SEQ ID NO:91 |
| Wt2R | AAAAATTGGCTGGGTGTGG | SEQ ID NO:92 |
| Wt3F | CAGGCTGGAGTGCAATGGTGTG | SEQ ID NO:93 |
| Wt3R | TGGGAGGCTGAGGCAAGAGAAT | SEQ ID NO:94 |
| Del1F | CTCACTGCAGCCTCAACTCG | SEQ ID NO:95 |
| Del1R | TAGCAGAAGGGGAAGGGGAACG | SEQ ID NO:96 |
| Del2F | GACGGTGTACACATTTGGTTAGTT | SEQ ID NO:97 |
| Del2R | GCACAGTTACATCCGCCTTATCGT | SEQ ID NO:98 |

TABLE 5-continued

Polynucleotide Sequences Derived from SEQ ID NO: 1

| Primer Name | Nucleotide Sequence (5'—3') | SEQ ID NO |
|---|---|---|
| Del3F | TGCAGACACCCAGAGAAGACGACT | SEQ ID NO:99 |
| Del3R | TGGACCCTGCCCTCACGATGGA | SEQ ID NO:100 |
| VBspan2 | TACTACTGGGCCTGGGATGTA | SEQ ID NO:104 |
| VBint1 | TAGAGAAAGACCTCGTTATTGG | SEQ ID NO:105 |

Example 4
First Methodology for Identification of Van Buchem's Disease Carriers by Detection of a 52 KB Genomic Deletion This example discloses a methodology for distinguishing individuals who are afflicted with or carriers of Van Buchem's disease as well as from individuals who are normal with respect to the 52 kb deletion. The methodology is based on the observation that the large, i.e. 52 kb genomic deletion that correlates absolutely with Van Buchem's disease may be identified by amplification of the region encompassing the deletion breakpoint.

The deletion on the Van Buchem's disease chromosomal locus 17q21 results in the apposition of DNA sequences normally separated by approximately 52 kb. A PCR assay specific for the deleted chromosome was developed. Starting with the sequence of the 2.3 kb VBD-specific fragment that includes the deletion endpoints, primers were designed to span the endpoints and yield a 400–800 bp amplicon from VBD DNA but would not, because of the presence of the 52 kb genomic fragment, permit the amplification of any fragment from normal, non-carrier genomic DNA samples.

As illustrated in FIG. 2, the following oligonucleotide primer pairs were used to amplify chromosomal DNA within the locus 17q21 from individuals who are afflicted with or carriers of VBD: Primer Nos. 12952 and 12953 hybridize within the region upstream and downstream, respectively, of the 52 kb genomic region deleted in VBD-afflicted individuals and amplify a 798 bp fragment when the 52 kb region is deleted; Primer Nos. Wt2F and Wt2R hybridize upstream of and within, respectively, the 52 kb genomic region deleted in VBD-afflicted individuals and amplify a 473 bp fragment in the absence of the deletion; Primer Nos. 9261 and 9260 hybridize within the region downstream of the 52 kb genomic region deleted in VBD-afflicted individuals and amplify a 581 bp fragment in all cases.

The VBD diagnostic was designed such that individuals who are homozygous for the 52 kb deletion and therefore afflicted with VBD may be differentiated from individuals who are heterozygous for the 52 kb deletion and therefore carriers of VBD as well as individuals who are normal with respect to the 52 kb deletion. Two separate PCR reactions were performed on the individual to be tested. In the first, a primer pair spanning upstream and within the VBD deletion (i.e. the Wt2F/Wt2R oligonucleotide primer pair) yielded an amplicon from normal non-carriers and heterozygous carriers. In the second reaction, primers which span the 52 kb deletion (i.e. the 12952/12953 oligonucleotide primer pair) yielded an amplicon from heterozygous VBD carriers and homozygous patients. A primer pair spanning a region unaffected by the 52 kb genomic deletion (i.e. the 9260/9261 oligonucleotide primer pair) was included as a positive control for the PCR reactions.

The following reaction conditions were used for amplification of 400 to 800 bp nucleic acid fragments using as template genomic DNA isolated from patients who are afflicted with or carriers of Van Buchem's disease: 25 ul reactions included 10 ng genomic DNA; 60 mM TrisHCl, pH 7.5; 15 mM Ammonium Sulfate; 2.5 mM Magnesium Chloride; 0.4 mM each of dATP, dCTP, dGTP and dTTP; 0.2 µM each of Primer Nos. Wt2F and Wt2R, or 12952 and 12953, or 9260 and 9261. The fragments (473, 798, and 581 bp, respectively) were amplified by the following protocol: Denaturation at 94° C. for 3; 40 cycles of 94° C. for 1 minute, 68° C. for 1 minute and 72° C. for 1 minute; final extension at 72° C. for 5 minutes. The amplified nucleic acid fragments were resolved on a 1% agarose gel using 1×TAE buffer. DNA bands were visualized with ethidium bromide staining.

The results are summarized in FIG. 2. The summary shows that nucleic acid fragments amplified in all PCR reactions containing the 9260/9261 oligonucleotide primer pair regardless of the source of genomic DNA template. The 12952/001 oligonucleotide primer pair amplified a nucleic acid fragment from non-VBD afflicted individuals and individuals who are heterozygous for and therefore carriers of VBD but did not amplify a nucleic acid fragment from individuals who are homozygous for and therefore afflicted with VBD. The 12952/12953 oligonucleotide primer pair amplified a nucleic acid fragment from individuals who are heterozygous for and therefore carriers of VBD and from individuals who are homozygous for and therefore afflicted with VBD but did not amplify a nucleic acid fragment from non-VBD afflicted individuals.

These results demonstrated that a first methodology presented herein permit the differentiation between an individual who is homozygous for the 52 kb genomic deletion and therefore afflicted with VBD, an individual who is heterozygous for the 52 kb genomic deletion and therefore a carrier of VBD and an individual who does not bear the 52 kb genomic deletion and is therefore normal with respect to VBD.

Example 5

Second Methodology for Identification of Van Buchem's Disease Carriers by Detection of a 52 KB Genomic Deletion This example discloses a second methodology for identifying individuals who are afflicted with or carriers of Van Buchem's disease as well as from individuals who are normal with respect to the 52 kb deletion. The methodology is based on the observation that the large, i.e. 52 kb genomic deletion that correlates absolutely with Van Buchem's disease may be identified by amplification of the region encompassing the deletion breakpoint.

As illustrated in FIG. 3, the following oligonucleotide primer pairs were used to amplify chromosomal DNA within the locus 17q21 from individuals who are afflicted with or carriers of VBD: Primers VBspan2 and VBspan1 hybridize upstream and downstream, respectively, to a region that flanks the 52 kb genomic region deleted in VBD-afflicted individuals and amplify a 642 bp fragment when the 52 kb region is deleted. Primer VBint hybridizes within the 52 kb genomic region which is deleted in VBD-afflicted individuals and with primer VBspan2 amplify a 720 bp fragment in the absence of the deletion.

The VBD diagnostic was designed such that individuals who are homozygous for the 52 kb deletion and therefore afflicted with VBD may be differentiated from individuals who are heterozygous for the 52 kb deletion and therefore carriers of VBD as well as individuals who are normal with respect to the 52 kb deletion.

A single multiplexed PCR reaction was performed on the individual to be tested. The pair of oligonucleotide primers span the 52 kb deletion (i.e. the VBspan1/VBspan2 oligonucleotide primer pair) yielded an amplicon from heterozygous VBD carriers and homozygous patients. The second pair of oligonucleotide primers pair spanning upstream and within the VBD deletion (i.e. the VBspan2/VBint1 oligonucleotide primer pair) yielded an amplicon from normal non-carriers and heterozygous carriers. A primer pair spanning a region unaffected by the 52 kb genomic deletion (i.e. the 9260/9261 oligonucleotide primer pair) was included as a positive control for the PCR reactions.

The following reaction conditions were used for amplification of 400 to 800 bp nucleic acid fragments using as template chromosomal DNA isolated from patients who are afflicted with or carriers of Van Buchem's disease: 50 µl reactions include 20 ng genomic DNA, 0.4 µM each of Vbspan1 and Vbint1, 0.8 µM of VBspan2, 0.2 mM of each dNTP, 120 mM TrisHCl, pH 7.5, 30 mM ammonium sulfate, 5.0 mM magnesium chloride and 2.5U Taq polymerase (Roche Molecular Biochemicals, Indianopolis, Ind.). The fragments (642 and 720 bp) were amplified by the following protocol: Denaturation at 94° C. for 3 min, 40 cycles of 94° C. for 30 sec, 63° C. for 30 sec, 72° C. for 2 min and a final extension of 72° C. for 5 min. The amplified nucleic acid fragments were resolved on a 2.5% agarose gel using 1×TAE buffer. DNA bands were visualized with ethidium bromide staining.

The results are summarized in FIG. 3. The summary shows that nucleic acid fragments amplified in all PCR reactions containing the 9260/9261 oligonucleotide primer pair regardless of the source of genomic DNA template. The VBspan2/VBint1 oligonucleotide primer pair amplified a nucleic acid fragment from non-VBD afflicted individuals and individuals who are heterozygous for and therefore carriers of VBD but did not amplify a nucleic acid fragment from individuals who are homozygous for and therefore afflicted with VBD. The VBspan2/VBspan1 oligonucleotide primer pair amplified a nucleic acid fragment from individuals who are heterozygous for and therefore carriers of VBD and from individuals who are homozygous for and therefore afflicted with VBD but did not amplify a nucleic acid fragment from non-VBD afflicted individuals.

These results demonstrated that a second methodology presented herein permit the differentiation between an individual who is homozygous for the 52 kb genomic deletion and therefore afflicted with VBD, an individual who is heterozygous for the 52 kb genomic deletion and therefore a carrier of VBD and an individual who does not bear the 52 kb genomic deletion and is therefore normal with respect to VBD in a single multiplexed amplification reaction.

In providing the forgoing description of the invention, citation has been made to several references that will aid in the understanding or practice thereof. All such references are incorporated by reference herein.

From the forgoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for distinguishing between an individual who is homozygous for a large genomic deletion, an individual who is heterozygous for a large genomic deletion and an individual who is negative for a large genomic deletion, said method comprising:
   (a) obtaining a sample of genomic DNA from said individual;
   (b) performing a first amplification reaction with a first oligonucleotide primer pair comprising a first oligonucleotide and a second oligonucleotide wherein said first oligonucleotide is complementary to a nucleotide sequence upstream of said genomic deletion and said second oligonucleotide is complementary to a nucleotide sequence downstream of said genomic deletion;
   (c) performing a second amplification reaction with a second oligonucleotide primer pair comprising a third oligonucleotide and a fourth oligonucleotide wherein said third oligonucleotide is complementary to a nucleotide sequence either the upstream or downstream of said genomic deletion and said fourth oligonucleotide is complementary to a nucleotide sequence within said genomic deletion; and
   (d) detecting the product of the amplification reactions of (b) and (c); wherein a positive amplification reaction of (b) and a negative amplification reaction of (c) indicates an individual that is homozygous for said large genomic deletion; a positive amplification reaction of (b) and a positive amplification reaction of (c) indicates an individual that is heterozygous for said large genomic deletion; and a negative amplification reaction of (b) and a positive amplification reaction of (c) indicates an individual that is negative for said large genomic deletion.

2. The method of claim 1, wherein said large genomic deletion comprises a deletion selected from the group consisting of:
   (a) deletions of at least 2 kilobases;
   (b) deletions of at least 5 kilobases;
   (c) deletions of at least 10 kilobases;
   (d) deletions of at least 25 kilobases; and
   (e) deletions of at least 50 kilobases.

3. The method of claim 1 wherein said amplification reaction comprises the polymerase chain reaction.

4. The method of claim 1 wherein the presence of said large genomic deletion indicates an individual who is either a carrier of or afflicted with a genetic disease.

5. The method of claim 4 wherein said genetic disease is Van Buchem's disease.

6. A method for identifying a carrier of Van Buchem's disease, said method comprising:

(a) obtaining a sample of genomic DNA from said individual;

(b) performing a first polymerase chain reaction with a first oligonucleotide primer pair comprising a first oligonucleotide and a second oligonucleotide wherein said first oligonucleotide is complementary to a nucleotide sequence upstream of the 51,719 bp sequence depicted in SEQ ID NO:2 and said second oligonucleotide is complementary to a nucleotide sequence downstream of the 51,719 bp sequence depicted in SEQ ID NO:2;

(c) performing a second polymerase chain reaction with a second oligonucleotide primer pair comprising a third oligonucleotide and a fourth oligonucleotide wherein said third oligonucleotide is complementary to either the nucleotide sequence upstream or downstream of said 51,719 bp sequence depicted in SEQ ID NO:2 and said fourth oligonucleotide is complementary to a nucleotide sequence within the 51,719 bp sequence depicted in SEQ ID NO:2; and (d) detecting the product of the polymerase chain reactions of (b) and (c), wherein a positive polymerase chain reaction of (b) and a negative polymerase chain reaction of (c) indicates an individual afflicted with Van Buchem's disease; a positive polymerase chain reaction of (b) and a positive polymerase chain reaction of (c) indicates an individual that is a carrier of Van Buchem's disease; and a negative polymerase chain reaction of (b) and a positive polymerase chain reaction of (c) indicates an individual that is neither afflicted with nor a carrier of Van Buchem's disease.

7. The method of claim 6 wherein said first oligonucleotide pair is selected from the group consisting of 12952/VBspan1 (SEQ ID NO:84/SEQ ID NO:85), Span1F/Span1R (SEQ ID NO:86/SEQ ID NO:87), Span2F/Span2R (SEQ ID NO:88/SEQ ID NO:89), Wt2F/VBspan1 (SEQ ID NO:91/SEQ ID NO:85) and VBspan2/VBspan1 (SEQ ID NO:104/SEQ ID NO:85).

8. A method for identifying an individual who is afflicted with Van Buchem's disease comprising performing a polymerase chain reaction with a pair of oligonucleotides selected from the region between nucleotide 1 and nucleotide 51,719 of SEQ ID NO:2 wherein the absence of an amplification product indicates an individual homozygous for Van Buchem's disease.

9. The method of claim 8 wherein said pair of oligonucleotides is selected from the group consisting of Del1F/Del1R (SEQ ID NO:95/SEQ ID NO:96), Del2F/Del2R (SEQ ID NO:97/SEQ ID NO:98), and Del3F/Del3R (SEQ ID NO:99/SEQ ID NO:100).

10. A diagnostic kit for identifying a carrier of Van Buchem's disease, said kit comprising:

(a) a first oligonucleotide primer pair comprising a first oligonucleotide and a second oligonucleotide wherein said first oligonucleotide is complementary to a nucleotide sequence upstream of the 51,719 bp sequence depicted in SEQ ID NO:2 and said second oligonucleotide is complementary to a nucleotide sequence downstream of the 51,719 bp sequence depicted in SEQ ID NO:2; and (b) a second oligonucleotide primer pair comprising a third oligonucleotide and a fourth oligonucleotide wherein said third oligonucleotide is complementary to either the nucleotide sequence upstream or downstream of said 51,719 bp sequence depicted in SEQ ID NO:2 and said fourth oligonucleotide is complementary to a nucleotide sequence within said 51,719 bp sequence depicted in SEQ ID NO:2.

11. The diagnostic kit of claim 10 further comprising instructions for identifying a carrier of Van Buchem's disease.

12. A method for distinguishing between an individual who is homozygous for a large genomic deletion, an individual who is heterozygous for a large genomic deletion and an individual who is negative for a large genomic deletion, said method comprising:

(a) obtaining a sample of genomic DNA from said individual;

(b) performing an amplification reaction employing at least two oligonucleotide primer pairs in which an oligonucleotide primer is common to both said primer pairs, wherein a first primer pair has a first oligonucleotide primer complementary to a nucleotide sequence that flanks said genomic deletion upstream of said genomic deletion and a second oligonucleotide primer complementary to a nucleotide sequence that flanks said genomic deletion downstream of said genomic deletion, and a second primer pair has third oligonucleotide primer complementary to a nucleotide sequence within said genomic deletion and either said first or second oligonucleotide primer; and (c) detecting an amplified product of said amplification reaction, wherein a positive amplification reaction of said first primer pair and a negative amplification reaction of said second primer pair indicates an individual that is homozygous for said large genomic deletion; a positive amplification reaction of said first primer and a positive amplification reaction of said second primer pair indicates an individual that is heterozygous for said large genomic deletion; and a negative amplification reaction of said first primer pair and a positive amplification reaction of said second primer pair indicates an individual that is negative for said large genomic deletion.

13. The method of claim 12, wherein said large genomic deletion comprises a deletion selected from the group consisting of:

(a) deletions of at least 2 kilobases;

(b) deletions of at least 5 kilobases;

(c) deletions of at least 10 kilobases;

(d) deletions of at least 25 kilobases; and (e) deletions of at least 50 kilobases.

14. The method of claim 12 wherein said amplification reaction comprises the polymerase chain reaction.

15. The method of claim 12 wherein the presence of said large genomic deletion indicates an individual who is either a carrier of or afflicted with a genetic disease.

16. The method of claim 15 wherein said genetic disease is Van Buchem's disease.

17. A method for identifying a carrier of Van Buchem's disease, said method comprising:

(a) obtaining a sample of genomic DNA from said individual;

(b) performing a polymerase chain reaction employing at least two oligonucleotide primer pairs in which an oligonucleotide primer is common to both said primer pairs, wherein a first primer pair has a first oligonucleotide primer that is complementary to a nucleotide sequence upstream of the 51,719 bp sequence provided in SEQ ID NO:2 and a second oligonucleotide primer that is complementary to a nucleotide sequence downstream of the 51,719 bp sequence provided in SEQ ID NO:2, and a second primer pair has a third oligonucleotide primer that is complementary to a nucleotide sequence within said genomic deletion and either said first or second oligonucleotide primer; and (c) detecting an amplified product of said amplification reaction, wherein a positive polymerase chain reaction of said first primer pair and a negative polymerase chain reaction of said second primer pair indicates an individual afflicted with Van Buchem's disease; a positive polymerase chain reaction of said first primer pair and a positive polymerase chain reaction of said second primer pair indicates an individual that is a carrier of Van Buchem's disease; and a negative polymerase chain reaction of said first primer pair and a positive polymerase chain reaction of said second primer pair indicates an individual that is neither afflicted with nor a carrier of Van Buchem's disease.

18. The method of claim 17 wherein said first oligonucleotide primer pair is selected from the group consisting of 12952/VBspan1 (SEQ ID NO:84/SEQ ID NO:85), Span1F/Span1R (SEQ ID NO:86/SEQ ID NO:87), Span2F/Span2R (SEQ ID NO:88/SEQ ID NO:89), Wt2F/VBspan1 (SEQ ID NO:91/SEQ ID NO:85) and VBspan2/VBspan1 (SEQ ID NO:104/SEQ ID NO:85).

19. A diagnostic kit for identifying a carrier of Van Buchem's disease, said kit comprising:

(a) a first oligonucleotide pair having a first oligonucleotide primer that is complementary to a nucleotide sequence upstream of the 51,719 bp sequence provided in SEQ ID NO:2 and a second oligonucleotide primer that is complementary to a nucleotide sequence downstream of the 51,719 bp sequence depicted in SEQ ID NO:2; and (b) a second oligonucleotide pair having a third oligonucleotide primer that is complementary to a nucleotide sequence within said 51,719 bp sequence provided in SEQ ID NO:2 and either said first or second oligonucleotide primer.

* * * * *